US012653929B2

(12) United States Patent
Xu et al.

(10) Patent No.: US 12,653,929 B2
(45) Date of Patent: Jun. 16, 2026

(54) TENDON-MIMETIC MATERIALS WITH ANISOTROPIC ASSEMBLY OF ARAMID NANOFIBERS

(71) Applicant: The University of Hong Kong, Hong Kong (CN)

(72) Inventors: Lizhi Xu, Changsha (CN); Mingze Sun, Shenyang (CN); Hegeng Li, Wuhan (CN)

(73) Assignee: The University of Hong Kong, Hong Kong (CN)

( * ) Notice: Subject to any disclaimer, the term of this patent is extended or adjusted under 35 U.S.C. 154(b) by 377 days.

(21) Appl. No.: 18/540,098

(22) Filed: Dec. 14, 2023

(65) Prior Publication Data

US 2024/0197962 A1 Jun. 20, 2024

Related U.S. Application Data

(60) Provisional application No. 63/387,743, filed on Dec. 16, 2022.

(51) Int. Cl.
| | |
|---|---|
| *A61L 27/52* | (2006.01) |
| *A61L 27/36* | (2006.01) |
| *A61L 27/48* | (2006.01) |

(52) U.S. Cl.
CPC ........... *A61L 27/52* (2013.01); *A61L 27/3662* (2013.01); *A61L 27/48* (2013.01); *A61L 2400/12* (2013.01); *A61L 2430/10* (2013.01)

(58) Field of Classification Search
CPC ...... A61L 27/52; A61L 27/3662; A61L 27/48; A61L 2400/12; A61L 2430/10
See application file for complete search history.

(56) References Cited

U.S. PATENT DOCUMENTS 11,111,343 B2 9/2021 Kotov et al.

OTHER PUBLICATIONS

Mredha, T.I., et al., "A Facile Method to Fabricate Anisotropic Hydrogels with Perfectly Aligned Hierarchial Fibrous Structures," Advanced Materials, 2018, 30(1704937):1-8.
Guimaraes, C.F., et al., "The stiffness of living tissues and its implications for tissue engineering," Nature Reviews Materials, 2020, 5:351-370.
Li, H., et al., "3D Interfacing between Soft Electronic Tools and Complex Biological Tissues," Advanced Materials, 2021, 33(2004425):1-17.
Matson, A., et al., "Tendon material properties vary and are interdependent among turkey hindlimb muscles," The Journal of Experimental Biology, 2012, 215(20):3552-3558.
Jung, H.-J., et al., "Role of biomechanics in the understanding of normal, injured, and healing ligaments and tendons," Sports Medicine, Arthroscopy, Rehabilitation, Therapy & Technology, 2009, 1(9):1-17.
Wang, .J.H.-C., "Mechanobiology of tendon," Journal of Biomechanics, 2006, 39:1563-1582.
Zhang, Y., et al., "Molecular insights into the complex mechanics of plant epidermal cell walls," Science, 2021, 372:1-7.
Choi, S., et al., "Anisotropic Hybrid Hydrogels with Superior Mechanical Properties Reminiscent of Tendons or Ligaments," Advanced Functional Materials, 2019, 29(1904342):1-9.
Lin, S., et al., "Muscle-like fatigue-resistant hydrogels by mechanical training," PNAS, 2019, 116(21):10244-10249.
Zou, J., et al., "Highly Efficient and Environmentally Friendly Fabrication of Robust, Programmable, and Biocompatible Anisotropic, All-Cellulose, Wrinkle-Patterned Hydrogels for Cell Alignment," Advanced Materials, 2019, 31 (1904762):1-8.
Yang, W., et al., "Highly Extensible Double-Network Gels with Self-Assembling Anisotropic Structure," Advanced Materials, 2008, 20:4499-4503.
Sun, J.-Y., et al., "Highly stretchable and tough hydrogels," Nature, 2012, 489:133-136.
Sun, T.L., et al., "Physical hydrogels composed of polyampholytes demonstrate high toughness and viscoelasticity," Nature Materials, 2013, 12:932-937.
Hua, M., et al., "Strong tough hydrogels via the synergy of freeze-casting and salting out," Nature, 2021, 590:1-13.
Guo, Y.Z., et al., "Facile preparation of cellulose hydrogel with Achilles tendon-like super strength through aligning hierarchical fibrous structure," Chemical Engineering Journal, 2022, 428(132040):1-10.
Kong, W., et al., "Muscle-Inspired Highly Anisotropic, Strong, Ion-Conductive Hydrogels," Advanced Materials, 2018, 30(1801934):1-7.
No., Y.G., et al., "High-Strength Fiber-Reinforced Composite Hydrogel Scaffolds as Biosynthetic Tendon Graft Material," ACS Biomterials Science & Engineering, 2020, 6:1887-1898.

(Continued)

*Primary Examiner* — Robert A Wax
*Assistant Examiner* — Kimberly Barber
(74) *Attorney, Agent, or Firm* — SALIWANCHIK, LLOYD & EISENSCHENK

(57) ABSTRACT

The subject invention pertains to multifunctional tendon-mimetic hydrogels constructed from anisotropic assembly of aramid nanofiber composites. The stiff nanofibers and soft polyvinyl alcohol in these anisotropic composite hydrogels (ACHs) mimic the structural interplay between aligned collagen fibers and proteoglycans in tendons. The ACHs uniquely exhibit a high modulus of ~1.1 GPa, strength of ~72 MPa, fracture toughness of 7333 $J/m^2$, and many additional characteristics matching those of natural tendons. The surfaces of ACHs can be functionalized with bioactive molecules to present biophysical cues for the modulation of morphology, phenotypes, and other behaviors of attached cells. Moreover, soft bioelectronic components can be integrated on ACHs, enabling in-situ stimulation and sensing of various physiological parameters. The outstanding mechanics and functionality of these tendon-mimetics can be advantageously applied to advanced tissue engineering, implantable prosthetics, human-machine interactions, and other technologies.

20 Claims, 56 Drawing Sheets

(56)　　　　　References Cited

OTHER PUBLICATIONS

Huang, Y., et al., "Superior fracture resistance of fiber reinfoced polyampholyte hydrogels achieved by extraordinarily large energy-dissipative process zones," Journal of Materials Chemistry A, 2019, 7:1-11.

Xu, L., et al., "Water-Rich Biomimetic Composites with Abiotic Self-Organizing Nanofiber Network," Advanced Materials, 2017, 1703343:1-6.

Hoffmeister, B.K., et al., "Ultrasonic determination of the anisotropy of Young's modulus of fixed tendon and fixed myocardium," The Journal of the Acoustical Society of America, 1996, 100(6):1-9.

Lynch, H.A., et al., "Effect of Fiber Orientation and Strain Rate on the Nonlinear Uniaxial Tensile Material Properties of Tendon," Journal of Biomechanical Engineering, 2003, 125:726-731.

Chaudhuri, O., et al., "Effects of extracellular matrix viscoelasticity on cellular behaviour," Nature, 2020, 584:535-546.

Yu, L., et al., "Ligand Diffusion Enables Force-Indepedent Cell Adhesion via Activating $\alpha 5\beta 1$ Integrin and Initiating Rac and RhoA Signaling," Advanced Materials, 2020, 32(2002566):1-12.

Saez, A., et al., "Rigidity-driven growth and migration of epithelial cells on microstructured anisotropic substrates," PNAS, 2007, 104(20):8281-8286.

Charest, J.L., et al., "Myoblast alignment and differentiation on cell culture substrates with microscale topograhy and model chemistries," Biomaterials, 2007, 28:2202-2210.

Gong, Z., et al., "Matching material and cellular timescales maximizes cell spreading on viscoelastic substrates," PNAS, 2018, 115(12):E2686-E2695.

Seo, C.H., et al., "The effect of substrate microtopography on focal adhesion maturation and actin organization via the RhoA/ROCK pathway," Biomaterials, 2011, 32:9568-9575.

Zhu, Y., et al., "Regulation of macrophage polarization through surface tophography design to facilitate implant-to-bone osteointegration," Science Advances, 2021, 7(eabf6654):1-14.

Hu, J., et al., "Mechanically active adhesive and immune regulative dressings for wound closure," Matter, 2021, 4:1-29.

Mcwhorter, F.Y., et al., "Modulation of macrophage phenotype by cell shape," PNAS, 2013, 110(43):17253-17258.

Fan, J.A., et al., "Fractal design concepts for stretchable electronics," Nature Communications, 2014, 5(3266):1-8.

Xu, L., et al., "3D multifunctional integumentary membranes for spatiotemporal cardiac measurements and stimulation across the entire epicardium," Nature Communications, 2014, 5(3329):1-10.

Koo, J., et al., "Wireless bioresorbable electronic system enables sustained nonpharmacological neuroregenerative therapy," Nature Medicine, 2018, 24:1-12.

Yu, L., et al., "High-Antifouling Polymer Brush Coatings on Non-polar Surfaces via Adsorption-Cross-Linking Strategy," ACS Applied Materials & Interfaces, 2017, 9:44281-44292.

Vergari, C., et al., "Axial speed of sound is related to tendon's nonlinear elasticity," Journal of Biomechanics, 2012, 45:263-268.

Purslow, P.P., et al., "Collagen Orientation and Molecular Spacing During Creep and Stress-Relaxation in Soft Connective Tissues," The Journal of Experimental Biology, 1998, 201:135-142.

Quapp, K.M., et al., "Material Characterization of Human Medial Collateral Ligament," Journal of Biomedical Engineering, 1998, 120:757-763.

Wren, T.A.L., et al., "Mechanical properties of the human achilles tendon," Clinical Biomechanics, 2001, 16:245-251.

Johnson, G.A., et al., "Tensile and Viscoelastic Properties of Human Patellar Tendon," Journal of Orthopaedic Research, 1994, 12(6):796-803.

Random network    Stretching    Confined drying    Re-swelling
(Isotropic)

Isotropic

Oriented

☐ Unipolar electrode   ☐ Bipolar electrodes   ☐ Temperature sensor

ANF in DMSO          PVA in DMSO          Intermixing          ANF-PVA

Isotropic ANF-PVA          Stretching          Length-fixed drying          Reswelling Isotropic ANF-PVA

ACH-80 contact electrode temperature sensor bipolar electrode unipolar electrode contact electrode temperature sensor unipolar electrode bipolar electrodes

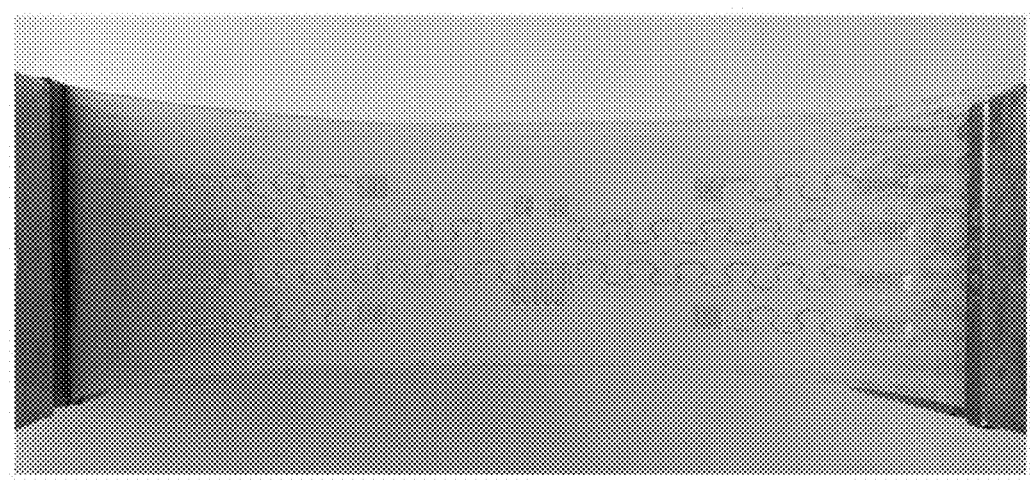
50%
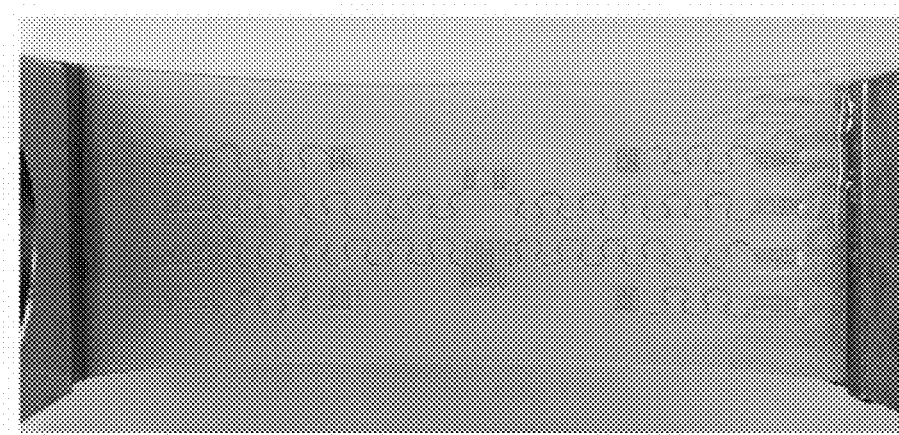
30%
FIG. 25
0%

TENDON-MIMETIC MATERIALS WITH ANISOTROPIC ASSEMBLY OF ARAMID NANOFIBERS

CROSS-REFERENCE TO RELATED APPLICATION

The present application claims the benefit of U.S. Provisional Application Ser. No. 63/387,743, filed Dec. 16, 2022, which is hereby incorporated by reference herein in its entirety, including any figures, tables, or drawings.

BACKGROUND OF THE INVENTION

Reconciling the mismatches between natural biological tissues and engineering materials represents a critical demand for the development of advanced biomedical devices and tissue engineering platforms.[1,2] However, natural tissues exhibit many characteristics that are difficult to replicate with synthetic materials. For instance, tendons involve hierarchical organization of aligned collagen fibers interlaced with soft water-retaining biopolymers. They contain ~60 wt. % of water while exhibiting high moduli and strengths in the range of 55-120 MPa.[3,4] The anisotropic structures of tendons not only enable essential load-bearing capabilities for the musculoskeletal system, but also provide important biophysical cues that translate into the behaviors of cells through interfacial interactions.[5]

Over the past decade, extensive research efforts were devoted to the engineering of tendon-mimetic materials with high structural anisotropy. For instance, tensile stress was exploited for the orientation of polymer networks, leading to hydrogels with enhanced mechanical strength along the stretched direction.[6-9] Multiple networks or physical cross-linking were incorporated into hydrogels for the improvement of fracture toughness.[10-12] Phase separation induced by freezing and salting-out was recently explored to generate hierarchical structures, further improving the mechanics of hydrogels.[13] However, the moduli of these anisotropic hydrogels are still orders of magnitude lower than that of the natural tendon, partly due to the flexibility of hydrophilic polymer chains in the presence of water. Incorporating bundled fibers from cellulose[14,15] or synthetic polymers[16,17] can confer high stiffness to the hydrogel composites. However, it is challenging to control the interactions between the stiff fibers and soft matrix to emulate the microstructural interplay in load-bearing soft tissues. Therefore, many mechanical behaviors of the natural tendons, such as strain-stiffening and viscoelastic responses, remain difficult to replicate with fiber-reinforced hydrogels. Furthermore, previous efforts on tendon-mimetic materials mostly focused on the engineering of mechanical properties. Limited attention was paid to the functionalization of materials that enables bioactive interfaces with cells and tissues, therefore limiting their potential for biomedical applications.

BRIEF SUMMARY OF THE INVENTION

Embodiments of the subject invention provide a materials platform for the construction of hybrid anisotropic hydrogels with tendon-like or soft-tissue-like behaviors and multifunctionality for bio-interfaces. In certain embodiments, reconfigurable interactions between stiff aramid nanofibers (ANFs) and flexible polyvinyl alcohol (PVA) allow assembly of highly oriented networks that emulate the microstructural interplay between aligned collagen fibers and soft proteoglycans in native tissues. The resulting anisotropic composite hydrogels (ACHs) exhibit high mechanical properties matching those of the natural tendons while retaining a similar water content of ~60%. Embodiments provide biofunctionalization of ACHs, providing anisotropic biophysical cues for the modulation of cell behaviors. Soft bioelectronics are further integrated on ACHs, enabling hybrid devices capable of in-situ sensing and stimulation. The mechanics and functionality of these tendon-mimetics provide opportunities for their application in advanced biomedical technologies.

Embodiments provide multifunctional hydrogel materials that replicate the mechanical properties of natural tendons. Methods are provided for anisotropic assembly of aramid nanofiber composites, leading to high stiffness, toughness, water content, and many other characteristics matching those of the natural tissue. The materials can be further functionalized with bioactive molecules to control interactions with cells. Microfabricated stretchable electronics can be integrated onto these materials, providing capabilities in biosensing and stimulation. The outstanding mechanics and functionality of these materials are advantageously applied to tissue repair, stem cell technologies, implantable devices, and other applications.

Mimicking natural load-bearing soft tissues with synthetic materials is difficult due to the limited materials toolbox for biomimetic designs. Embodiments provide enhanced materials and methods that enable advanced biomaterials and devices for tissue repair, cell therapies, implantable devices, and other medical needs. Embodiments provide systems and methods to fabricate anisotropic nanofiber hydrogels based on ANFs and PVA. The interactions between the materials constituents in a highly oriented network mimic the interplay between collagen and proteoglycans in the natural tissues, leading to outstanding physical properties. In certain embodiments the surface of the synthetic hydrogels are also functionalized for cell-interactions and bioelectronic sensing. Embodiments provide beneficial new products, related processes, and compositions. Embodiments advantageously apply the use of aramid nanofiber composites to construct anisotropic hydrogels, which can mimic the properties of natural tendons or ligaments.

Embodiments advantageously provide functionalization of the hydrogels surfaces with bioactive molecules and printed bioelectronic devices. Certain embodiments are advantageously well suited to practical applications in healthcare and wearable systems. Embodiments provide novel and advantageous approaches to generating anisotropic composite hydrogels with tissue-mimetic characteristics and multifunctionality for biomedical applications, including novel design in the materials composition and fabrication process that allows the creation of tendon-mimetic hydrogels. Embodiments provide unique mechanical properties and multifunctionality that have not been achieve by previous materials.

Embodiments provide unique compositions and microstructural configurations of materials to achieve tendon-mimetic properties, and functionalization methods for such materials. The resulting materials have unique mechanical properties and multifunctionality that have not been achieved by related art materials.

Embodiments provide anisotropic assembly of nanofiber composites to construct tendon-mimetic hydrogels, showing outstanding mechanical properties and multifunctionality for interfacing with cells and tissues.

BRIEF DESCRIPTION OF THE DRAWINGS

according to an embodiment of the subject invention. (FIG. 1A) Chemical structures of aramid nanofiber (ANF) and polyvinyl alcohol (PVA), and their intermolecular hydrogen bonding. (FIG. 1B) Schematics of the processing steps for ACH involving stretching and confined drying for the orientation of nanofiber assembly. (FIG. 1C) Scanning electron microscope (SEM) images of isotropic ANF-PVA hydrogel (top) and ACH-80 (bottom), scale bar: 1 μm. (FIG. 1D) Schematics of the multifunctional tendon-mimetic ACHs.

(FIG. 2A, FIG. 2B) Tensile stress-strain curves of ACHs in the directions parallel (FIG. 2A) and perpendicular (FIG. 2B) to the primary fiber orientation direction, respectively, as compared with the responses of isotropic ANF-PVA hydrogels. The sample denoted as ACH-x corresponds to x % of imposed elongation during the pre-stretching-drying process. (e.g., ACH-80 denotes an embodiment that is pre-stretched and elongated by 80% during drying; ACH-60 denotes an embodiment that is pre-stretched and elongated by 60% during drying; and ACH-40 denotes an embodiment that is pre-stretched and elongated by 40% during drying.) (FIG. 2C) The stiffness anisotropy of ACHs, as characterized by the ratio between initial tensile moduli parallel (Ep) and perpendicular/normal (En) to the fiber alignment. (FIG. 2D) Moduli and strengths of ACH-80 and ACH-60 as compared with those of natural tendons, ligaments, and other anisotropic hydrogels with tendon-mimetic characteristics (data provided in Table 2). (FIG. 2E) Fracture energies of ACHs measured in the directions parallel and perpendicular to the fiber alignment, as compared with those of isotropic ANF-PVA hydrogels. (FIG. 2F) Cyclic tensile tests on ACH-80 in the direction parallel to the fiber alignment, with 7.5% of maximum imposed strain.

(FIG. 3A) Fluorescence images of F-actin in NIH-3T3 fibroblasts cultured on various substrates (top), and the corresponding angular distribution of cell orientation (bottom) (n≥30). Zero angle (0°) represents the direction parallel to the fiber alignment. Scale bar: 100 μm. (FIG. 3B) Atomic force microscope (AFM) images showing the surface topography of biofunctionalized ACH-80 (bottom) and isotropic ANF-PVA hydrogel (top). Scale bar: 1 μm. (FIG. 3C) Fluorescence images of RAW 264.7 macrophages cultured on isotropic ANF-PVA hydrogel (left) and ACH-80 (middle), immunostained for M2 biomarker Arg-1, and statistics of the mean fluorescent intensity (MFI) of individual cells showing the differences induced by distinct substrates (right). The cell cultures were treated with IL4 and IL13 to induce M2 phenotype. Scale bar: 50 μm. (FIG. 3D) Immunostaining for iNOS (M1 biomarker) in RAW 264.7 showing the distinct effects induced by isotropic ANF-PVA (left) and ACH-80 (right), also characterized by MFI statistics (right). IFNγ and LPS were used to induce M1 phenotype. Scale bar: 50 μm. n=30, **** P<0.0001. All white arrows indicate the direction parallel to the fiber alignment.

(FIG. 4A) Photographs of serpentine electronics transfer-printed onto an isotropic ANF-PVA hydrogel (top) and their stretched state with the processed ACH (bottom). The insets show various functional components. Scale bar: 2 cm. (FIG. 4B) Finite element analysis (FEA) model (left) and microscope image (right) of a representative serpentine device bonded with isotropic ANF-PVA hydrogel. Scale bar: 1 mm. (FIG. 4C) FEA simulation on the stress distribution in the serpentine device under 50% elongation imposed to the hybrid structure. (FIGS. 4D-4E) Electrocardiogram (ECG) (FIG. 4D) and electromyogram (EMG) (FIG. 4E) measured with bioelectrodes on a hybrid ACH. (FIG. 4F) Temperature variation in a water bath characterized with a temperature sensor on a hybrid ACH. (FIG. 4G) Schematics and the resistance response to tensile strain for an ionically conductive ACH sample. (FIGS. 4H-4I) Responses of an ACH-based strain sensor mounted on a finger under various amplitudes of deformation (FIG. 4H) and cyclic motion (FIG. 4I).

(FIG. 5A) Photographs of the materials components showing the processing for ANF-PVA hydrogels. (FIG. 5B) Photographs of an ACH during various processing steps.

(FIG. 7, left panel) Lower magnification. (FIG. 7, right panels) Magnified details corresponding to the layers shown in (FIG. 7, left panel). The microstructures appeared consistent across the entire thickness of the sample. The arrows indicate the direction of pre-stretching. Scale bar: 2 μm.

(FIG. 8A) Isotropic ANF-PVA. (FIG. 8B) ACH-40. (FIG. 8C) ACH-60. (FIG. 8D) ACH-80. The degree of fiber alignment and bundling in ACHs increase with increasing elongation during the pre-stretching-drying processing. Scale bar: 100 nm.

(FIG. 10A) ACH-40, (FIG. 10B) ACH-60 and (FIG. 10C) ACH-80. Similar to those in natural tendons, the maximum tangent moduli occur in the "linear region", corresponding to critical load-bearing capabilities 1.2. The red line indicates linear fits for the linear regions to determine the elastic moduli of ACHs.

(FIG. 11A) The tensile stress-strain responses shown with full range of the applied strain until fracture of the samples. (FIG. 11B) Tangent modulus as determined by the first order derivative of the stress-strain curve. Strain-stiffening behaviors were observed in ACHs.

(FIG. 12A) Comparison of mechanical properties between ACH-80 and an isotropic ANF-PVA hydrogel with enhanced solid content. Both hydrogels have a water content of 60%. (FIG. 12B) Comparison of mechanical properties of 80%-stretched samples dried with various time duration (5 h, 10 h and 20 h). The samples were immersed in DI water for 24 h to achieve equilibrium water content before the measurements.

(FIG. 13A) Photograph of a sample during a tearing test. (FIG. 13B-FIG. 13D) Force-extension curves and the corresponding fracture energies of isotropic ANF-PVA hydrogel (FIG. 13B), and ACH-80 measured in directions parallel (FIG. 13C) and perpendicular (FIG. 13D) to the fiber alignment.

(FIG. 14A) Isotropic ANF-PVA hydrogel. (FIG. 14B-FIG. 14C) ACH-40 in the directions parallel (FIG. 14B) and perpendicular (FIG. 14C) to the fiber alignment. (FIG. 14D) ACH-80 in the direction perpendicular to the fiber alignment.

(FIG. 16A) Chemical structures. (FIG. 16B-FIG. 16C) Confocal images of NIH3T3 fibroblasts cultured on ANF-PVA hydrogels with (FIG. 16B) and without (FIG. 16C) surface functionalization, indicating good attachment of cells on surface-functionalized samples. Scale bar: 100 μm.

(FIG. 17A) Calibration curve of optical absorbance versus cell number. (FIG. 17B) Proliferation of NIH3T3 fibroblasts cultured on ACH-80 as compared with those cultured on a petri dish.

(FIG. 20A) Fluorescent images of fibroblasts treated with various concentrations of Y-27632, showing the inhibition of cell orientation. Scale bar: 100 μm. (FIG. 20B) Quantitative analysis of cell orientational order parameter S in correlation with the concentration of Y-27632 (n=30, *P<0.05,  P<0.01, * P<0.001, **** P<0.0001). Orientation index (S) was determined by S=cos(2θ).

(FIG. 21A-FIG. 21B) Florescent images of macrophages cultured on isotropic ANF-PVA hydrogel (FIG. 21A), and ACH-80 (FIG. 21B). Scale bar: 50 μm. (FIG. 21C) Statistics of macrophage orientational order parameter S (n=30).

(FIG. 24A) An array of sensors fabricated on a 4-inch silicon wafer. (FIG. 24B) Optical microscope images showing the components of the device. (Scale bar: 1 mm.)

FIG. 25 illustrates uniaxial stretching for the processing of an electronics-integrated ACH according to an embodiment of the subject invention. There was no interfacial delamination or mechanical damage to the electronic components during the process, owing to the high stretchability of serpentine designs.

(FIG. 26A) Electrical impedance between the microfabricated electrode and the skin as a function of frequency. (FIG. 26B) Change in resistance as a function of temperature, showing linear responses of the temperature sensor.

Table 1. shows there was no major change in the length of the ACH-80 sample, indicating permanent alignment of the fibrillar network. While not being bound by theory, the inventors hypothesize that the minor variation in the length after removing the stretching could be related to the entropic reconfiguration of PVA chains, leading to crimping of the fibers. In contrast, the significant changes in cross-section area (CSA) indicate the variation of water content during the processes.

TABLE 1

| | | | | |
|---|---|---|---|---|
| | Changes in length and cross-section area (CSA) of ACH-80 during confined drying and reswelling. | | | |
| Dimensions | Before drying (confined) | After drying (confined) | Before re-swelling (released) | After re-swelling |
| Length | 36.3 ± 0.4 mm | 36.3 ± 0.4 mm | 31.8 ± 0.5 mm | 32.0 ± 0.4 mm |
| CSA | 4.75 ± 0.31 mm$^2$ | 0.62 ± 0.08 mm$^2$ | 0.72 ± 0.10 mm$^2$ | 1.63 ± 0.11 mm$^2$ |

TABLE 2

Mechanical properties of ACHs in comparison with other synthetic
anisotropic hydrogels and natural biological tissues.

| Sample name | Elastic modulus (MPa) | Ultimate Strength (MPa) | Reference |
|---|---|---|---|
| ACH-80 | 1114.0 | 72.1 | Embodiment of the subject invention |
| ACH-60 | 490.1 | 52.6 | Embodiment of the subject invention |
| FAS-PVA (freezing-assisted salting-out PVA) | 2.5 | 23.5 | 4 |
| MT-PVA (mechanically trained PVA) | 0.2 | 5.2 | 5 |
| DC-cellulose (dual crosslinked cellulose) | 12.2 | 7.9 | 6 |
| UD-PBDT-PAAM (uniaxially diffused poly (2,20-disulfonyl-4,40-benzidine terephthalamide) - polyacrylamide) | 0.009 | 0.5 | 7 |
| D-cellulose-PAM (delignified cellulose-polyacrylamide) | 310 | 36 | 8 |
| DCC-alginate (drying in confined condition alginate) | 342 | 53 | 9 |
| DCC-cellulose | 367 | 19 | 9 |
| MC-ligament (Medial collateral ligament) | 332 | 39 | 10 |
| AC-ligament (Anterior cruciate ligament) | 447 | 46 | 11 |
| PC-ligament (Posterior cruciate Ligament) | 447 | 36 | 11 |
| Achilles' tendon | 819 | 79 | 12 |
| Patellar tendon | 660 | 64.7 | 13 |
| EDL tendon (Extensor digitorum longus tendon) | 1072 | 68.2 | 14 |
| FPD3 tendon (Flexor perforans digiti 3 tendon) | 948 | 66.8 | 14 |

DETAILED DISCLOSURE OF THE INVENTION

Figure 1A:
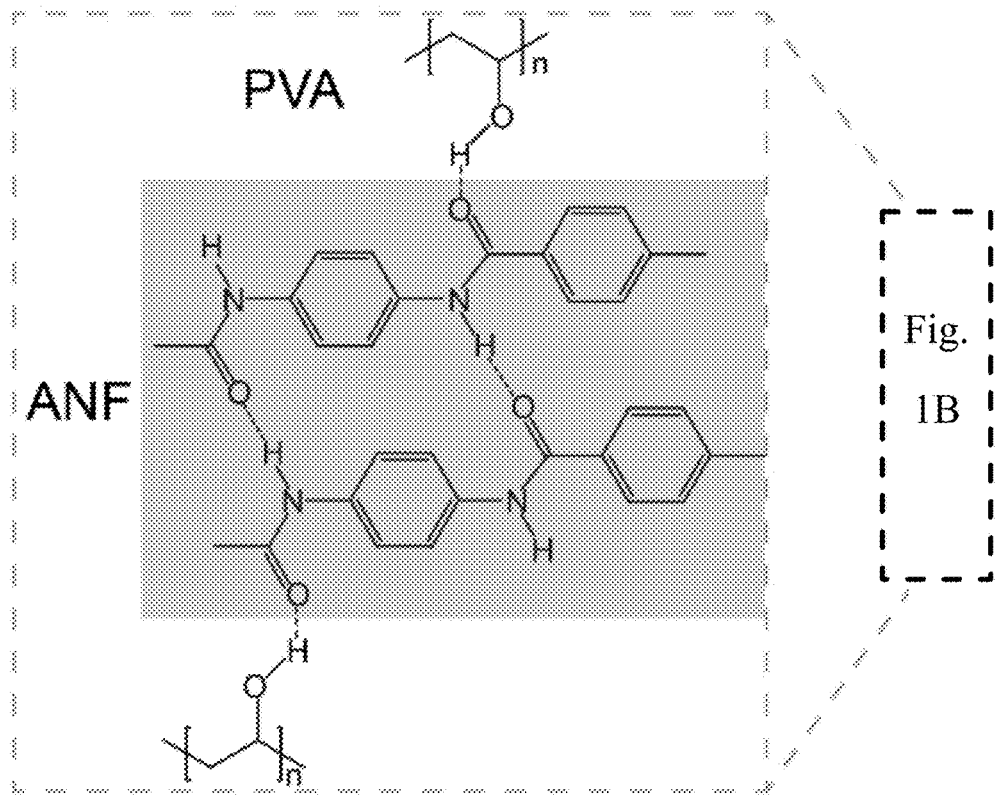
FIGS. 1A-1D illustrate the design and processing of tendon-mimetic anisotropic composite hydrogels (ACHs)
Figure 1B:
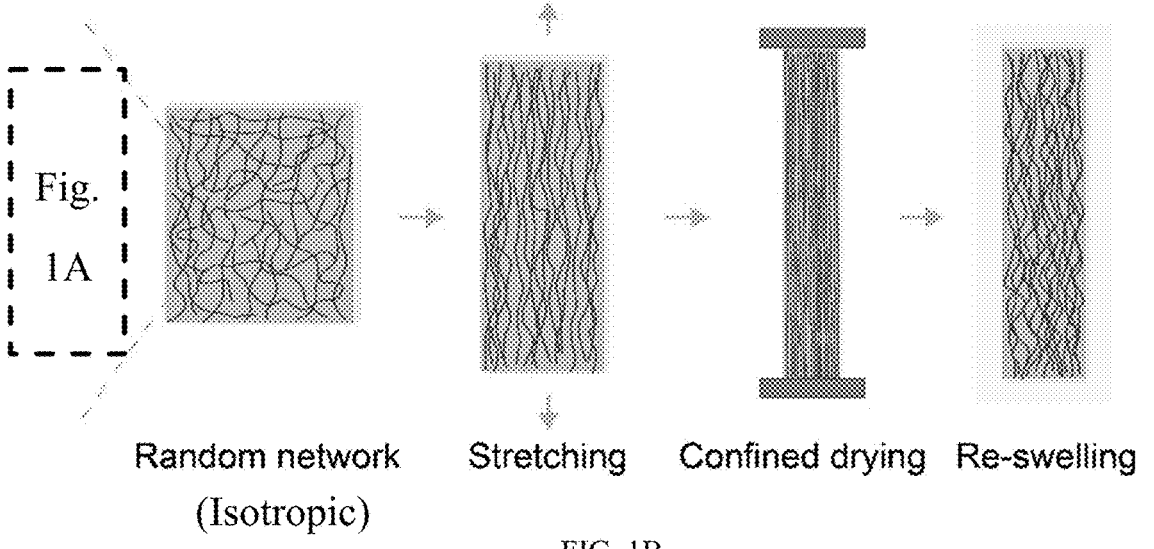
Figure 1C:
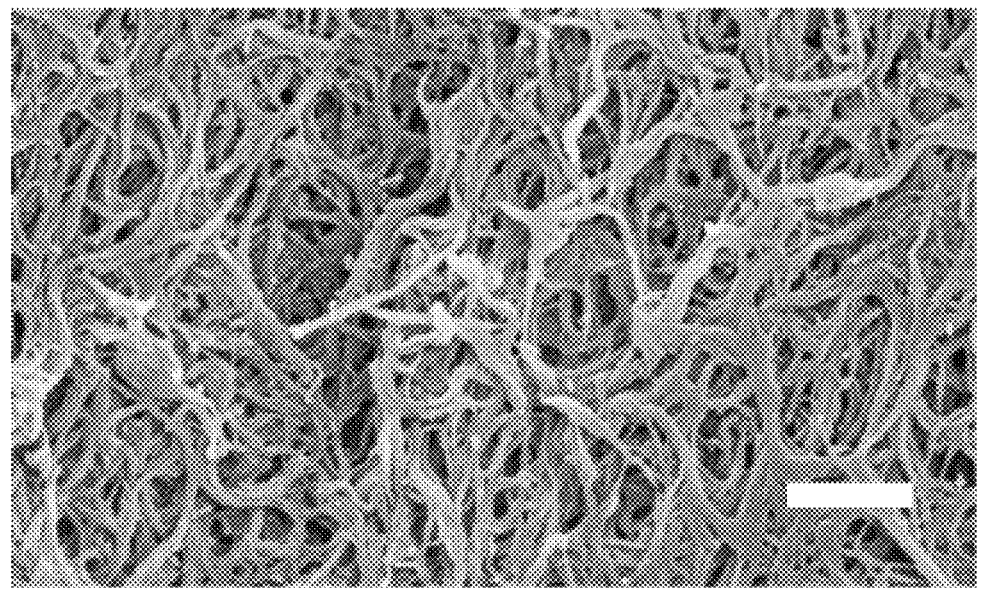
Figure 1C:
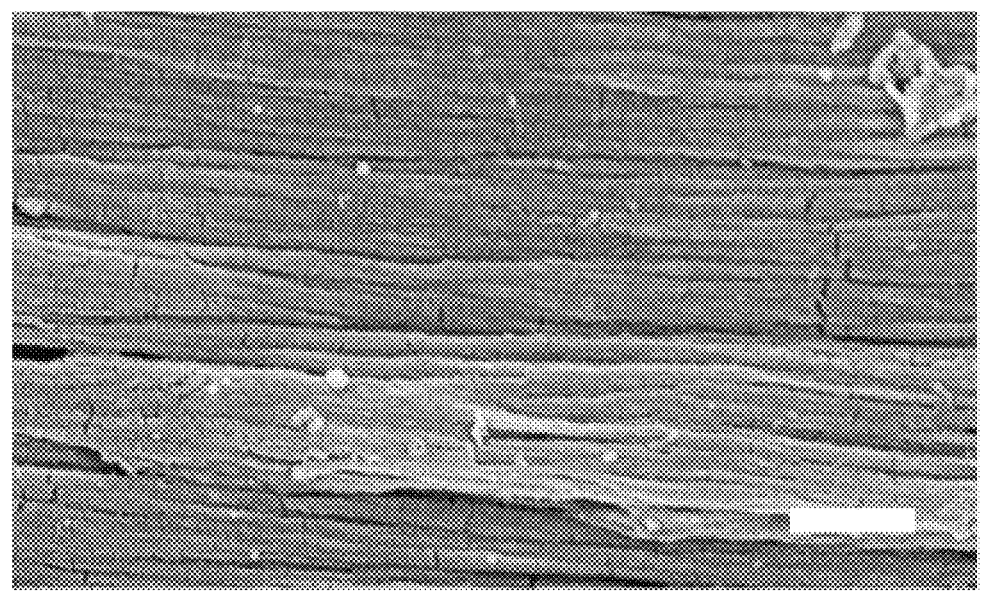
Figure 1D:
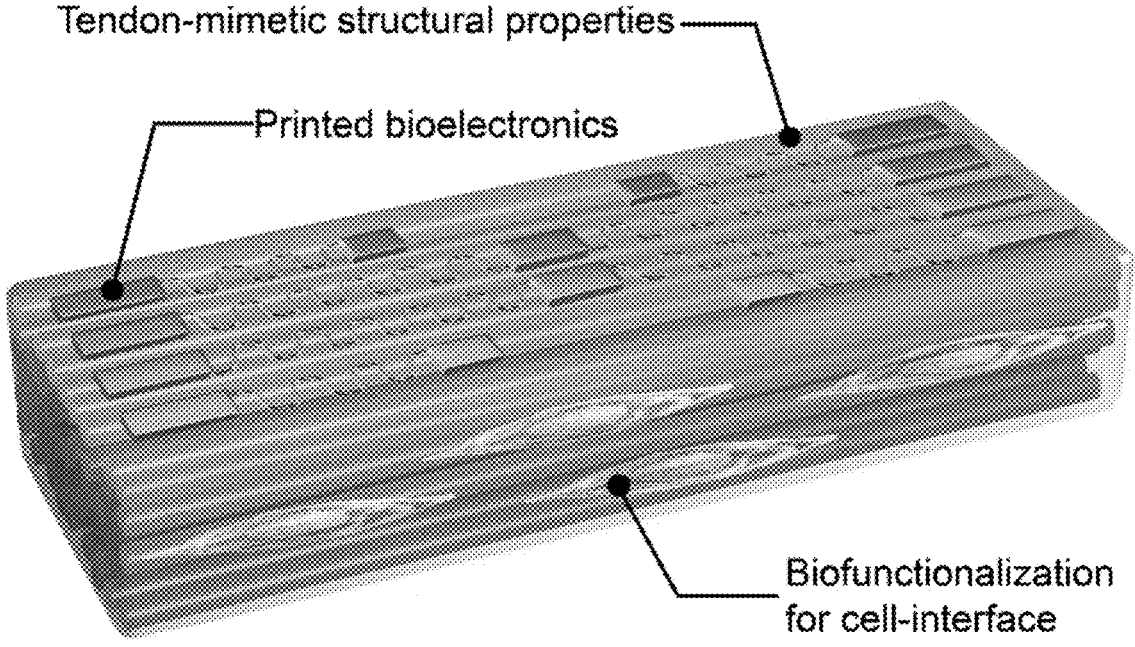
Figure 5A:
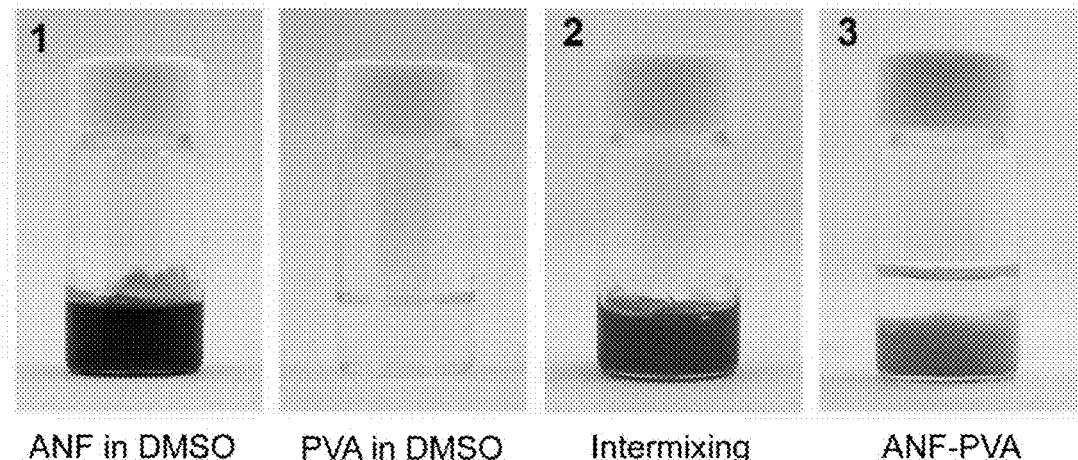
FIGS. 5A-5B illustrate a fabrication processes for ACHs according to an embodiment of the subject invention.
Figure 5B:
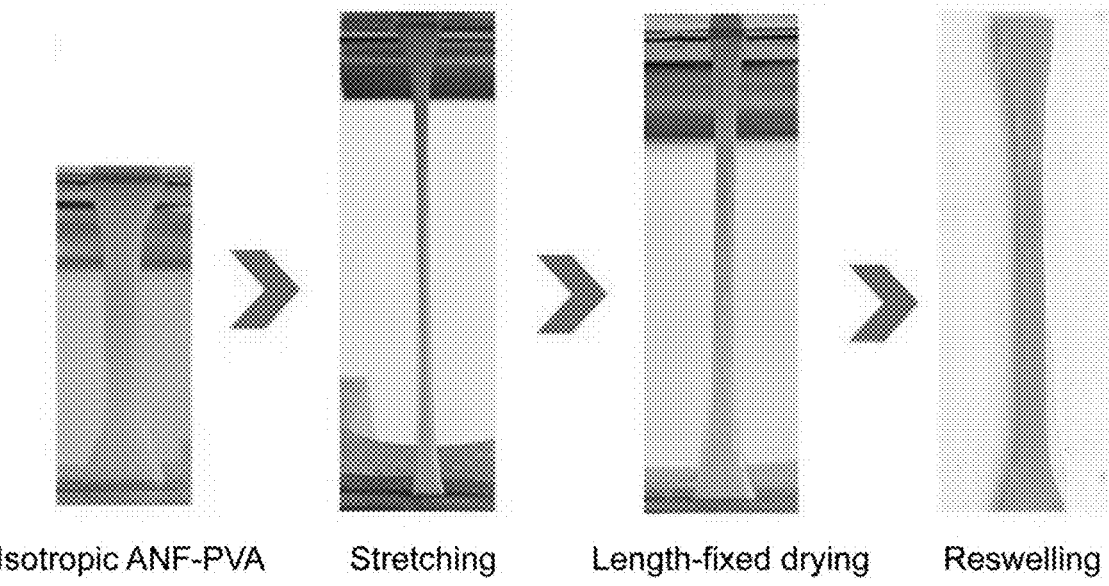
Figure 6:
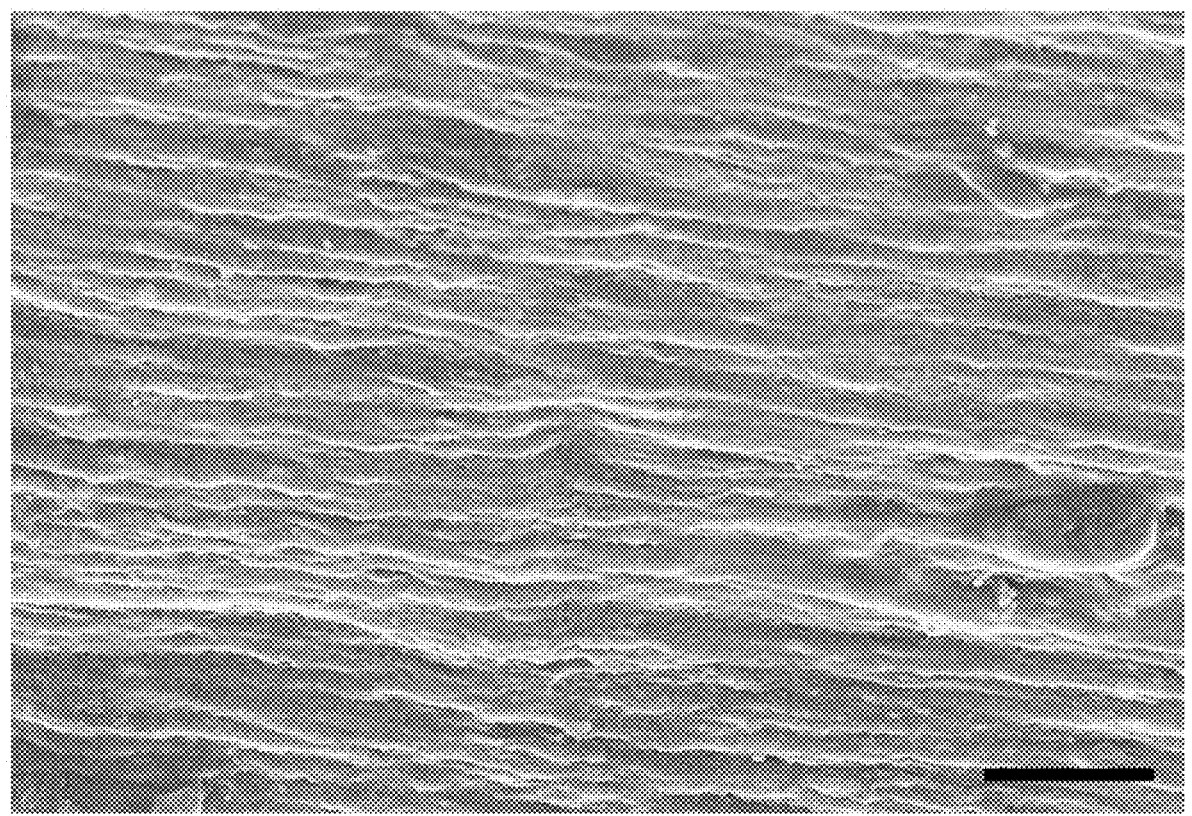
FIG. 6 is a SEM image of ACH-80 according to an embodiment of the subject invention. Fiber bundling and crimping can be observed from the microstructural examination. Scale bar: 2 μm.
Figure 7:
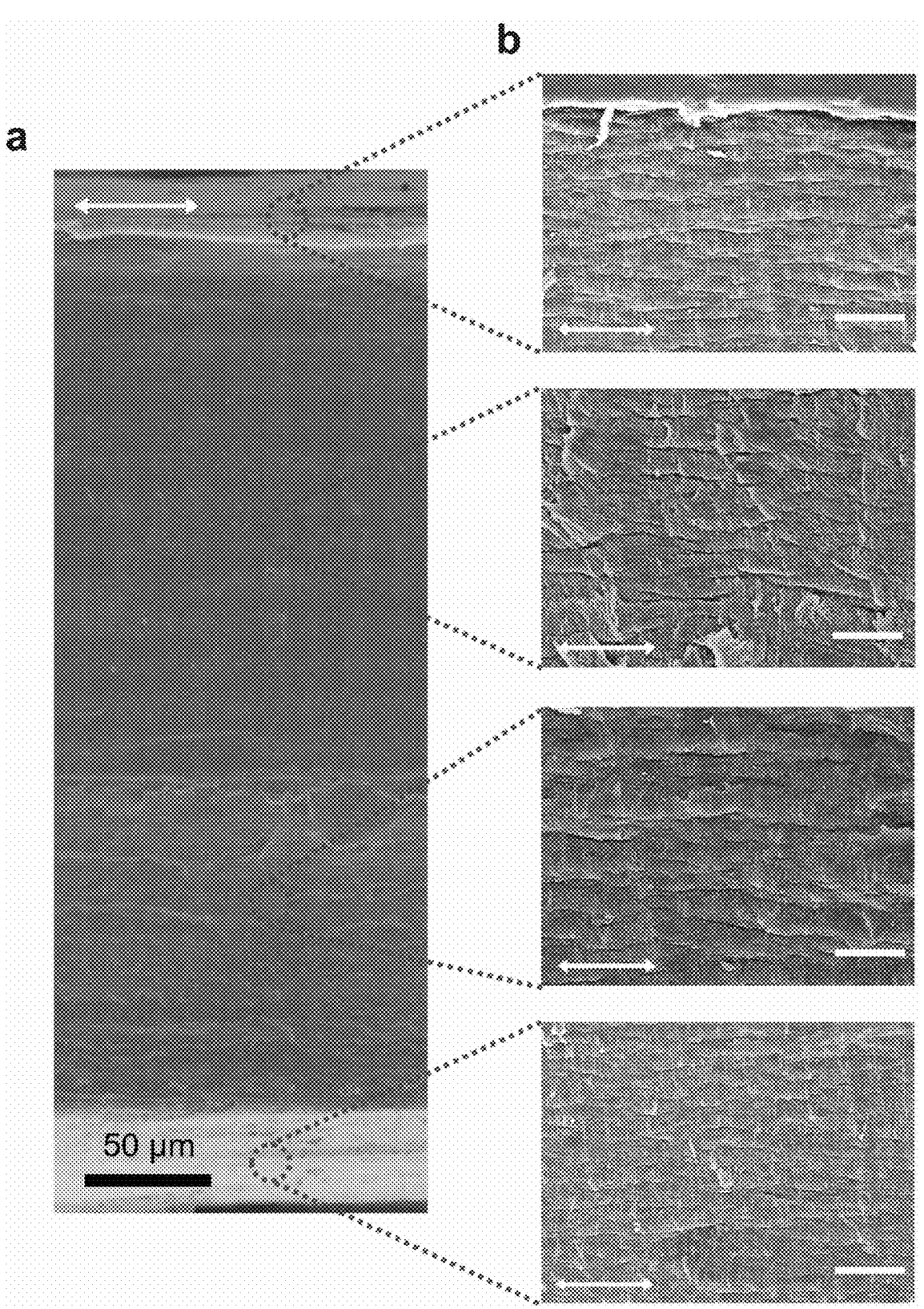
FIG. 7 illustrates results of SEM examination on the longitudinal section of ACH-80 according to an embodiment of the subject invention.
Figure 8A:
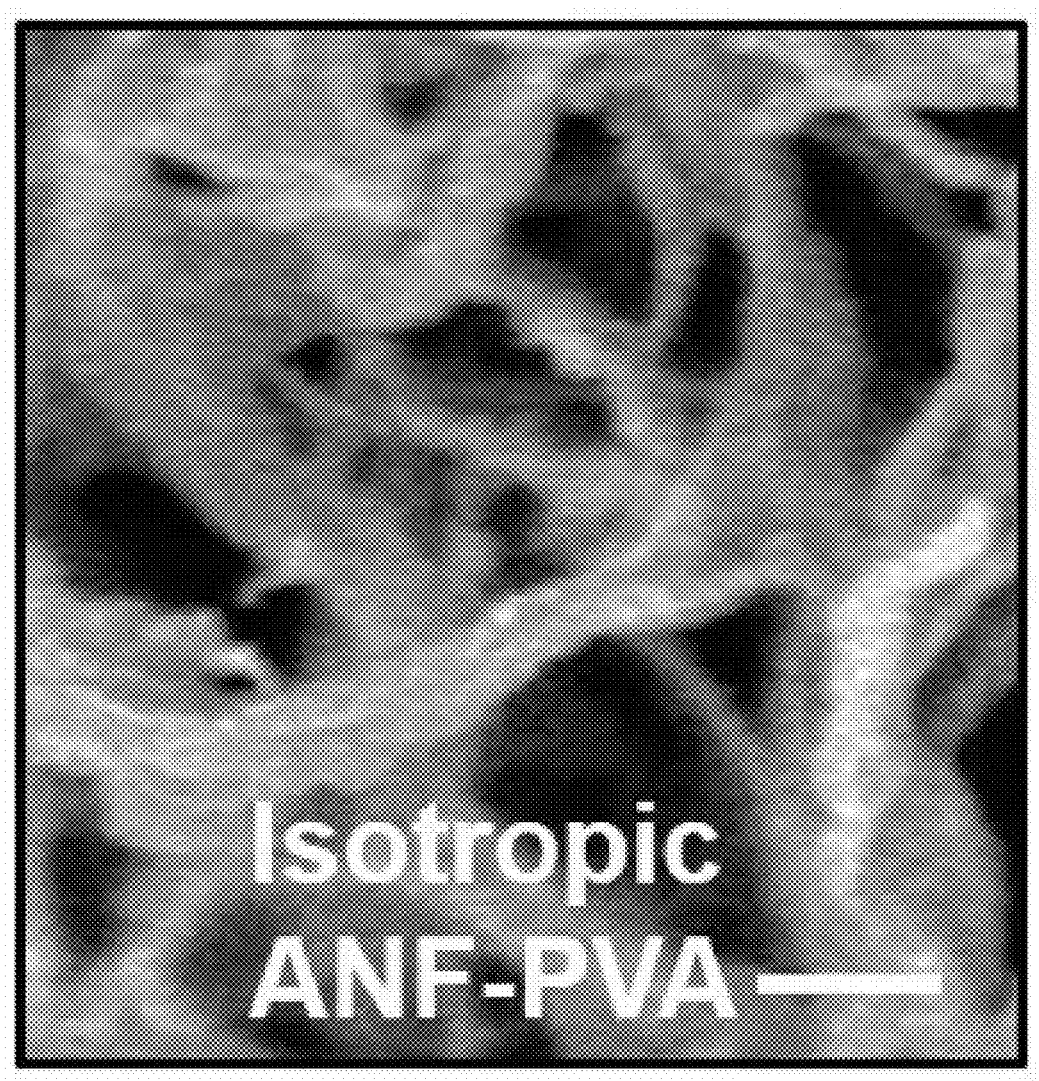
FIGS. 8A-8D are SEM images of ACHs with various pre-stretching ratios according to certain embodiments of the subject invention.
Figure 8B:
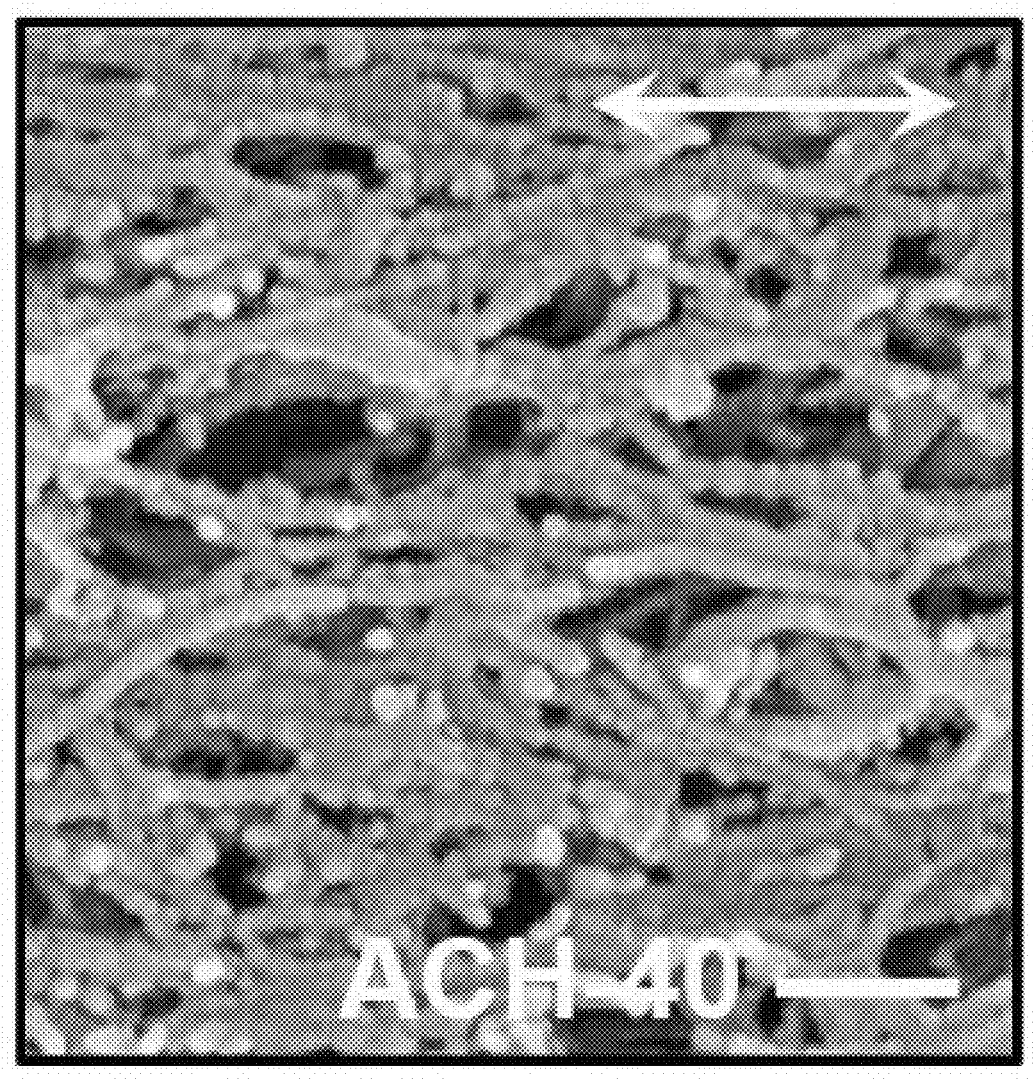
Figure 8C:
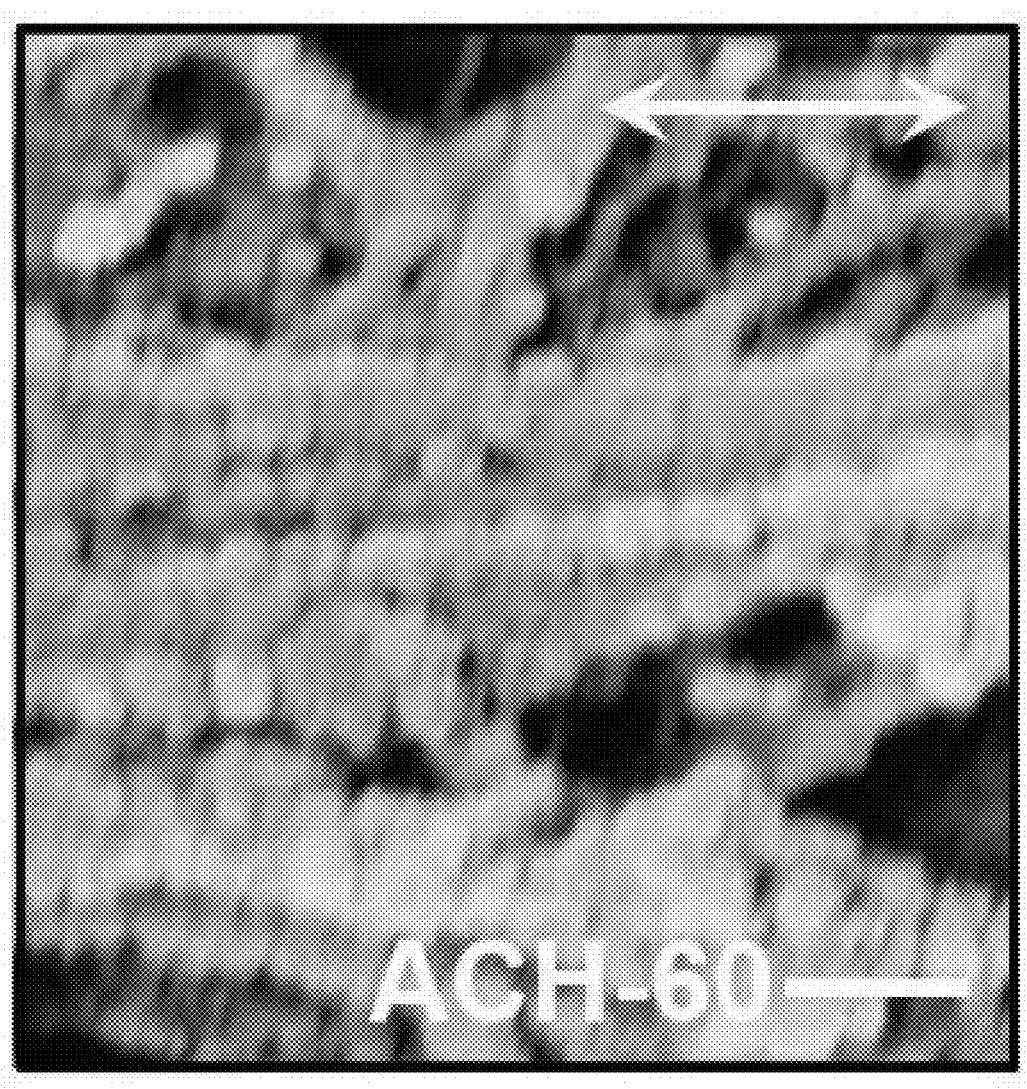
Figure 8D:
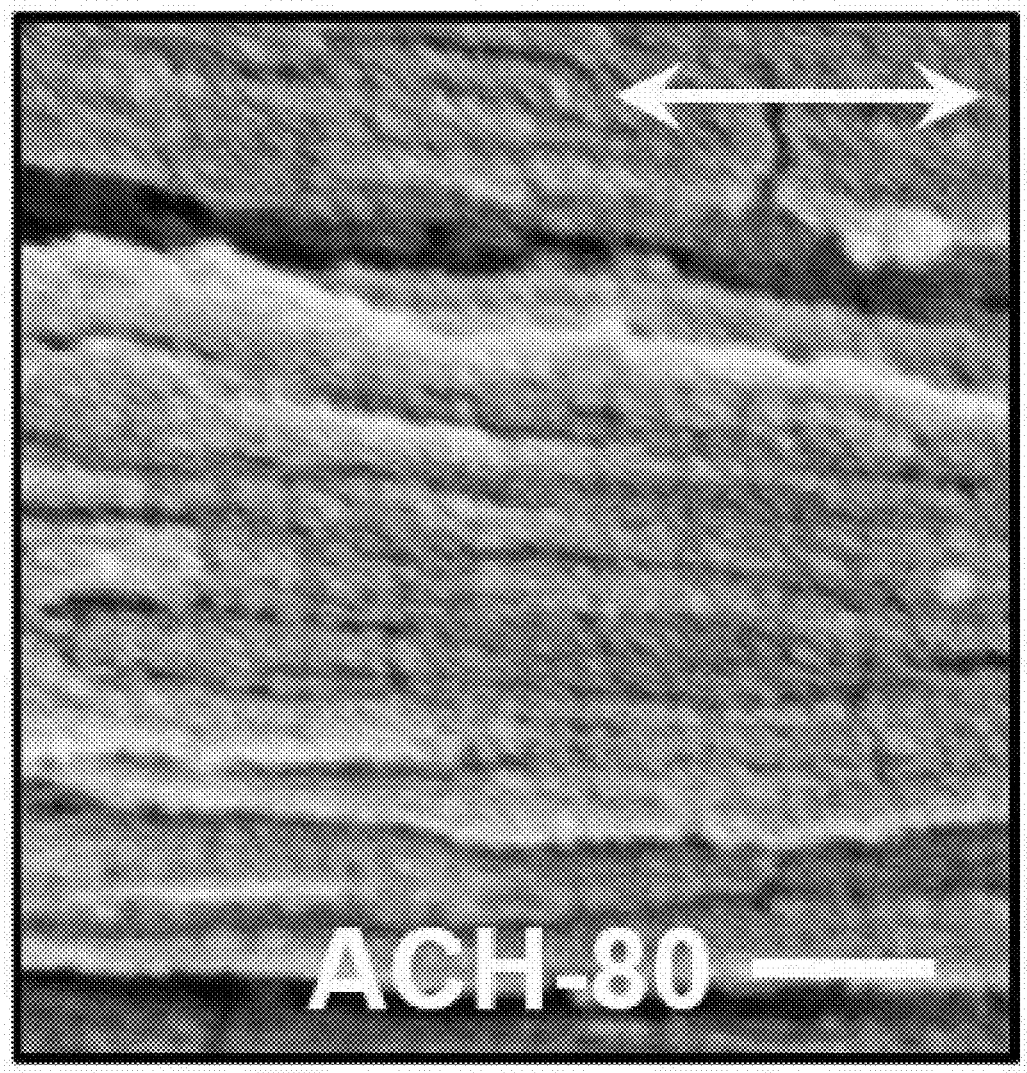

Embodiments of the subject invention provide systems and methods for fabrication of anisotropic composite hydrogels (ACHs) that involve stretching and confined drying applied to isotropic hydrogels consisting of stiff aramid nanofibers (ANFs) and flexible polyvinyl alcohol (PVA). The provided ANFs exhibit branched microstructures with fiber diameters of 5-30 nm and lengths of 3-10 μm, providing collagen-mimetic building blocks for the composites. 18 Extensive hydrogen bonding between ANFs and PVA confers reconfigurability of the 3D network combined with high toughness (FIG. 1A). In an embodiment, under uniaxial tension, the fibrillar network orients along the direction of stretching without structural disintegration even under 80% of strain (FIG. 1B and FIGS. 5A-5B). Next, the hydrogel sample is dried in a controlled atmosphere (e.g., about 50% in humidity) with their length fixed in the direction of stretching (Table 1). This fixed length drying step facilitates interfibrillar interactions under the confined configuration, leading to permanent alignment of the fibrillar network.[19] Re-swelling the samples in aqueous media provides ACHs with an equilibrium water content of about 60-74%, a similar weight fraction of water in the composite when compared to natural tendons. Scanning electron microscopy (SEM) images confirmed the highly oriented fibrillar network of ACH in contrast with that of isotropic ANF-PVA hydrogels (FIG. 1C). In addition, bundling and crimping of fibers were observed in ACH, resembling the hierarchical structures in natural tendons (FIG. 6). The anisotropic microstructures appeared consistent across the entire depth of millimeter-scale samples (FIG. 7), leading to robust mechanical behaviors of ACHs. Moreover, the PVA chains afford further chemical functionalization, enabling bioactive interfaces for cells or integration with multifunctional bioelectronic devices (FIG. 1D).

Figure 2A:
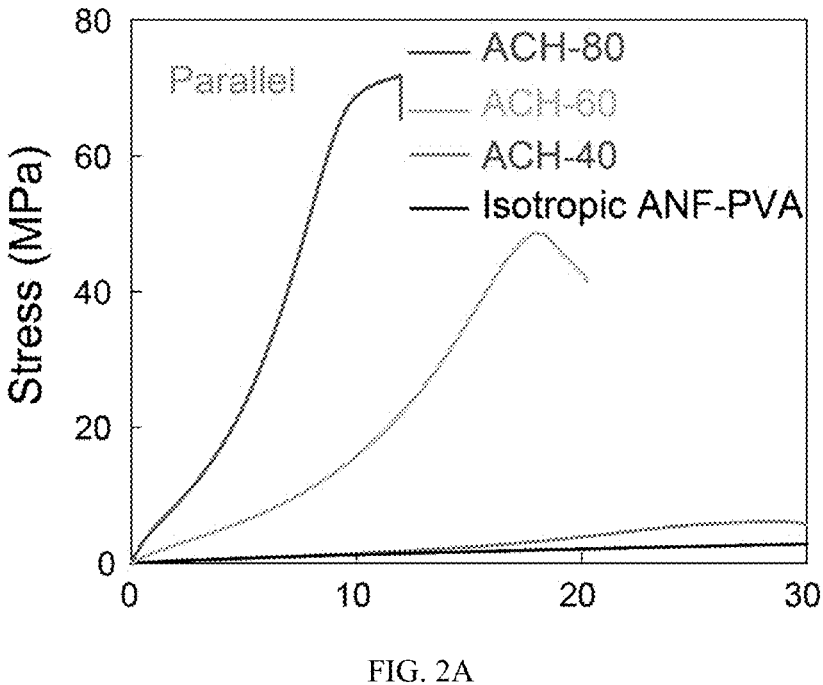
FIGS. 2A-2F are charts illustrating the mechanics of ACHs according to certain embodiments of the subject invention.
Figure 2B:
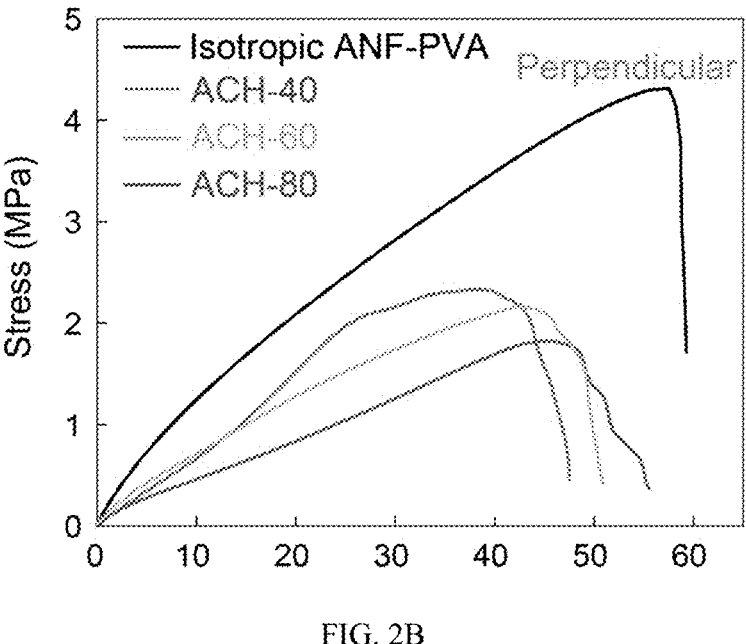
Figure 2C:
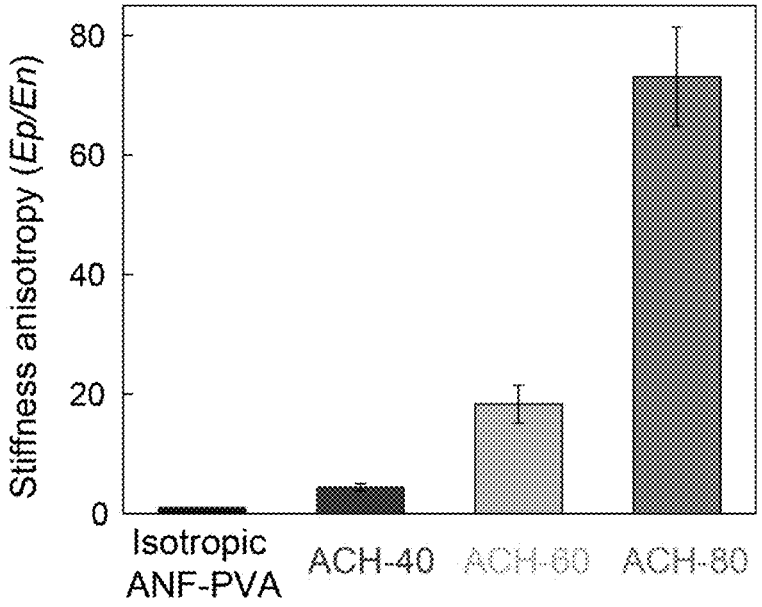
Figure 2D:
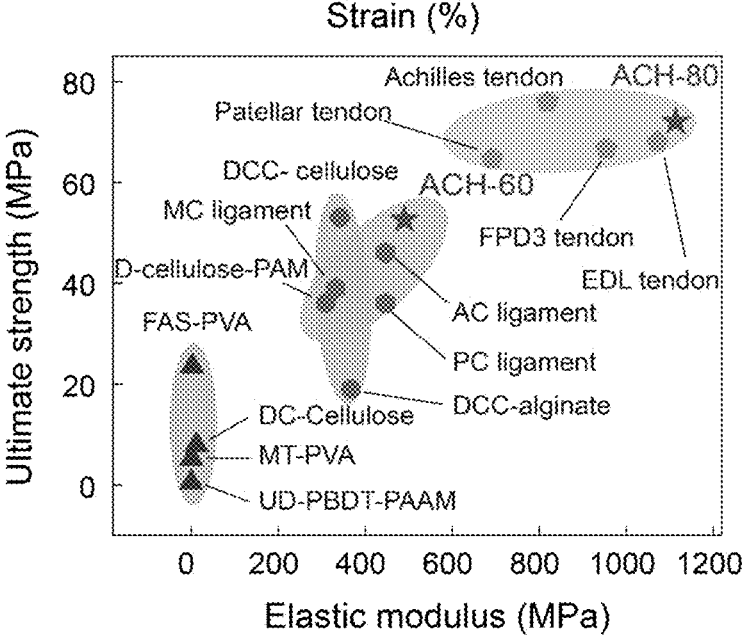
Figure 2E:
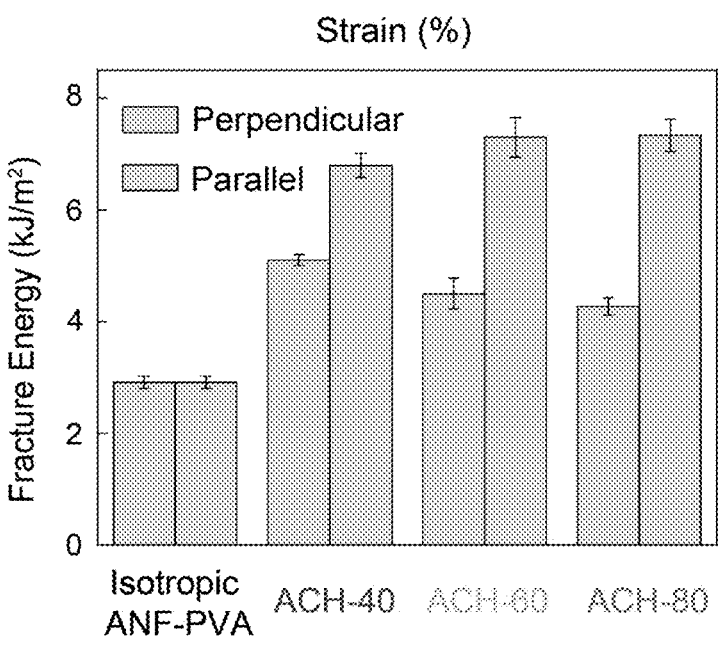
Figure 9:
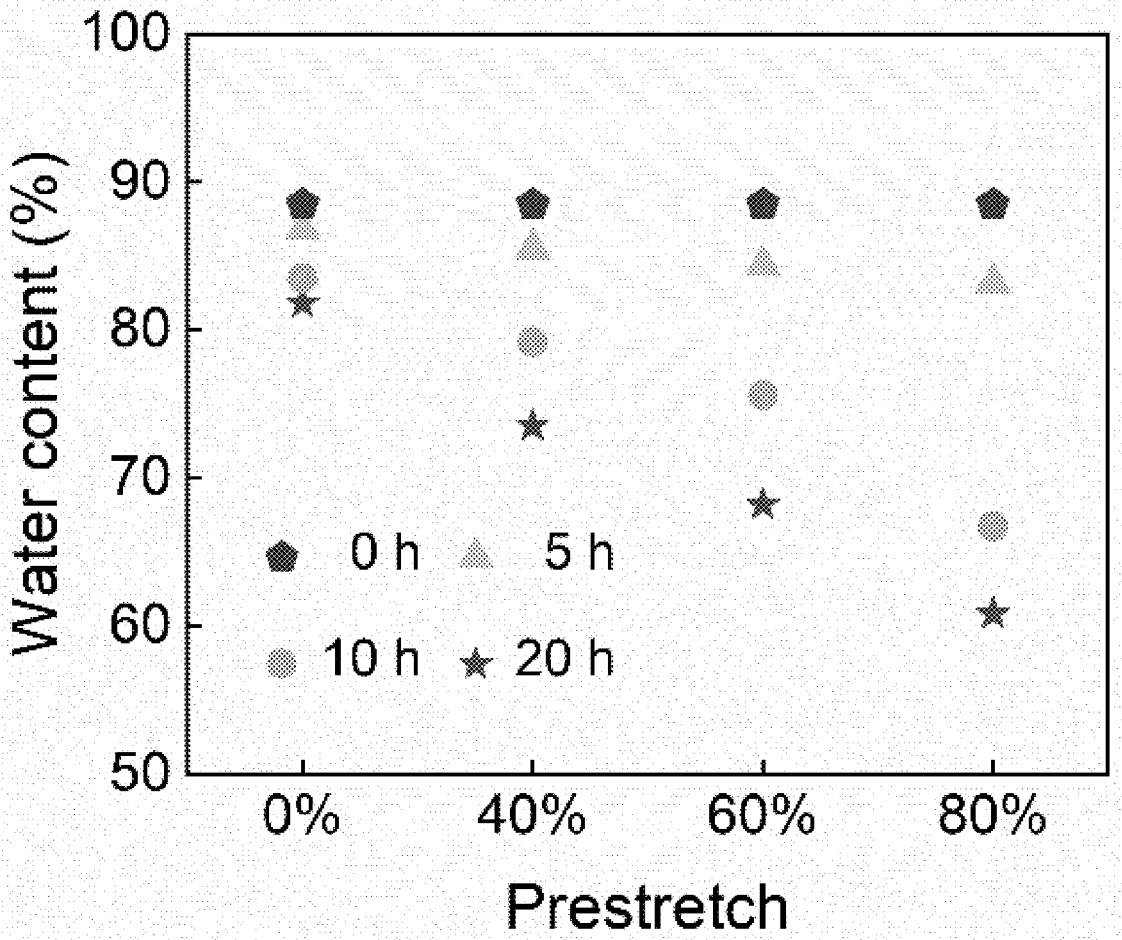
FIG. 9 illustrates the water content of ACHs as a function of pre-stretching (0%, 40%, 60% and 80%) and drying time (0 h, 5 h, 10 h, and 20 h) according to certain embodiments of the subject invention. The samples were immersed in DI water for over 24 h to achieve equilibrium water content before the measurement.
Figure 10A:
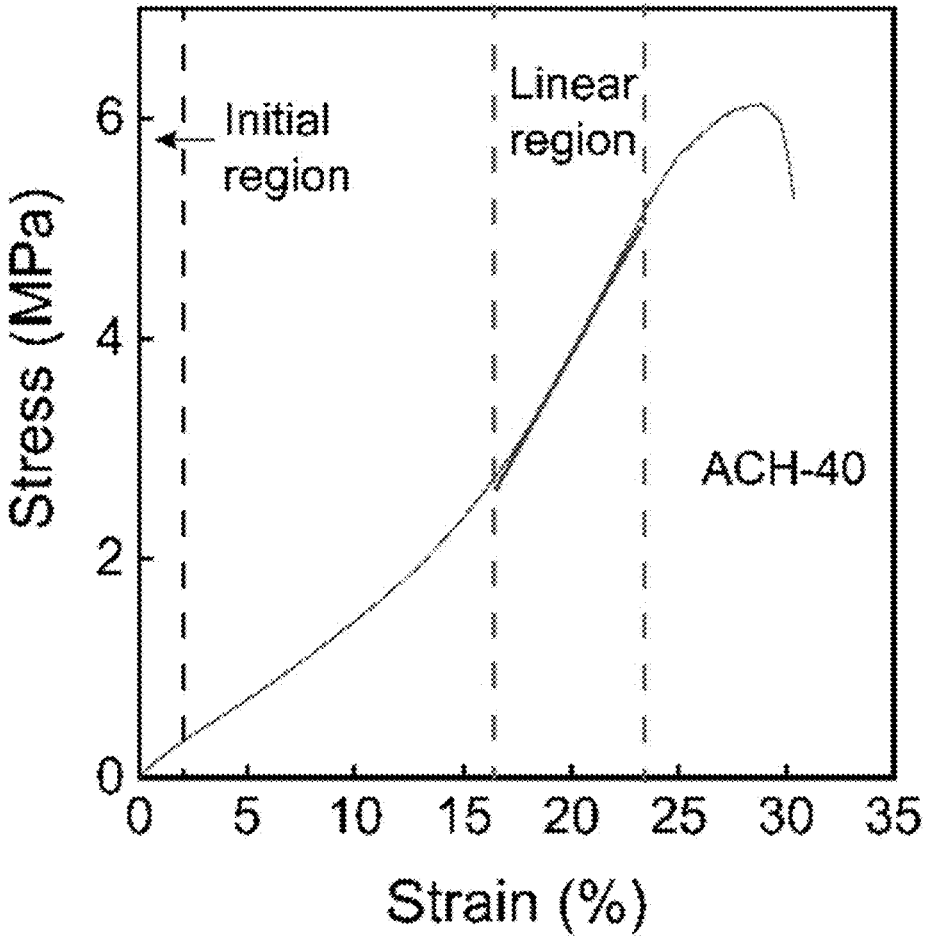
FIGS. 10A-10C illustrates engineering stress-strain curves of ACHs highlighting different regions according to certain embodiments of the subject invention.
Figure 10B:
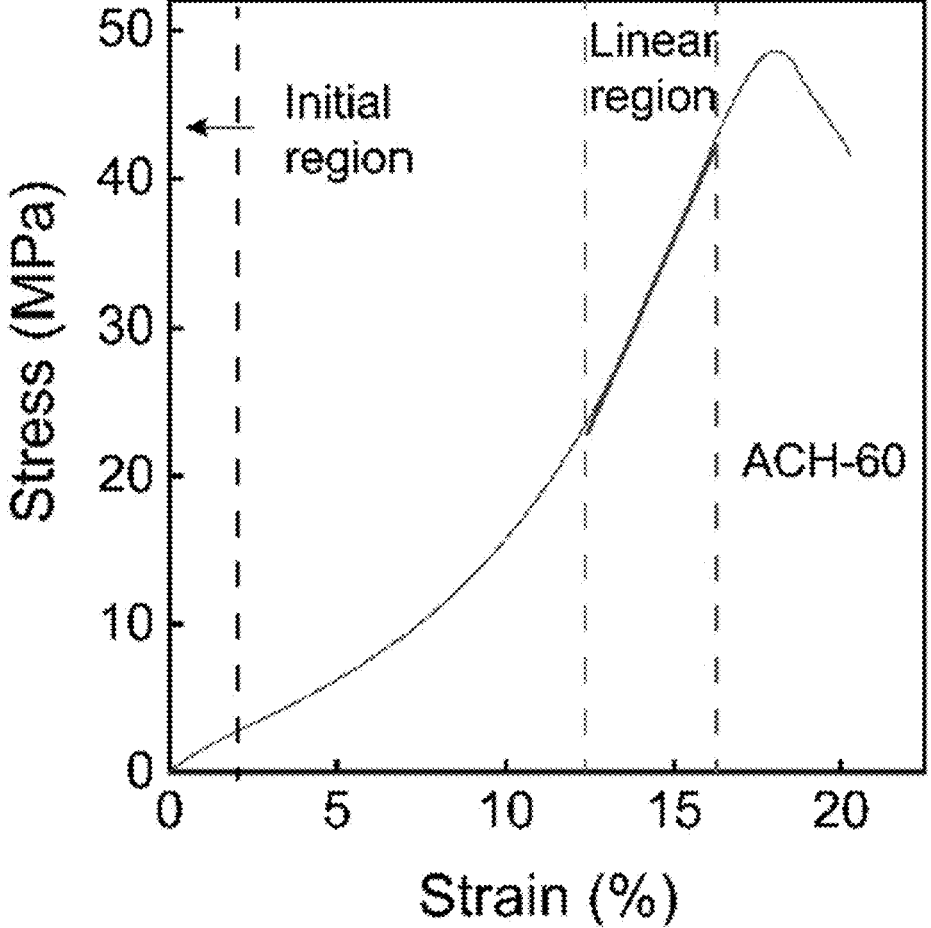
Figure 10C:
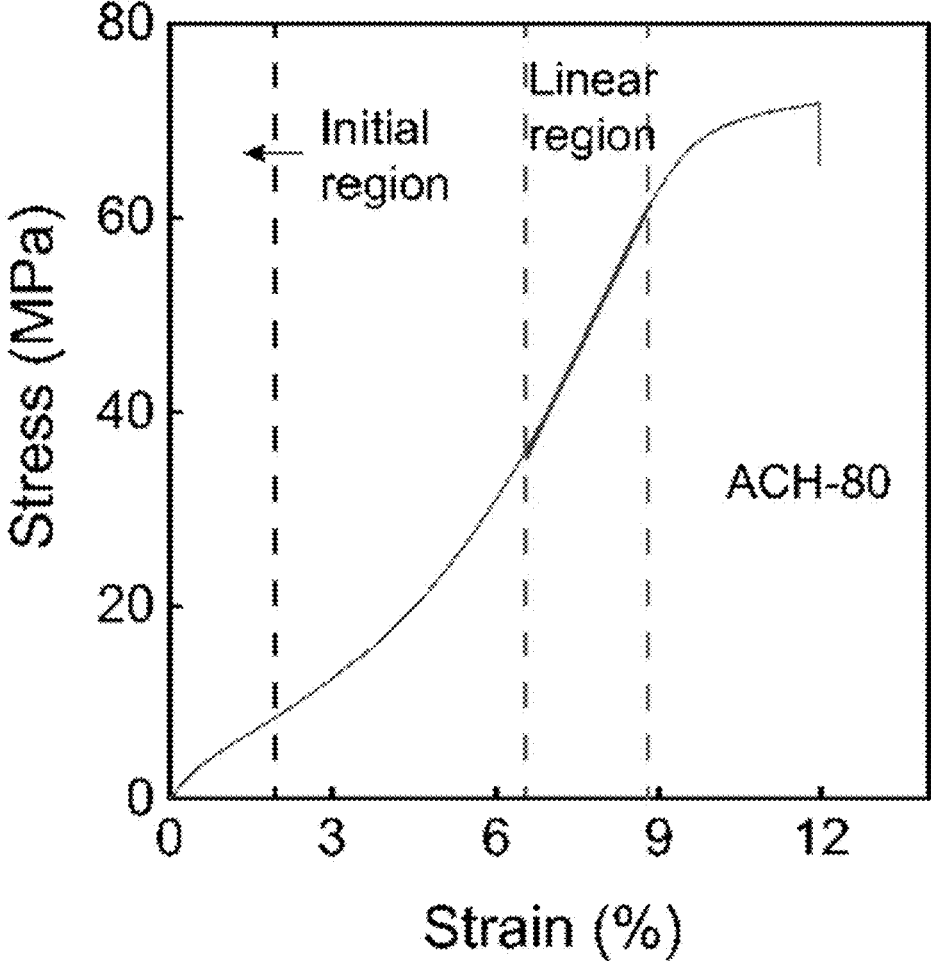

In certain embodiments the stretching-induced orientation of the fibrillar networks significantly influenced the mechanics of ACHs. The inventors have investigated various samples denoted as ACH-x, with x being the percentage of imposed elongation during the pre-stretching-drying process. From microstructural observations, the degree of fiber alignment and bundling in ACHs increase with elongation during the pre-stretching-drying processing (FIGS. 8A-8D). In addition, the interfibrillar interactions in highly stretching-oriented samples (e.g., ACH-80) led to a high solid content in the swollen state (~40%), which contrasts with those processed with lower pre-stretching (FIG. 9). As a result, moduli and strengths of embodiments of the provided ACHs in the direction parallel to the fiber alignment strongly correlate with the degree of imposed elongation during pre-stretching-drying (FIG. 2A), with ACH-80 exhibiting the highest elastic modulus (among those tested) of 1.1 GPa and strength of 72.1 MPa (FIGS. 10A-10C and 11A-11B). These values are ~65 times and ~10 times higher, respectively, than the modulus and strength of isotropic ANF-PVA hydrogels with similar water content (FIGS. 10A-10C and 11A-11B), indicating the contribution of microstructural anisotropy for the mechanics of ACHs. On the other hand, stretching-induced orientation led to a decrease of strength of ACHs in the direction perpendicular to the fiber alignment, partly due to the diminishing contribution of stiff fibers for load bearing (FIG. 2B). The stiffness anisotropy of ACHs, as characterized by the ratio between initial tensile moduli parallel and perpendicular to the fiber alignment, is tunable up to the level of ~80 (i.e., the stiffness measured in a fiber-parallel direction is 80 times higher than the stiffness measured in a fiber-normal (perpendicular) direction, as shown for the ACH-80 embodiment in FIG. 2C), which covers the intrinsic range of biological tissues.[20,21] Stretching (i.e., maximum elongation before breakage) by more than 80% is limited by the properties of the base materials. Notably, the elastic modulus and mechanical strength of ACH-80 embodiments match those of the natural tendons, which was not achieved with other synthetic hydrogels with tendon-mimetic characteristics (FIG. 2D). Moreover, ACH exhibit high toughness in both directions parallel and perpendicular to the pre-stretching (FIG. 2E and FIGS. 13A-13D). Markedly, the aligned fibers in ACHs provide enhanced resistance to crack propagation in the direction perpendicular to their orientation, leading to a fracture energy of as high as 7333 $J/m^2$.

Figure 2F:
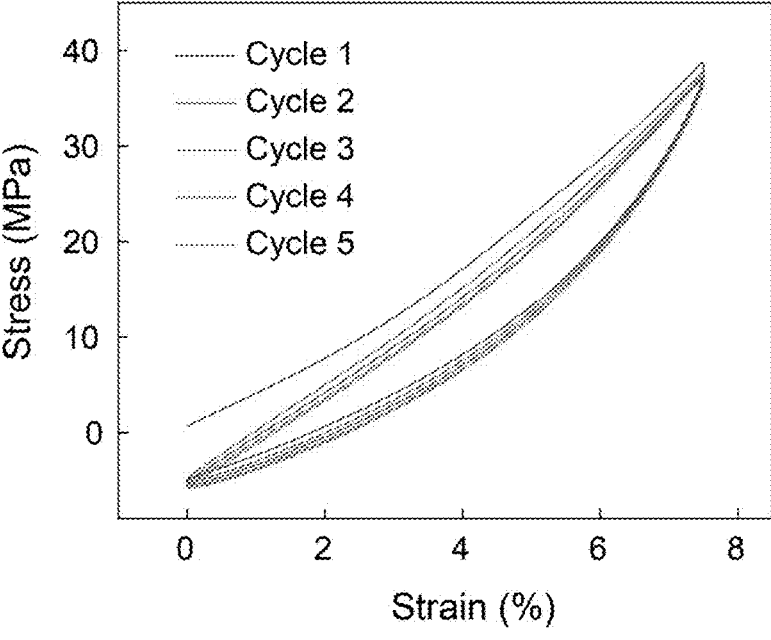
Figure 11A:
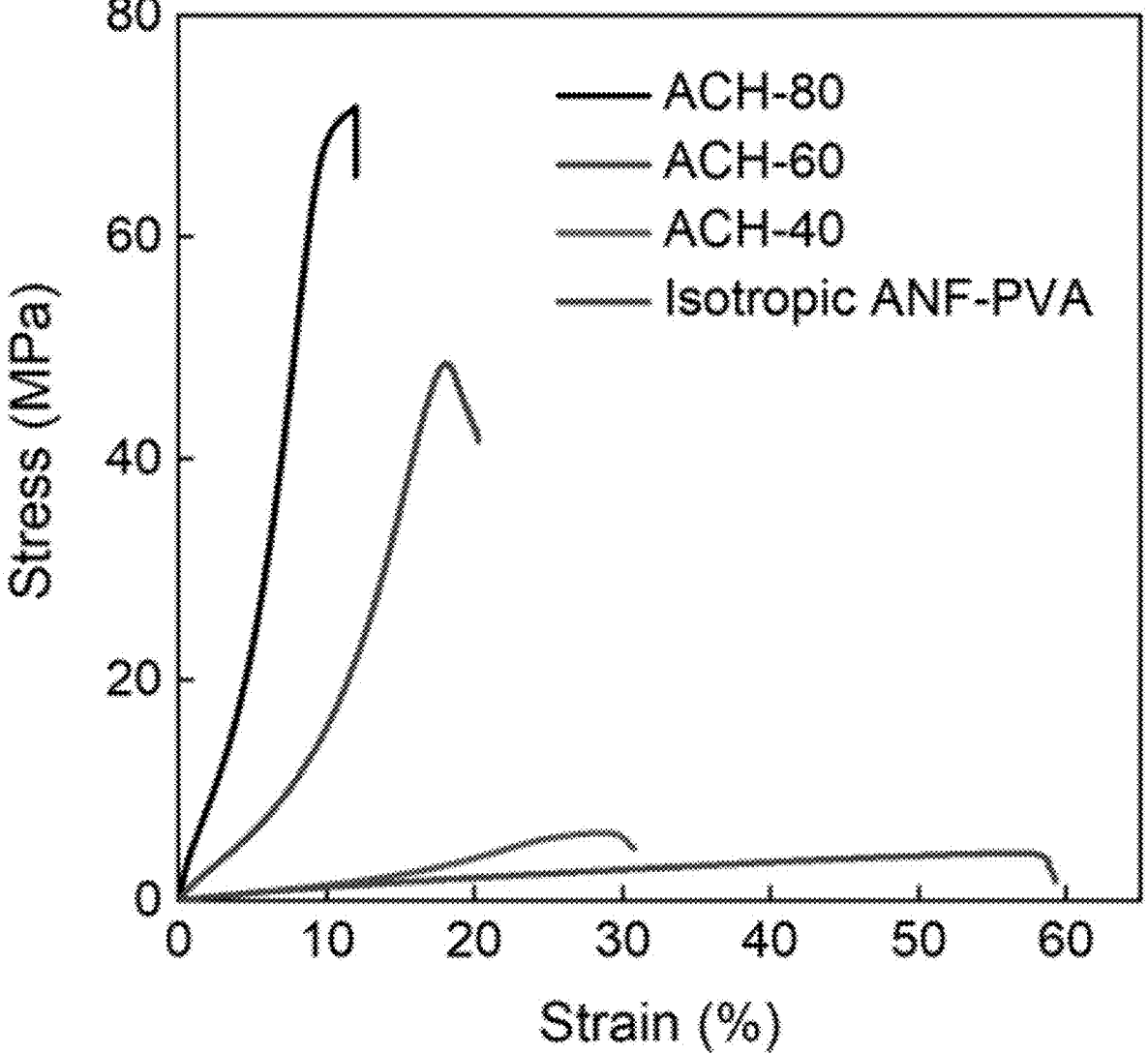
FIGS. 11A-11B illustrate stress-strain curves and modulus-strain curves for ACHs according to certain embodiments of the subject invention.
Figure 11B:
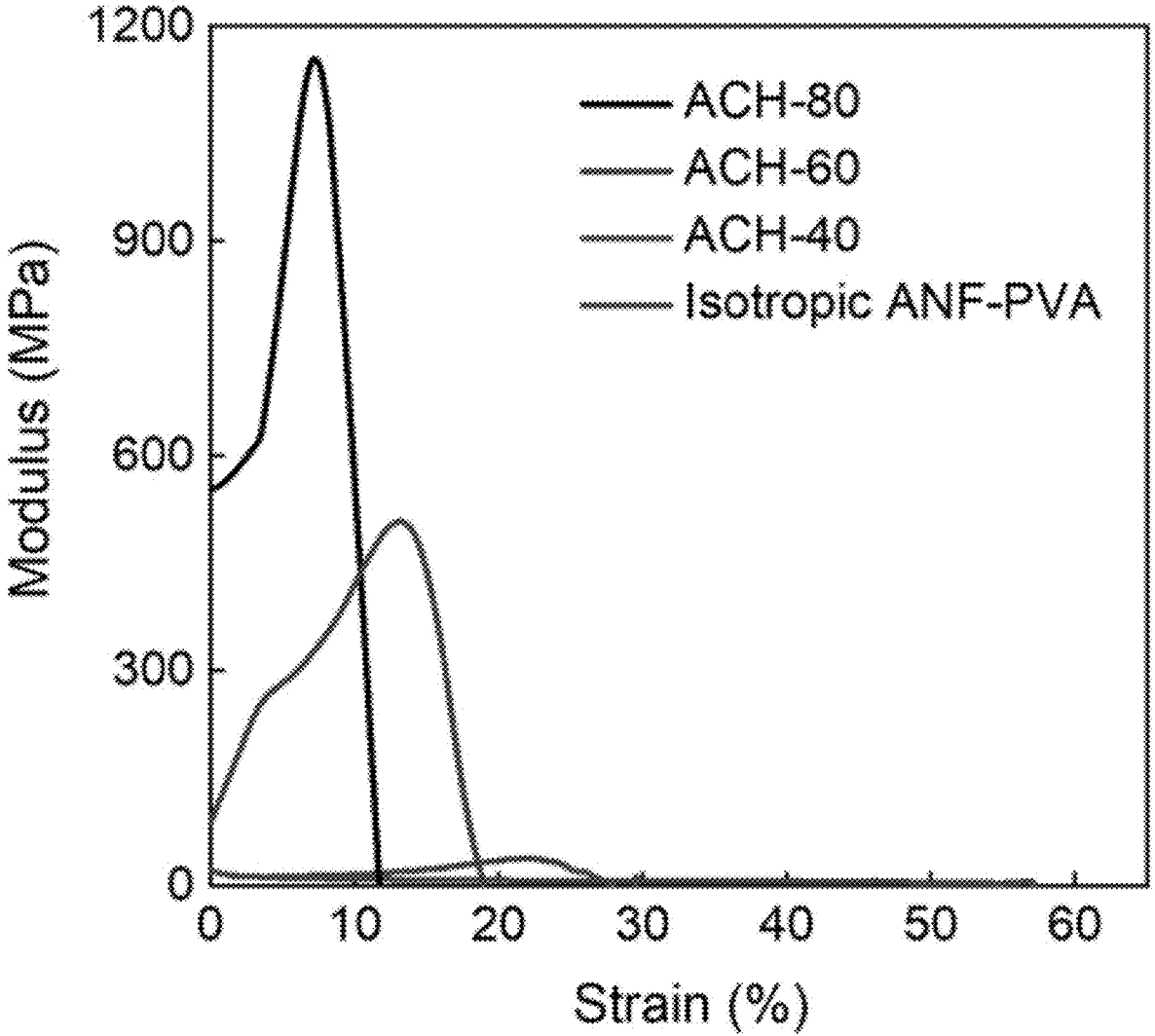
Figure 12A:
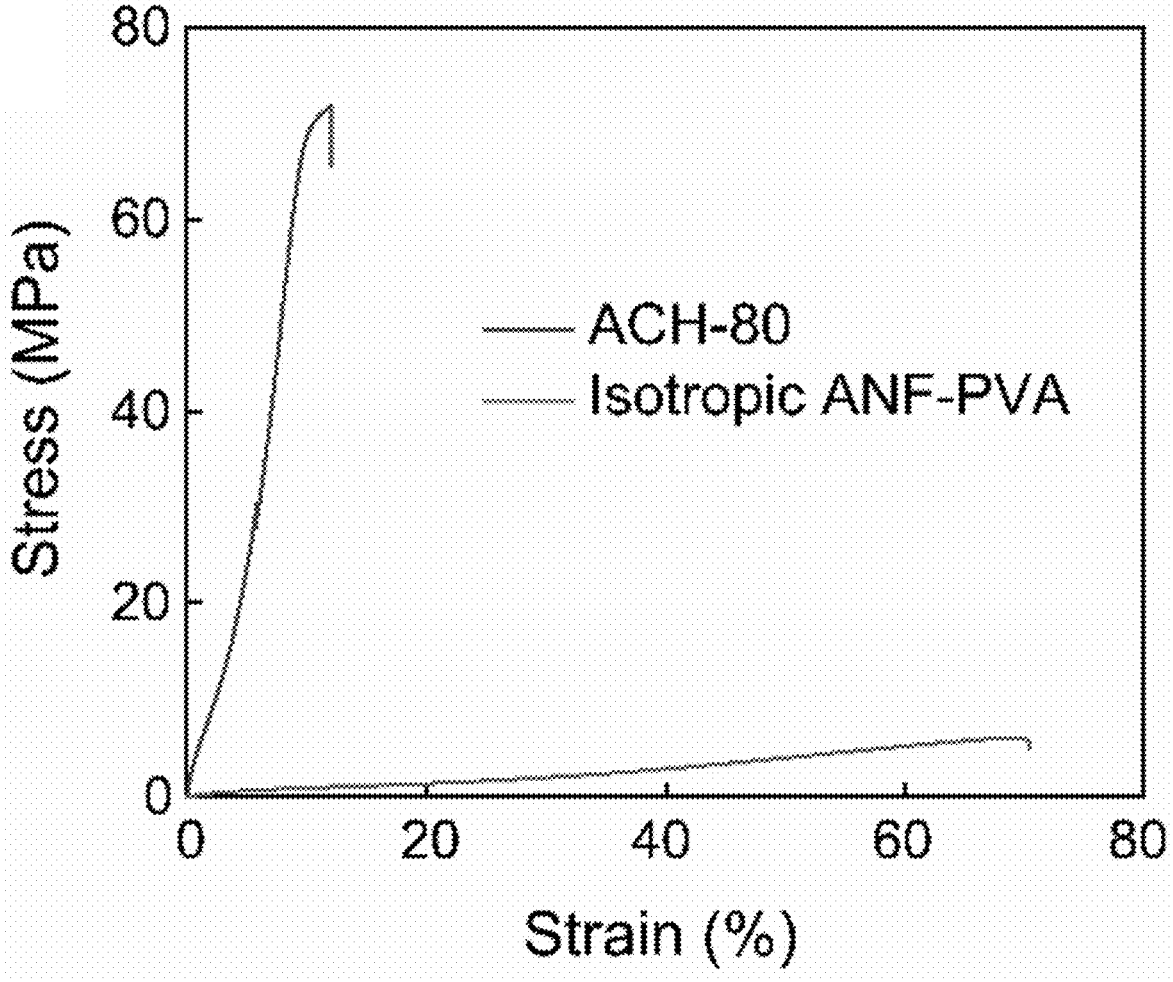
FIGS. 12A-12B illustrate effects of pre-stretching and drying on the mechanics of ACHs according to certain embodiments of the subject invention.
Figure 12B:
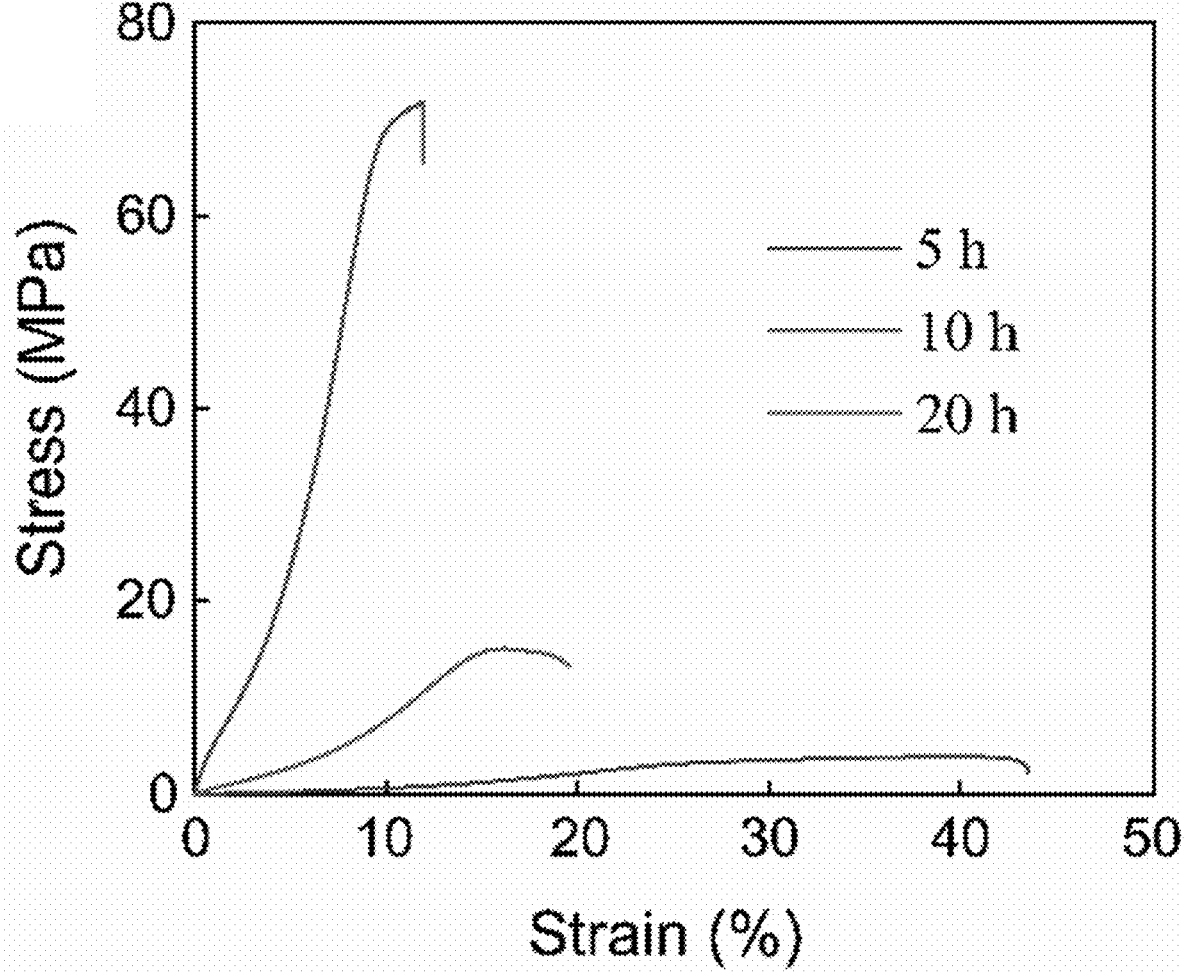
Figure 13A:
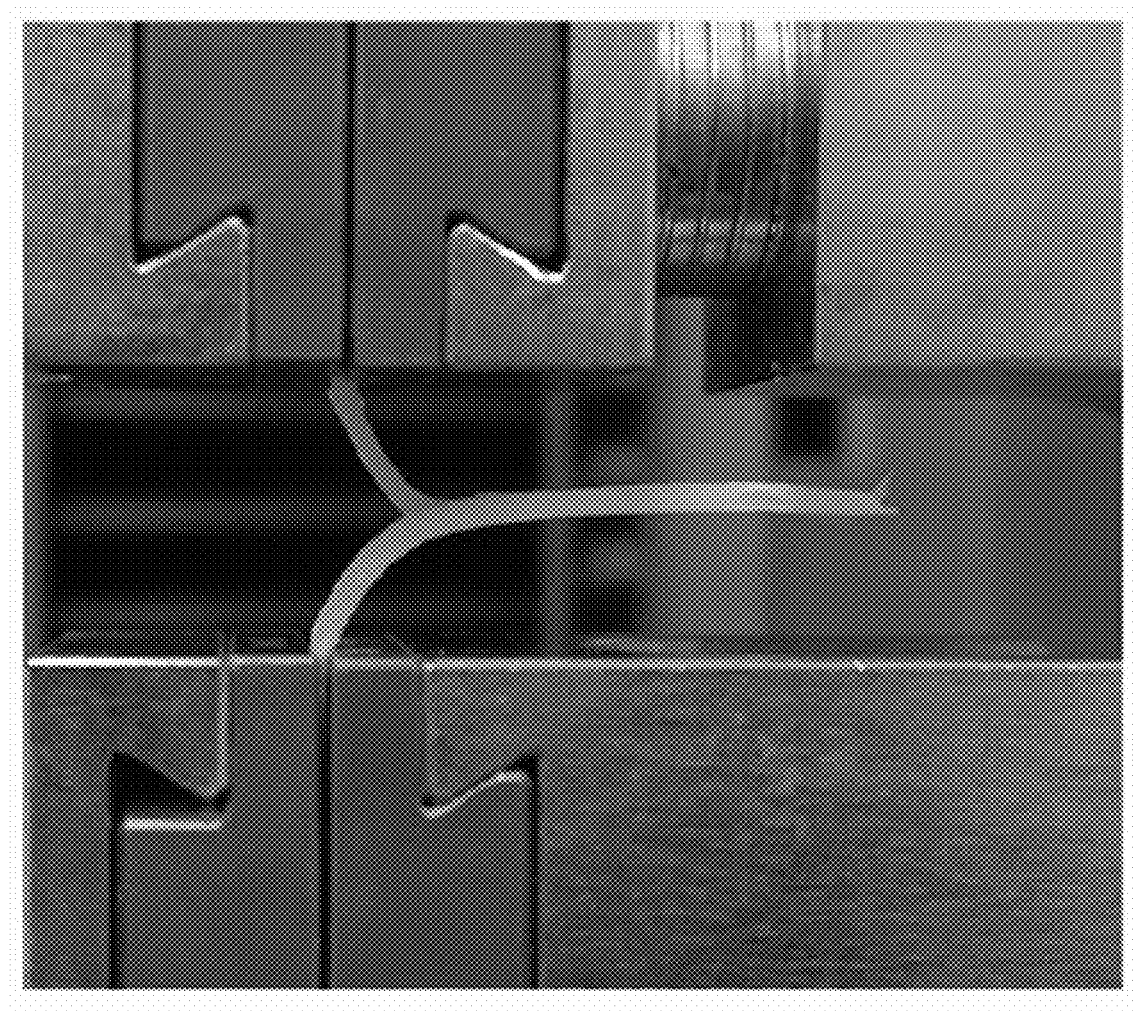
FIGS. 13A-13D illustrate fracture energies of ACHs according to certain embodiments of the subject invention.
Figure 13B:
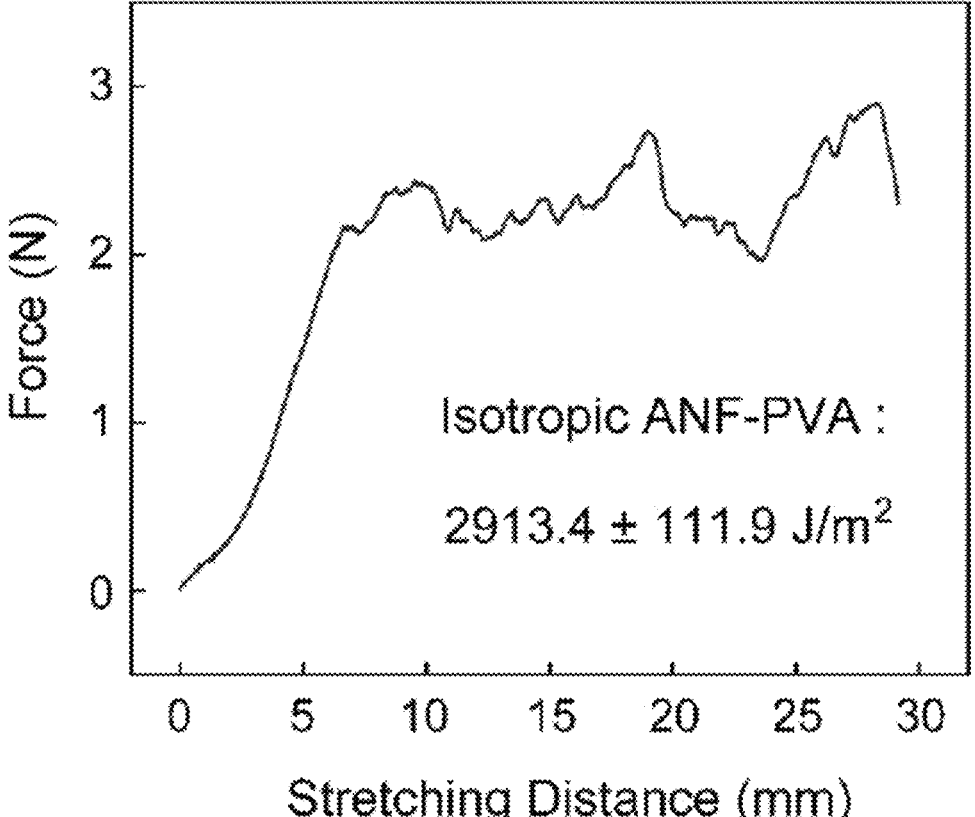
Figure 13C:
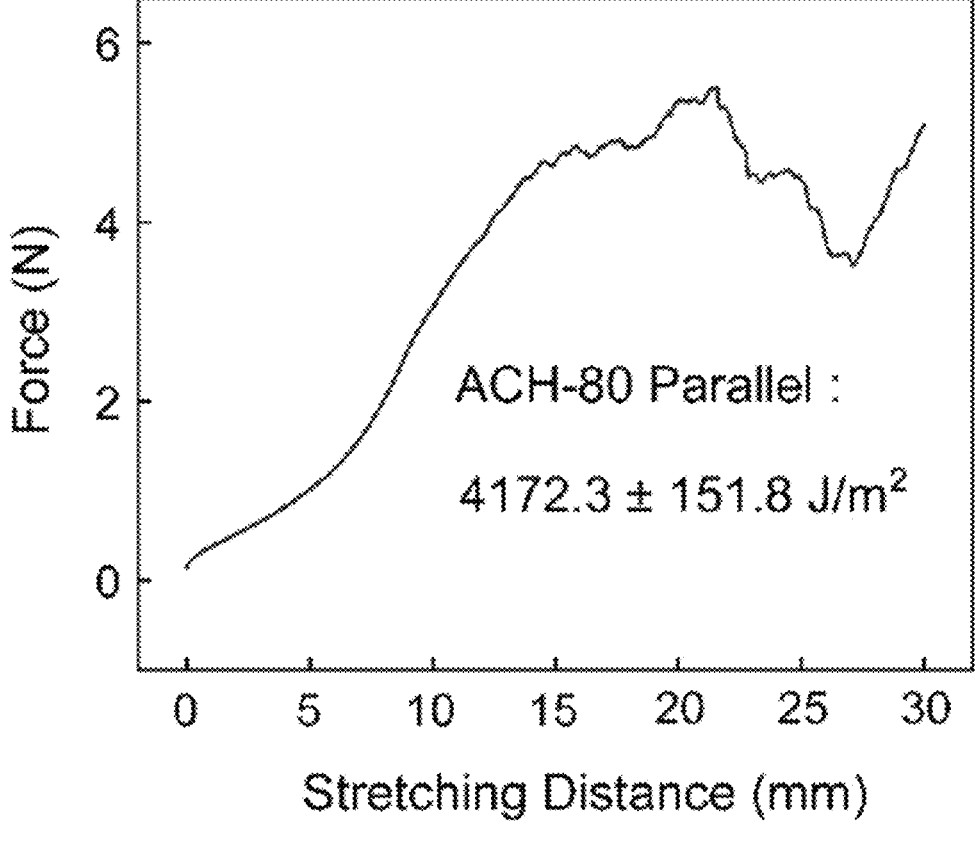
Figure 13D:
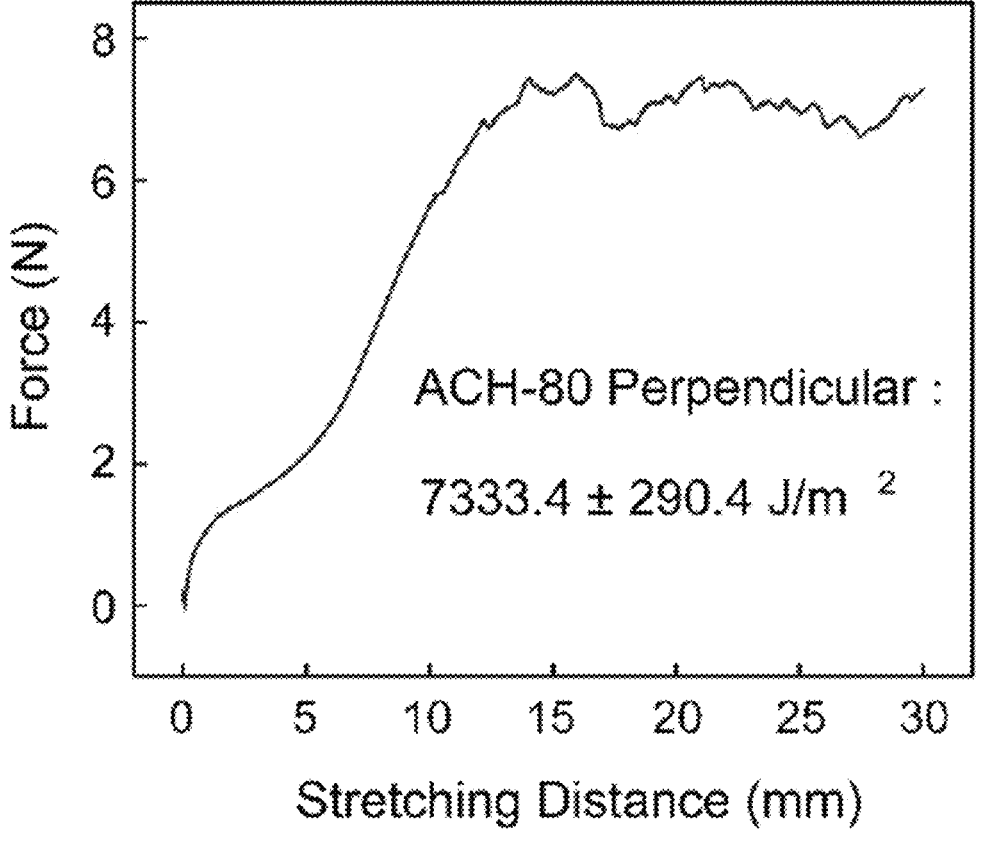
Figure 14A:
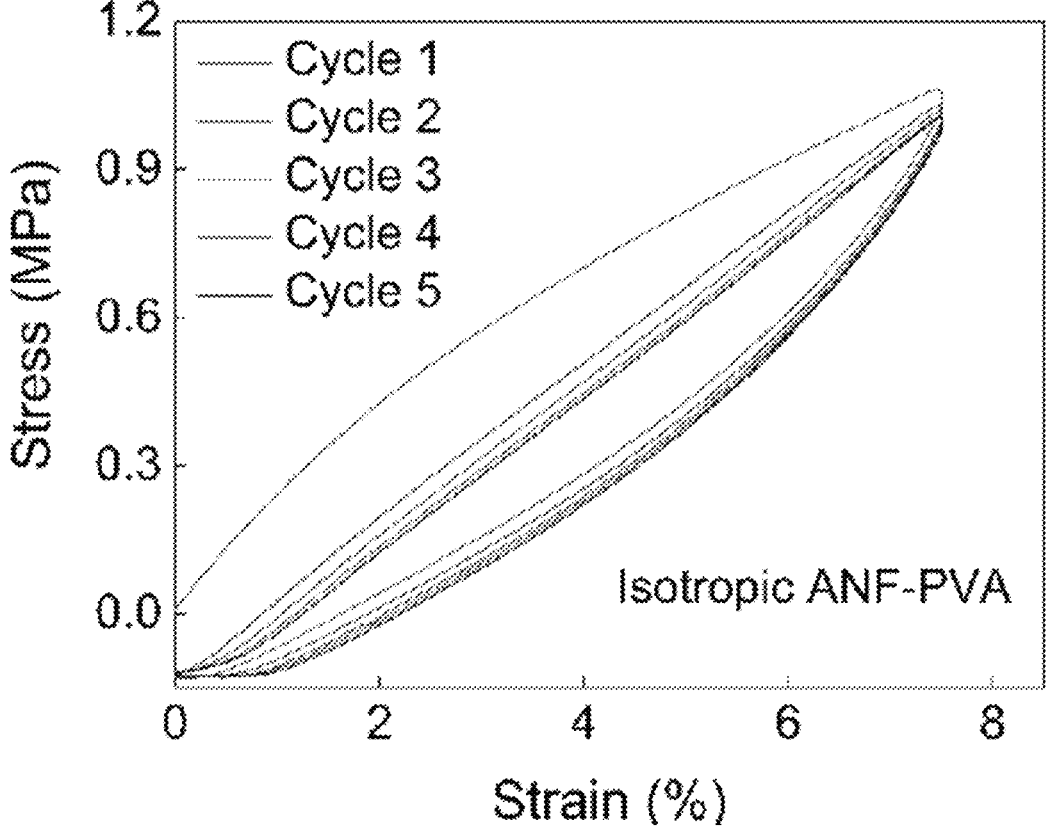
FIG. 14A-14D illustrate the results of cyclic tensile tests on various samples with 7.5% of maximum imposed strain according to certain embodiments of the subject invention.
Figure 14B:
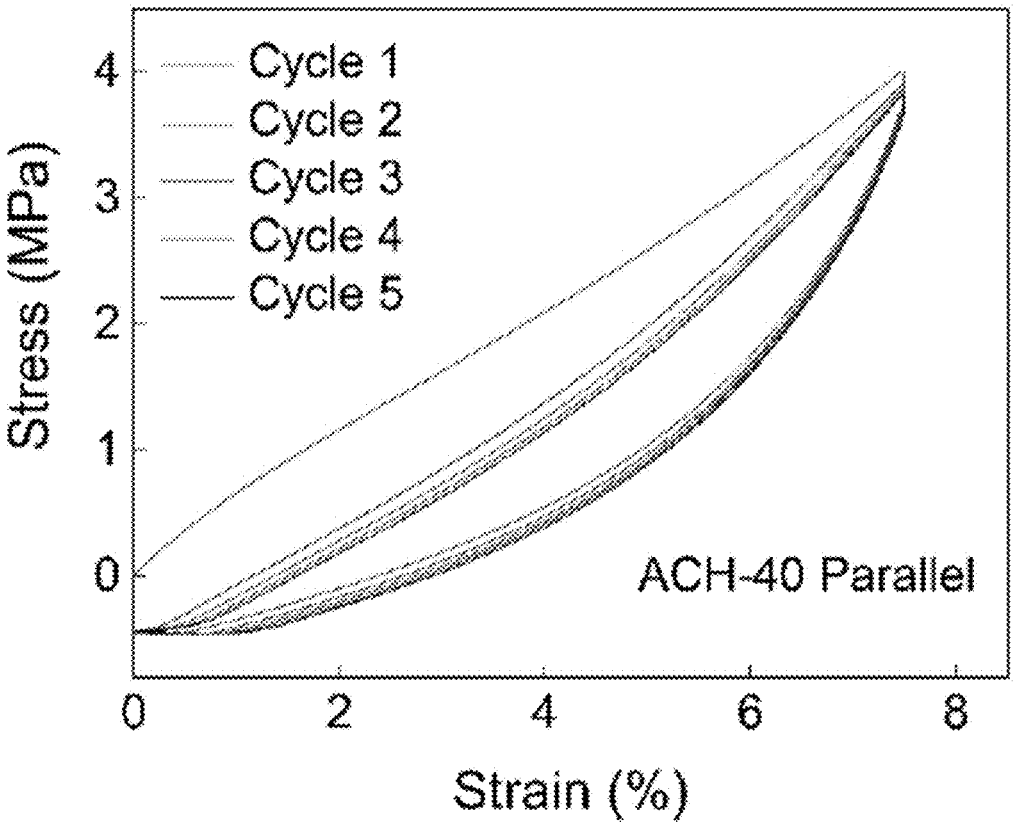
Figure 14C:
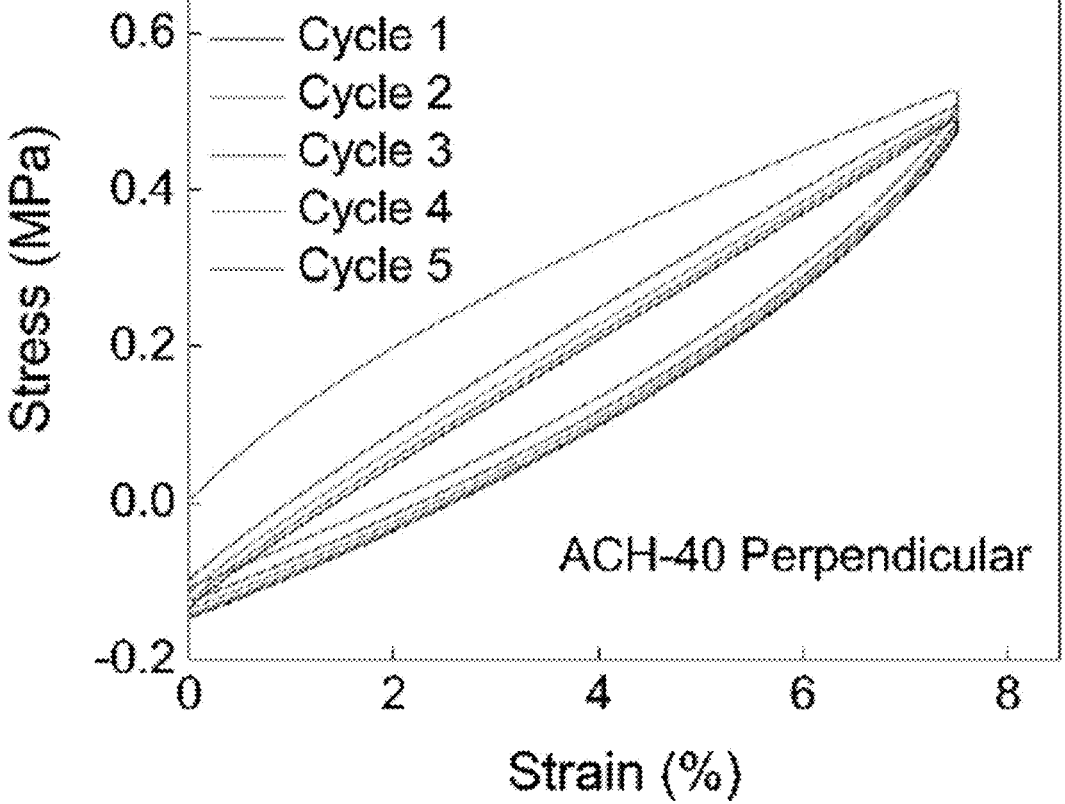
Figure 14D:
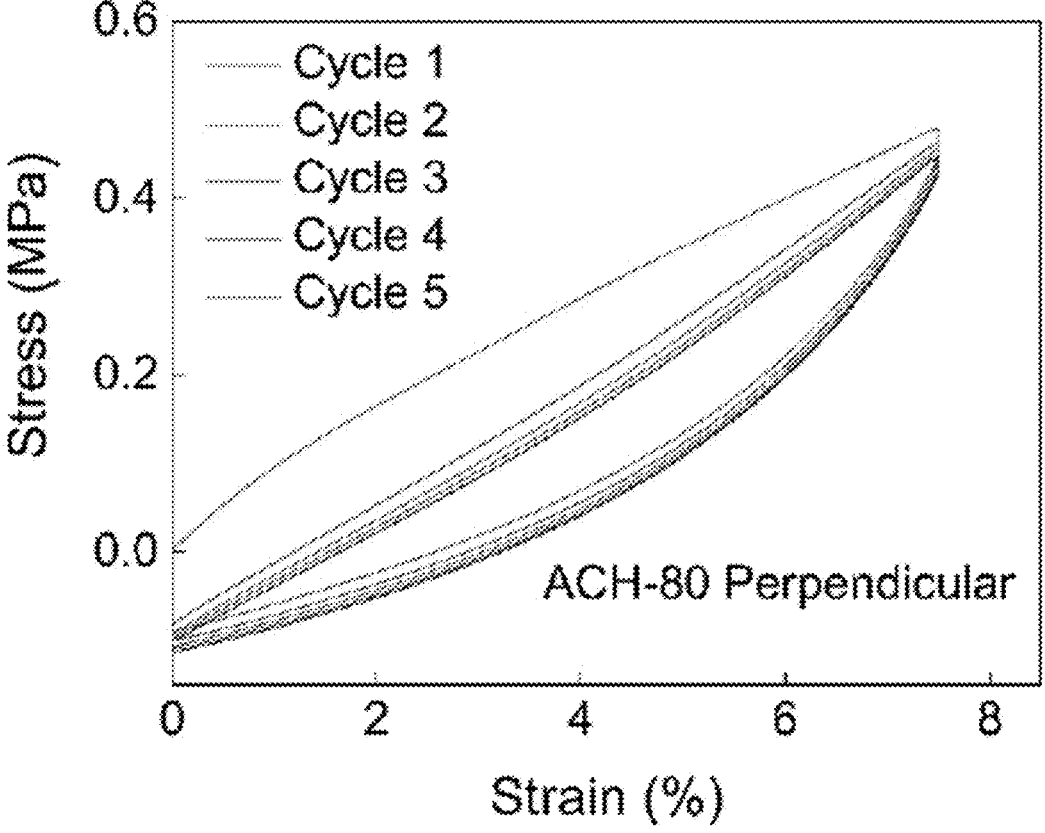
Figure 15:
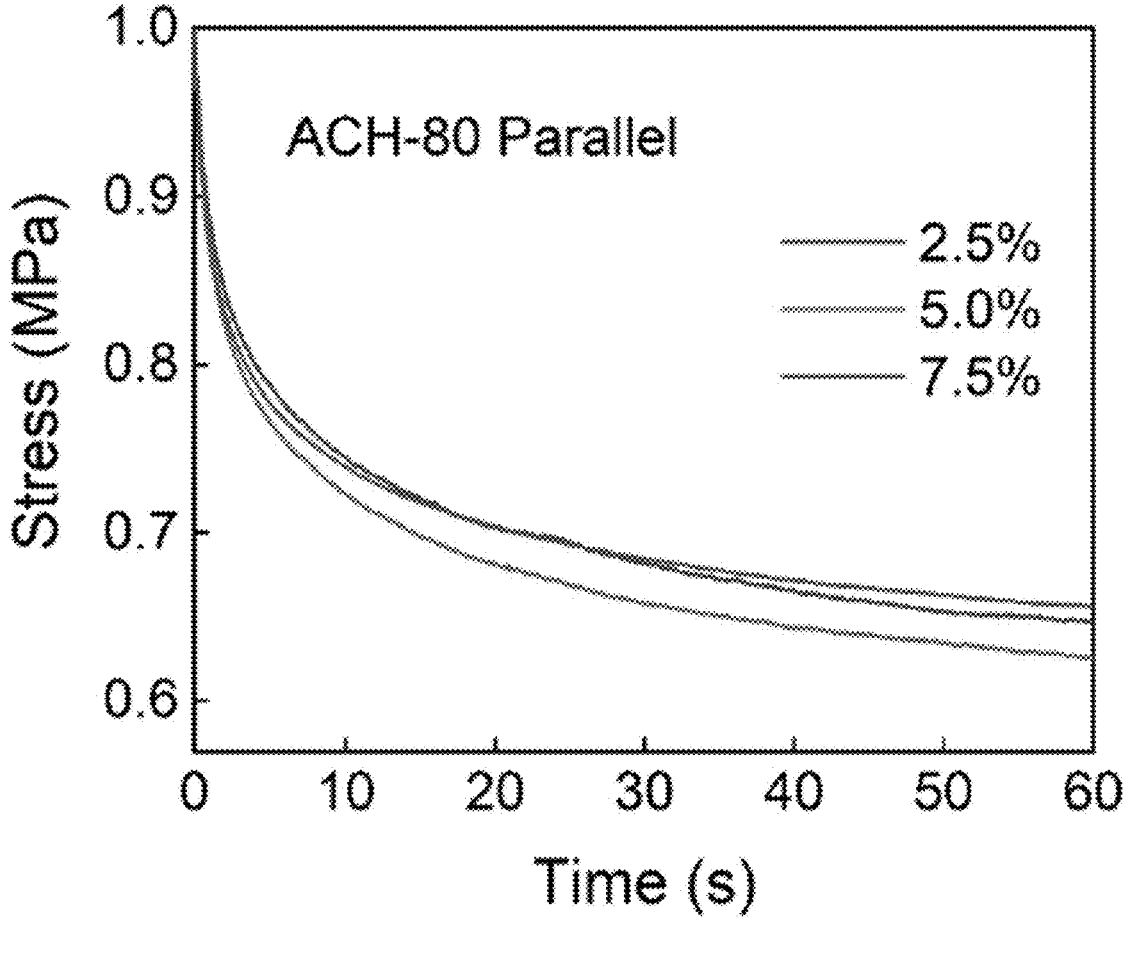
FIG. 15 illustrate stress-relaxation behaviors of ACH-80 under various tensile strains imposed in the direction parallel to the fiber alignment according to certain embodiments of the subject invention. It shows a time constant on the order of ~10s, which is very similar to those of biological soft tissues 3.

While not being bound by theory, the inventors hypothesize that many tendon-mimetic mechanical properties of embodiments comprising ACHs originate from the interplay between the nanoscale constituents. For instance, the reconfigurable hydrogen bonding between ANFs and PVA are believed to impart high plasticity of the network, affording stress-induced orientation for ACHs. The 3D fibrillar network with high-strength nodes bonded by PVA provides excellent load-bearing capabilities. Markedly, ACH-80 sustained a maximum stress of as high as ~39 MPa even under cyclic elongation of 7.5%, indicating high structural robustness (FIG. 2F). The fiber crimping in ACHs is believed to result from the reconfiguration of flexible PVA chains after removing the pre-stretching (Table 1). This feature imparts strain-stiffening behaviors of ACHs (FIGS. 2A and 2F). It has been observed that tangent modulus of ACH-80 ranges from 553.8 MPa to 1157.2 MPa depending on the imposed tensile strain (FIGS. 11A-11B). Furthermore, the abundant non-covalent intermolecular interactions in ACHs also led to viscoelastic responses, as evidenced by hysteresis under cyclic loadings (FIG. 2F and FIGS. 14A-14D) and stress-relaxation with a time constant on the order of ~10s (FIG. 15), which are very similar to the properties of load-bearing soft tissues.[22] These tissue-mimetic mechanical behaviors of embodiments comprising ACHs, taken together, provide for the construction of advanced bio-interfaces.

Figure 16A:
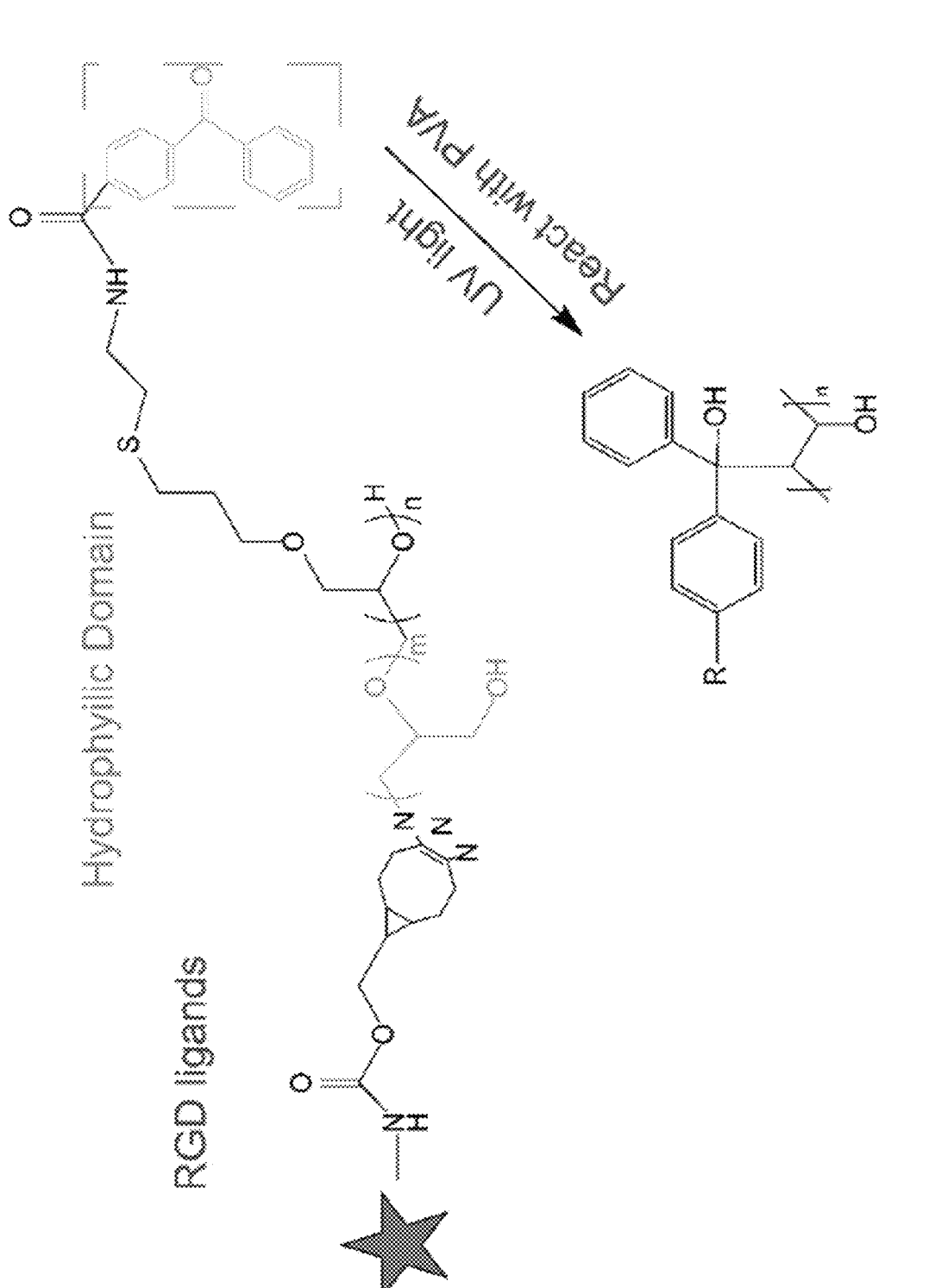
FIG. 16A-16C illustrate surface functionalization of ACH with integrin-binding RGD motif according to certain embodiments of the subject invention.
Figure 16B:
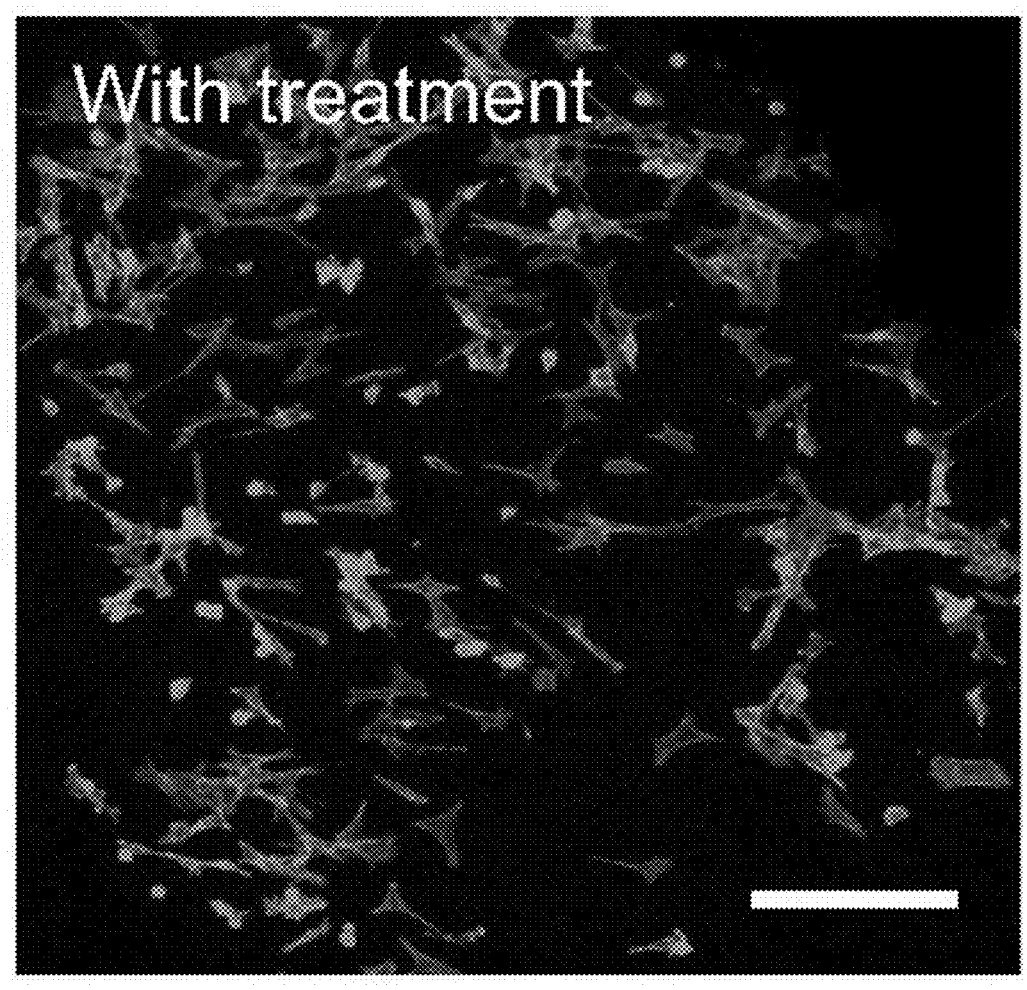
Figure 16C:
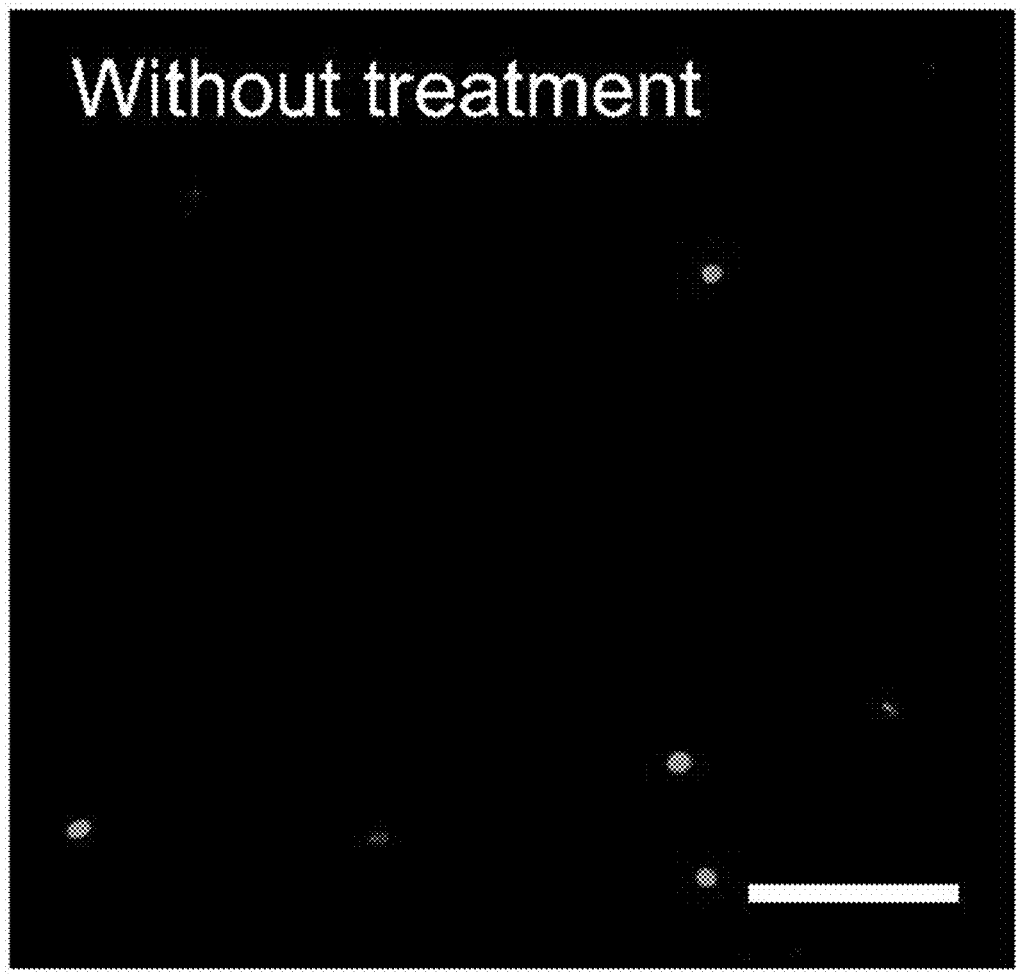
Figure 17A:
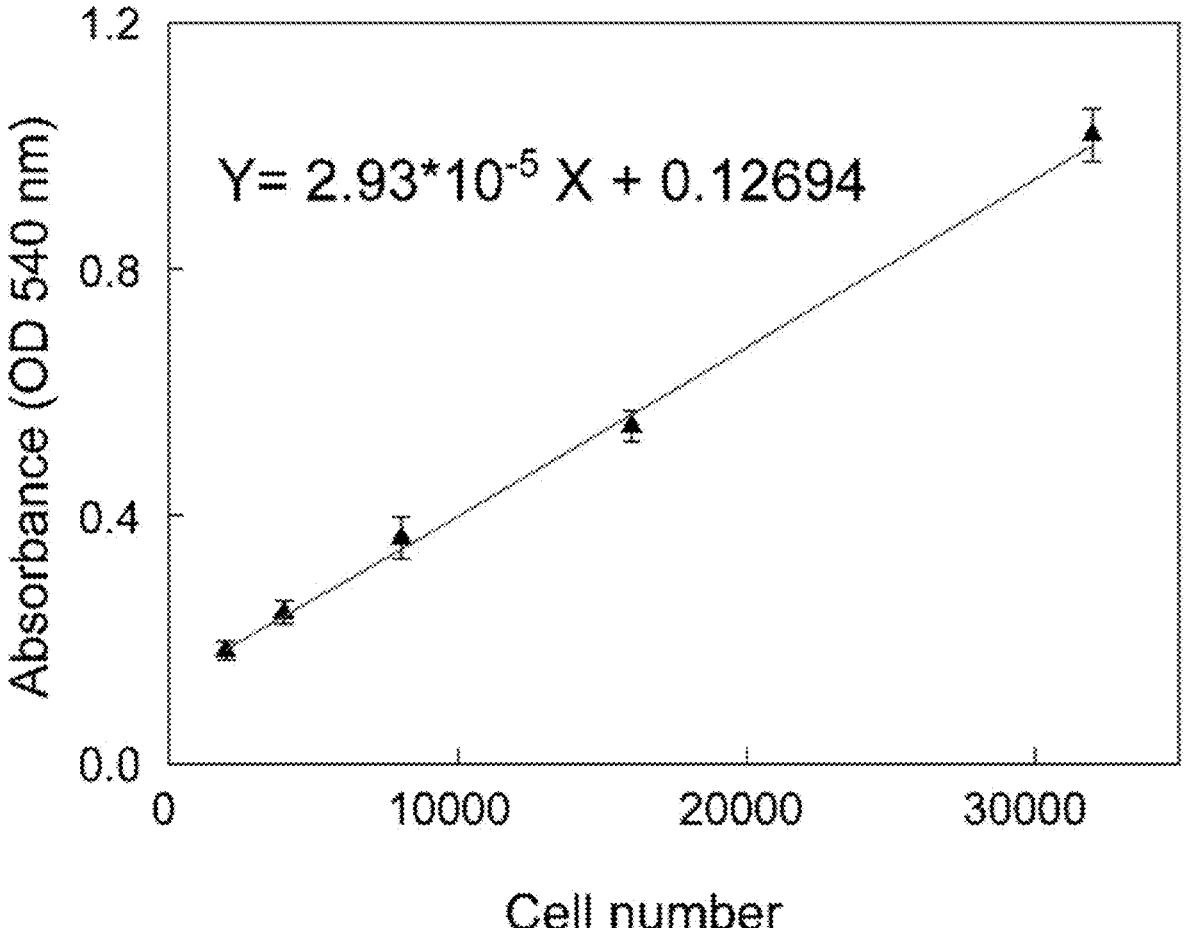
FIG. 17A-17B illustrate cell compatibility of biofunctionalized ACHs characterized with MTT assay according to certain embodiments of the subject invention.
Figure 17B:
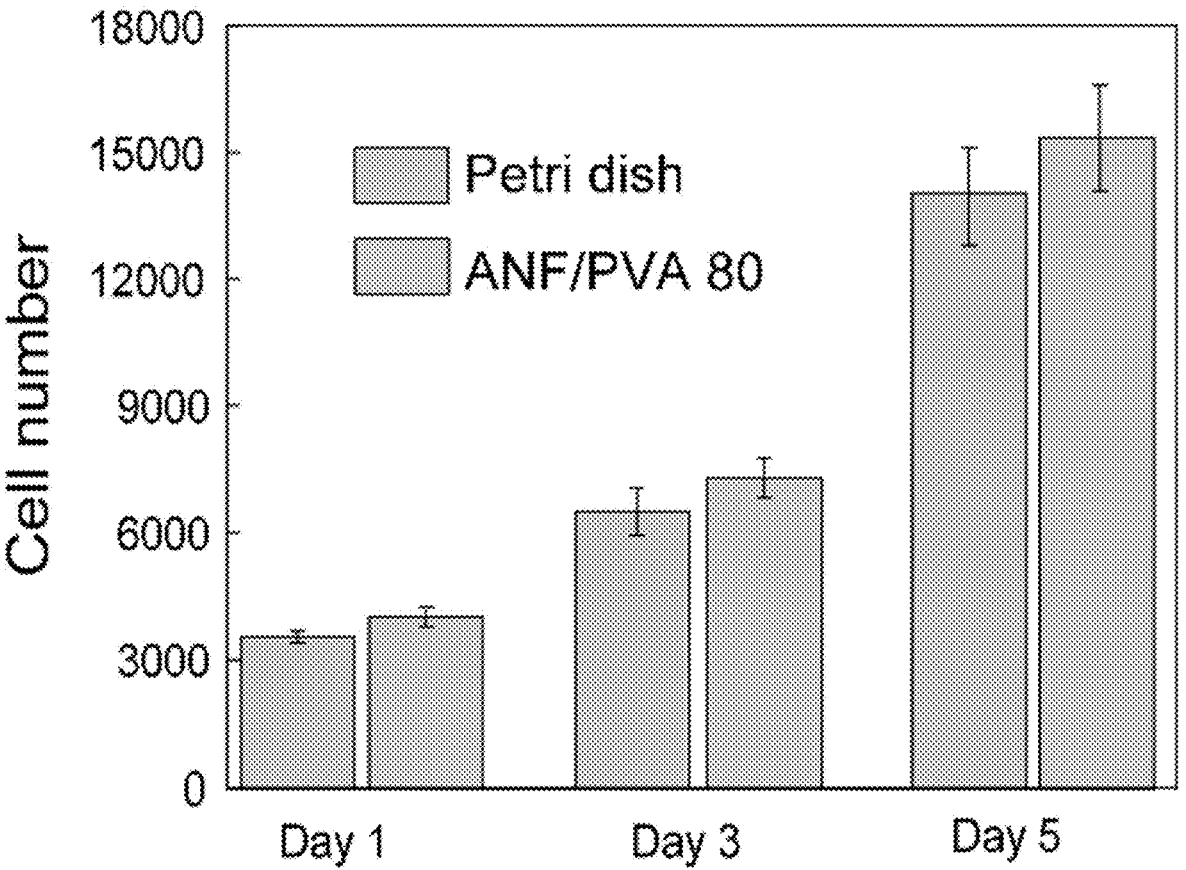

In certain embodiments, the inventors have shown the structural characteristics of ACHs can influence the behaviors of cells through interfacial interactions. To promote cell adhesion and mechanosensing on ACHs, embodiments provide chemical functionalization to present arginylglycylaspartic acid (RGD) motifs for the binding with integrins on the cell membrane. Specifically, benzophenone (BPh) functionalized amphiphilic block copolymers involving linear polyglycerol (LPG) can be adsorbed on the surface of ACH in an aqueous environment. The terminal group of the hydrophilic LPG units are linked to integrin-binding motif cycloRGDfK.[23] Under illumination with ultraviolet (UV) light, the BPh groups grafted to the backbone of PVA and crosslinked with adjacent block copolymers via hydrogen atom abstraction, leading to a functional coating covalently bonded with ACHs (FIGS. 16A-16B). Successful biofunctionalization for ACHs was evidenced by the adhesion of NIH3T3 fibroblasts on their surfaces showing typical spindle-like morphology (FIGS. 16A-16B). In contrast, samples without surface functionalization led to little attachment of cells. The good cytocompatibility of ACHs was also confirmed with MTT (3-(4,5-dimethylthiazol-2-yl)-2,5-diphenyltetrazolium bromide) assay (FIGS. 17A-17B).

Figures 3A, 3B:
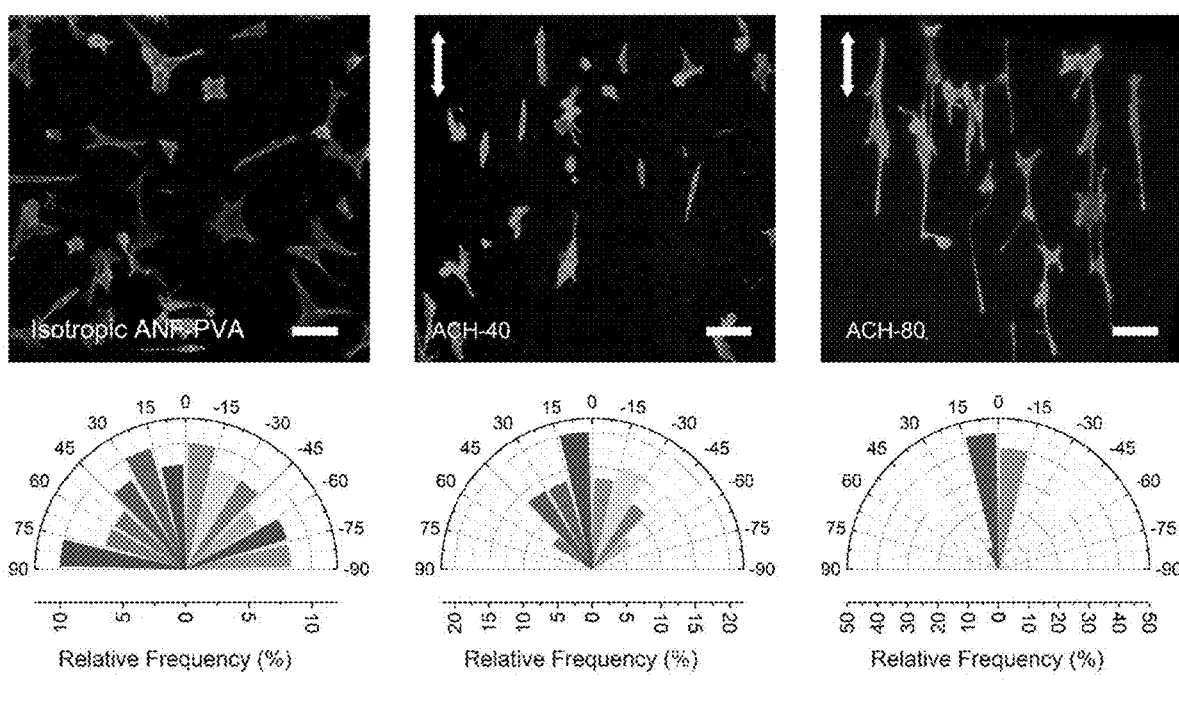
FIGS. 3A-3D Are charts illustrating regulating cell morphology and phenotypes with biofunctionalized ACHs according to certain embodiments of the subject invention.
Figure 18:
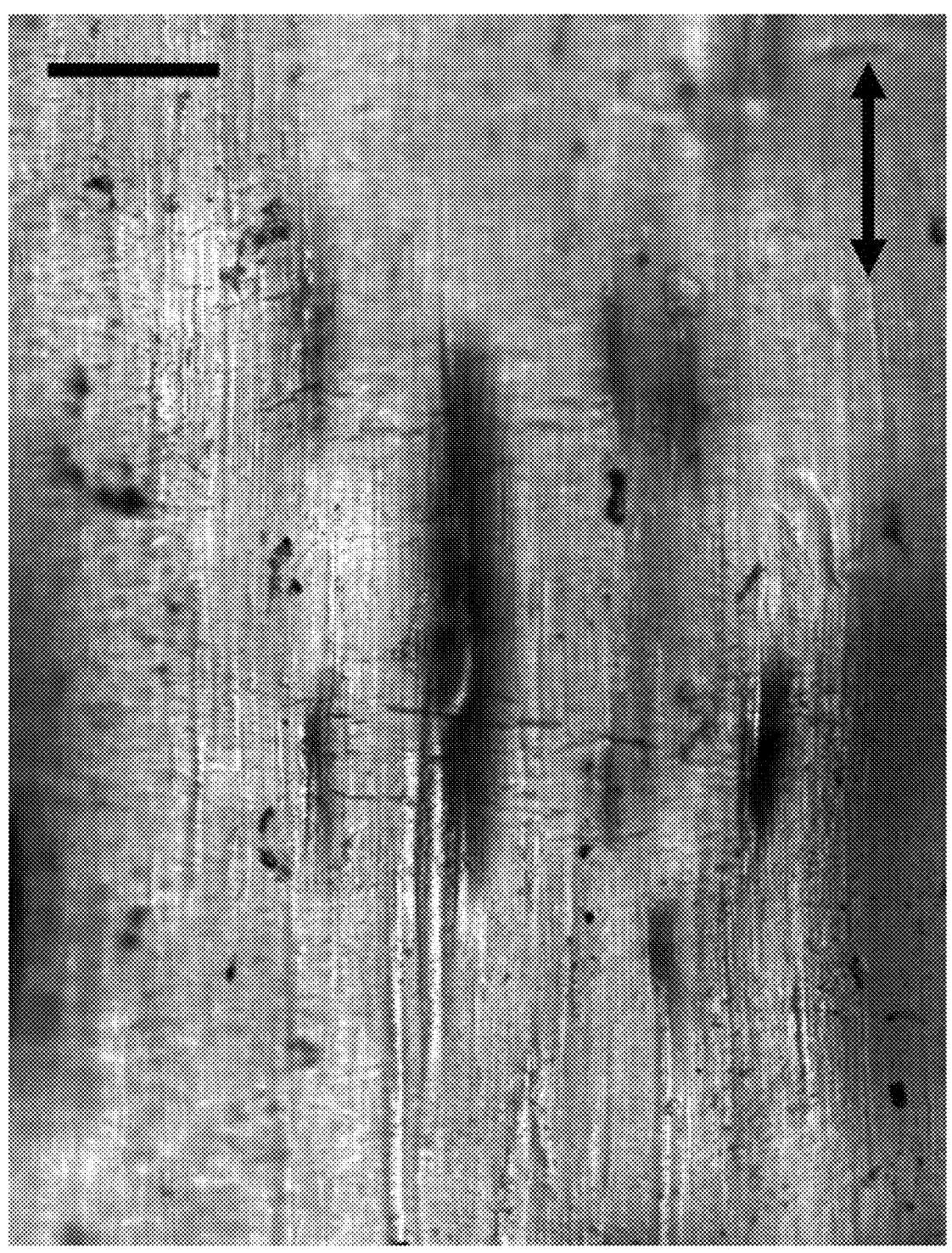
FIG. 18 is an optical microscope image of ACH-80 according to an embodiment of the subject invention. It shows anisotropic surface topography, that can influence the morphology of attached cells via contact guidance. Scale bar: 100 μm.
Figure 19:
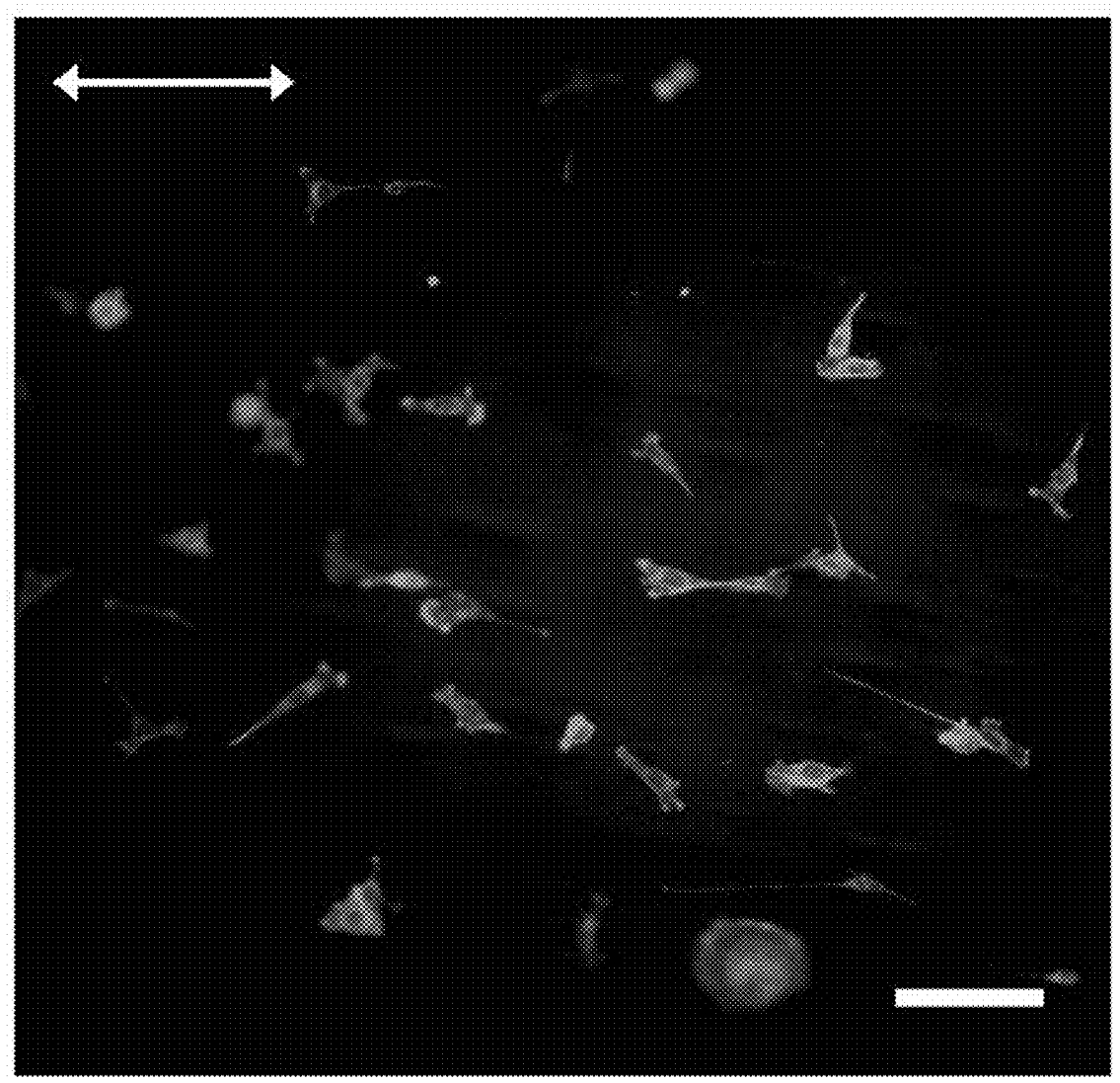
FIG. 19 is a fluorescence image of NIH3T3 fibroblasts cultured on a ACH-80 treated with oxygen plasma etching for 2 h followed by re-swelling and biofunctionalization according to an embodiment of the subject invention. The cells exhibit much less orientation as compared with those cultured on ACH-80 without etching. (Scale bar: 100 μm).
Figure 20A:
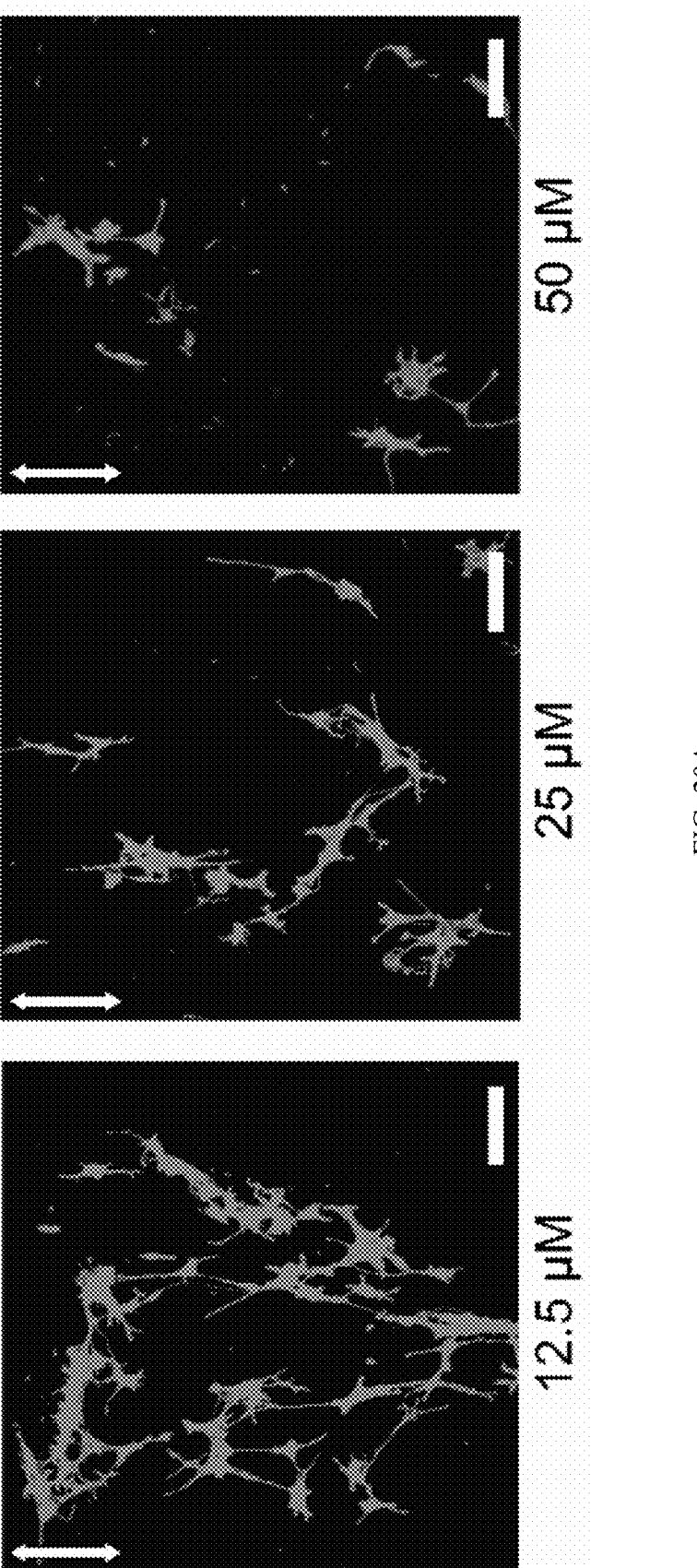
FIG. 20A-20B illustrate the effects of ROCK inhibitor Y-27623 on the morphology of NIH3T3 fibroblasts cultured on ACH-80 according to an embodiment of the subject invention.
Figure 20B:
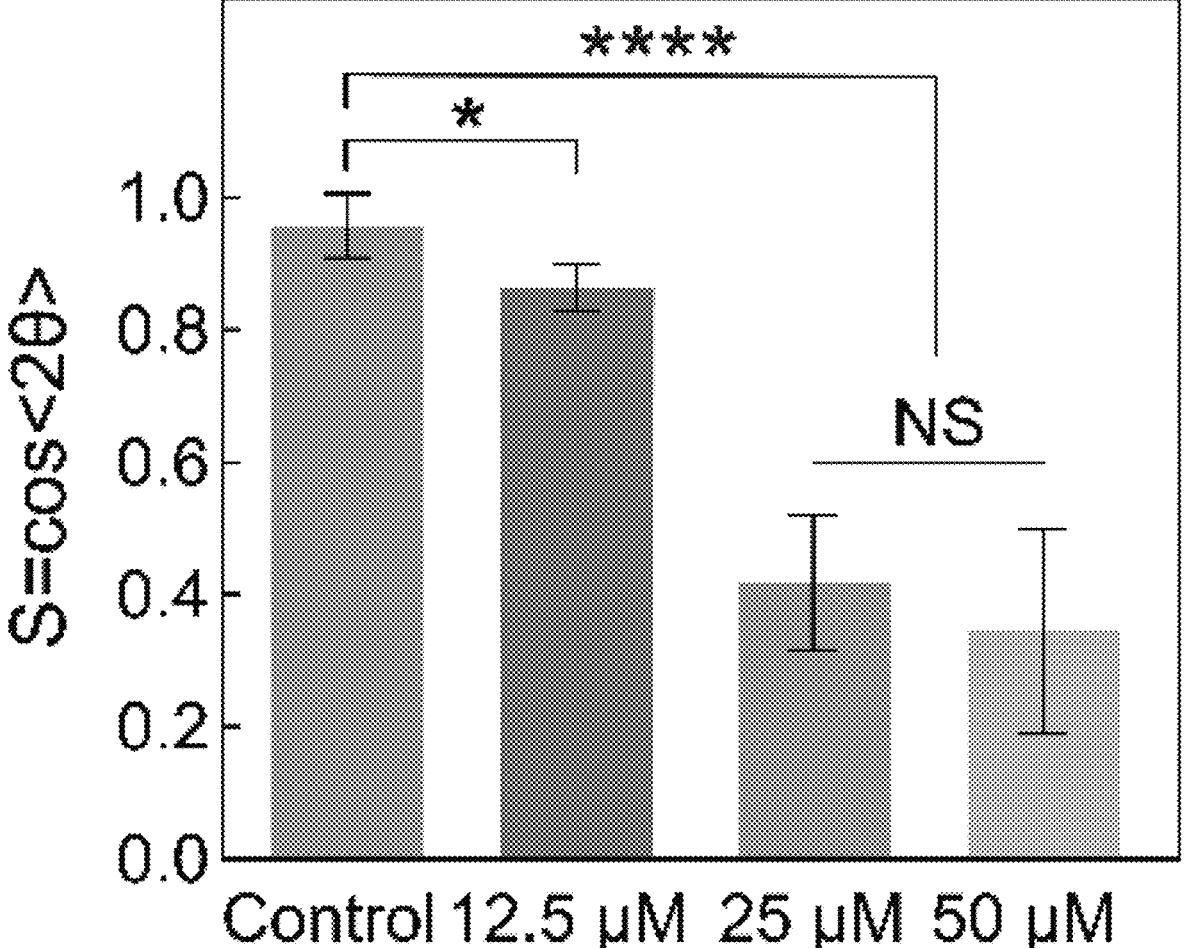
Figure 21A:
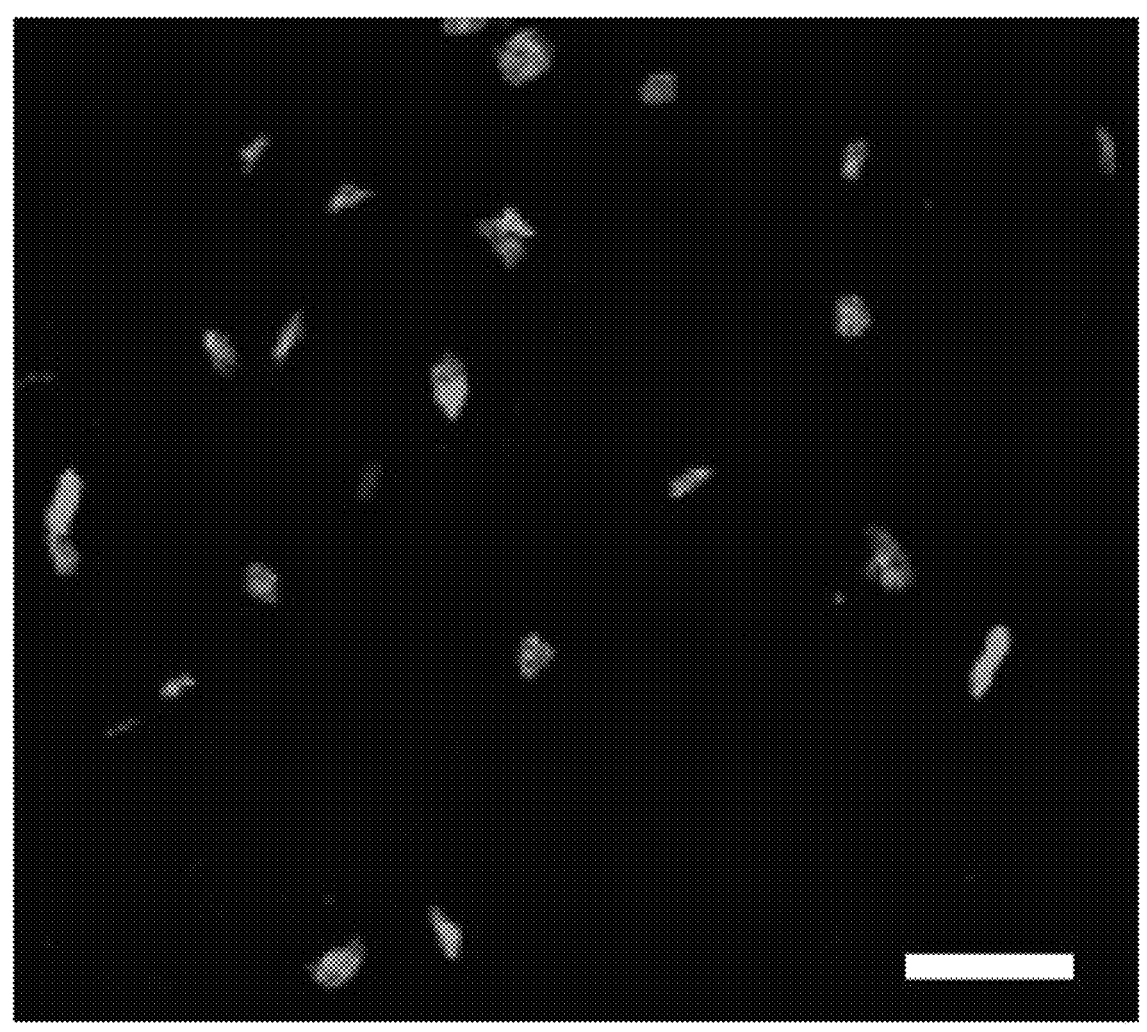
FIG. 21A-21C illustrate raw 264.7 macrophages cultured on various samples according to certain embodiments of the subject invention.
Figure 21B:
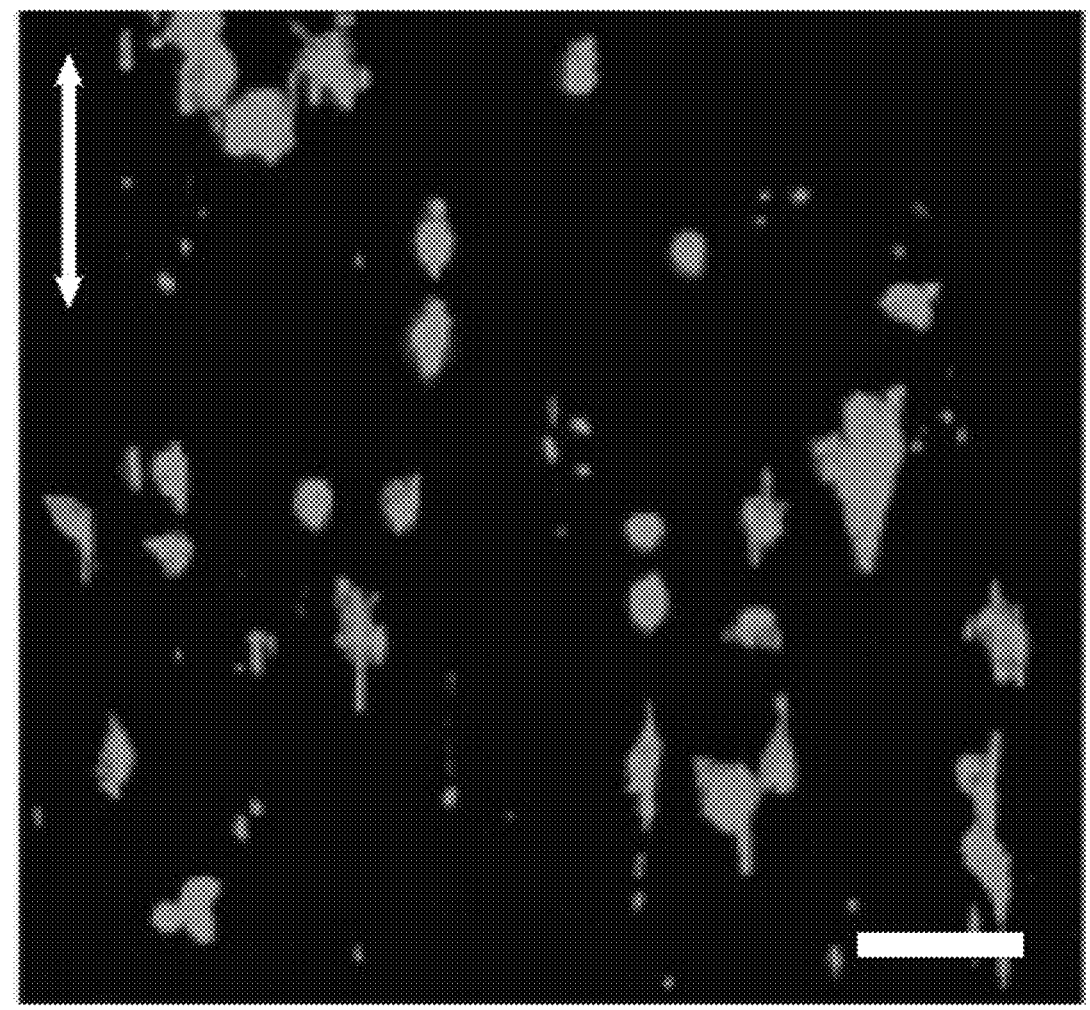
Figure 21C:
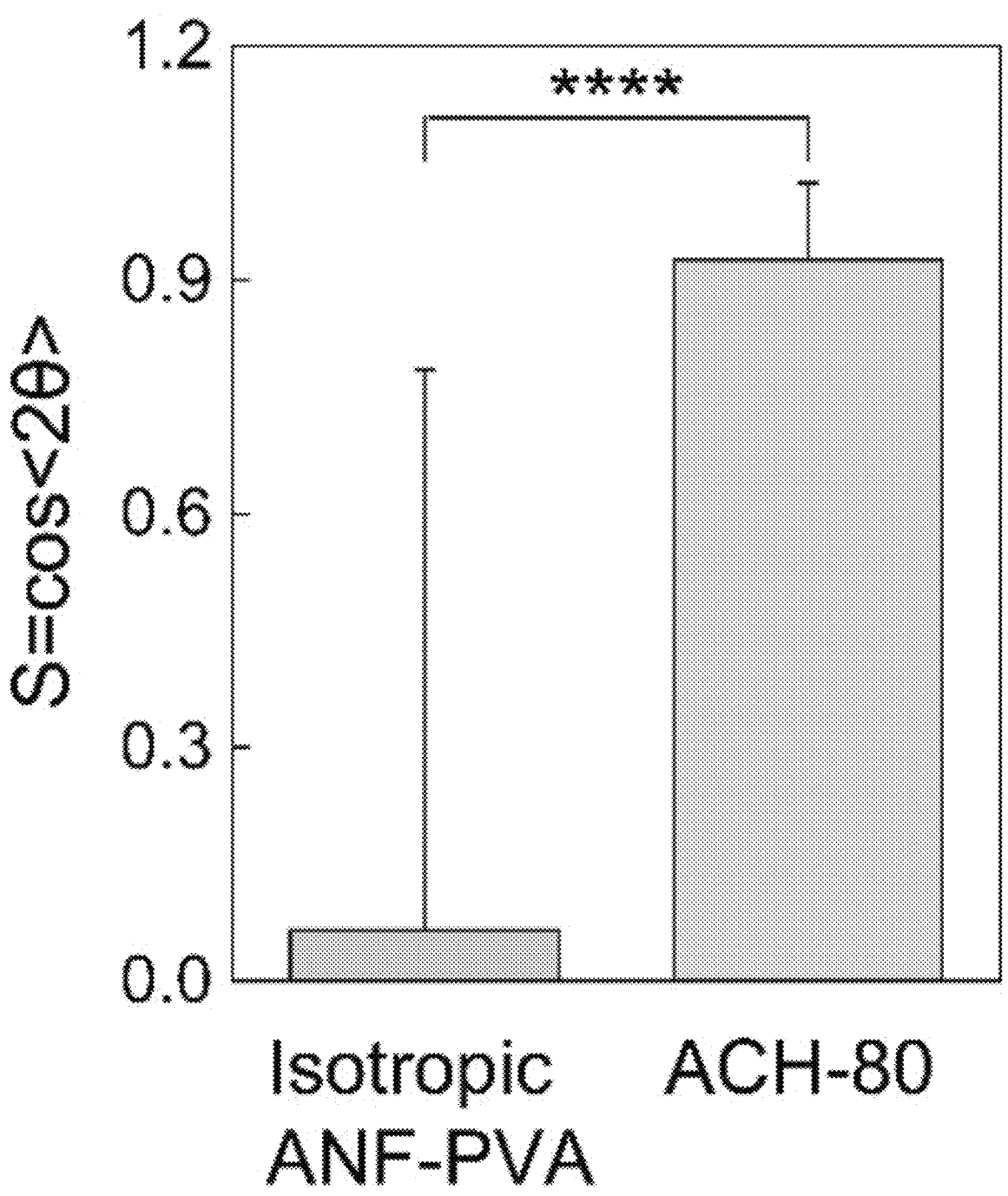

The structural anisotropy of ACHs clearly translated into the morphology of attached cells in certain embodiments. While isotropic ANF-PVA hydrogels led to random arrangement of the attached fibroblasts, embodiments comprising ACHs induced significant orientation of cells, with the degree of orientation increasing with the alignment of fibers (FIG. 3A). The morphology of cells can be regulated by various structural factors of the extracellular matrix (ECM), such anisotropy of stiffness,[24] surface topography[25] or viscoelastic responses.[26] Interestingly, ACHs provide many of these characteristics, which can collectively influence the behaviors of attached cells through mechanosensing and mechanotransduction. Further examinations indicated that self-assembled surface topography is the major contributor for the cell orientation on ACHs. Specifically, both atomic force microscopy (AFM) (FIG. 3B) and optical microscopy (FIG. 18) showed aligned microgrooves on the surface of ACHs with pitch sizes ranging from 0.2 μm to 20 μm, which provide contact guidance for cell orientation.[25] On the other hand, in certain embodiments, removal of the surface topography on ACH with plasma etching led to much less orientation of the attached cells (FIG. 19). It is known that the contractile machinery of cells mediated by Rho-associated protein kinase (ROCK) plays an important role in their morphological responses to surface topography and substrate mechanics.[27] For the fibroblasts cultured on ACHs, adding ROCK inhibitor Y-27623 led to diminished orientation of the cells (FIGS. 20A-20B), which confirmed the mechanosensing and mechanotransduction processes at the cell-ACH interfaces for the anisotropic morphogenesis.

Figure 3C:
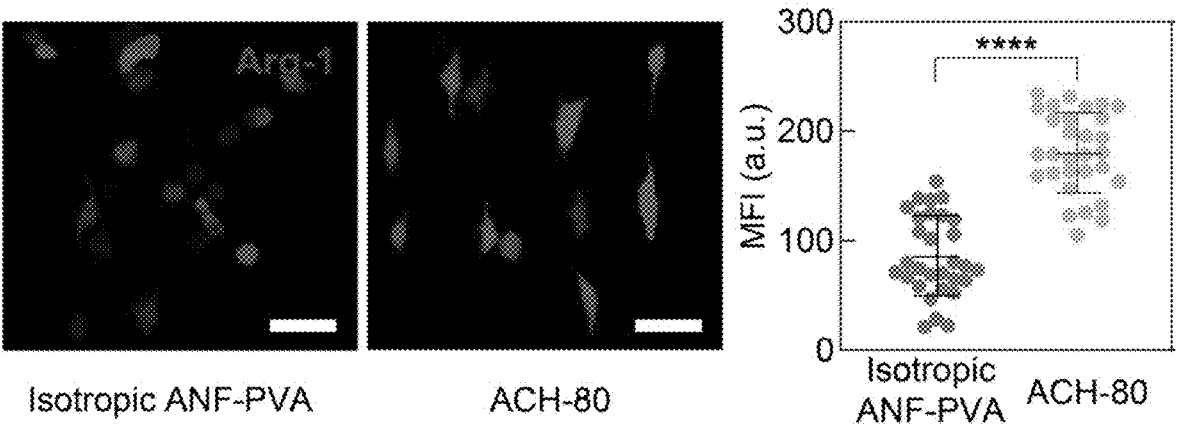
Figure 3D:
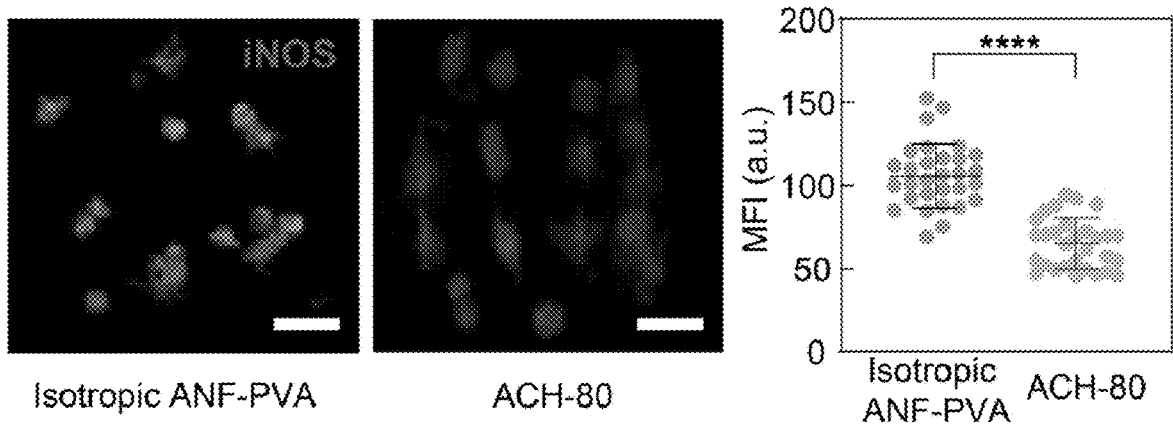

Capabilities in regulating macrophage polarization between pro-inflammatory M1 and pro-healing M2 phenotypes are highly desirable for tissue engineering constructs.[28,29] Recent studies showed that cell-elongation of macrophages due to mechanotransduction can promote their polarization towards M2 phenotype.[30] However, means for controlling macrophage behaviors were rarely demonstrated on a tendon-mimetic materials platform. Embodiments of the subject invention provide anisotropic structural features of ACHs that can influence the morphology of attached macrophages and regulate their polarization. Notably, RAW 264.7 macrophages cultured on ACH-80 exhibit significant orientation and elongation in accordance with the substrate anisotropy, which contrasts with those cultured on isotropic ANF-PVA hydrogels (FIGS. 3C-3D, and FIGS. 21A-21C). The elongation of macrophages enhanced the effect of M2-inducing cytokines interleukin-4 (IL-4) and interleukin-13 (IL-13) added to the cell culture, leading to a higher expression of M2 biomarker Arginase1 (Arg1) as compared with those cultured on isotropic substrates (FIG. 3C). In another experiment, the cell elongation on ACHs counteracted with the applied M1-inducing stimuli interferon-γ (IFNγ) and lipopolysaccharide (LPS), leading to a lower expression of inducible nitric oxide synthase (INOS), a biomarker for M1 (FIG. 3D). These results indicate the capabilities of ACHs in promoting pro-healing M2 phenotype and inhibiting pro-inflammatory M1 phenotype for macrophages, which are indeed advantageous for further applications in implantable devices.

Figure 4A:
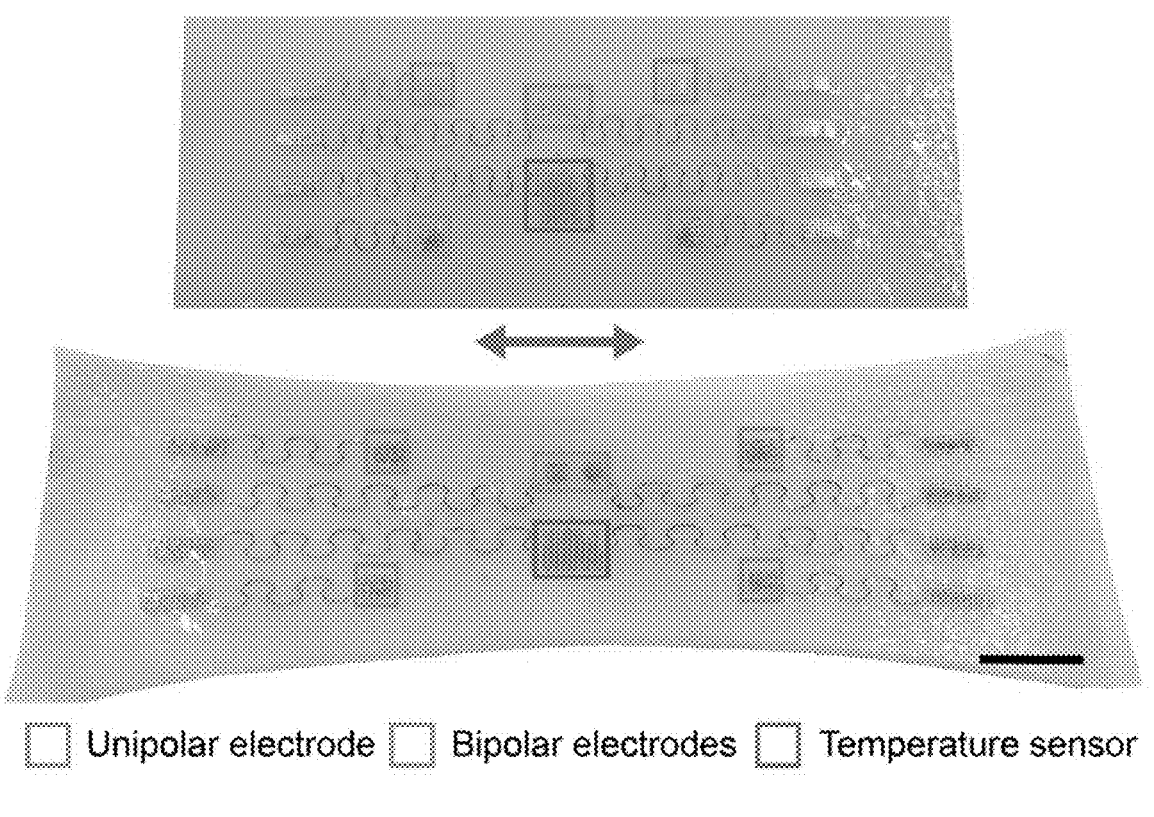
FIGS. 4A-4I illustrate ACHs with integrated multifunctional bioelectronics according to certain embodiments of the subject invention.
Figure 4B:
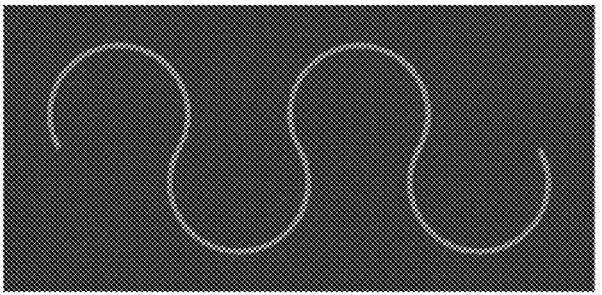
Figure 4B:
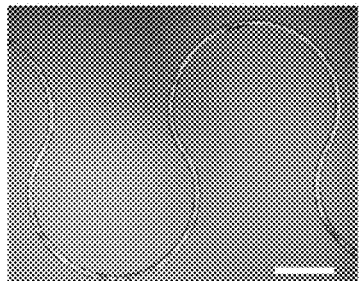
Figure 4C:
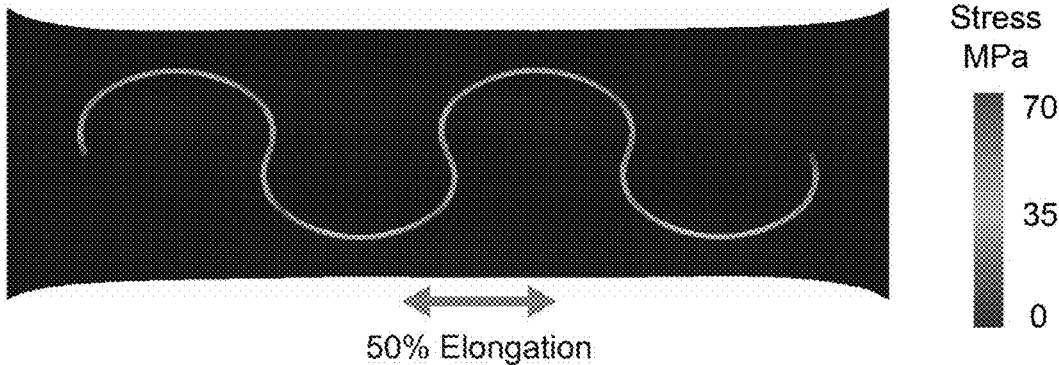
Figure 4D:
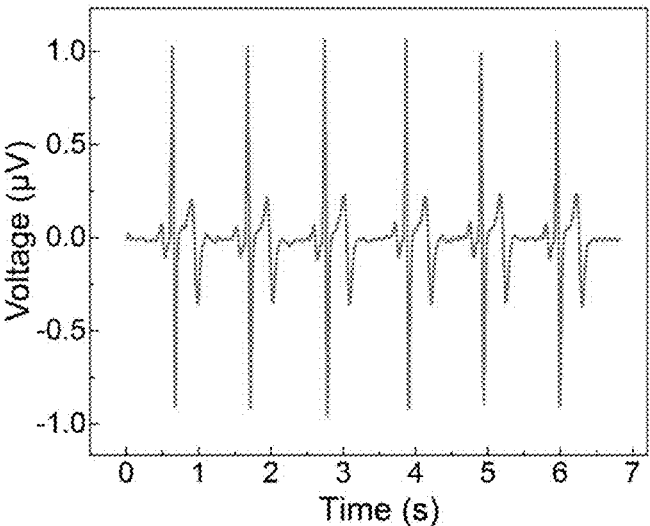
Figure 4E:
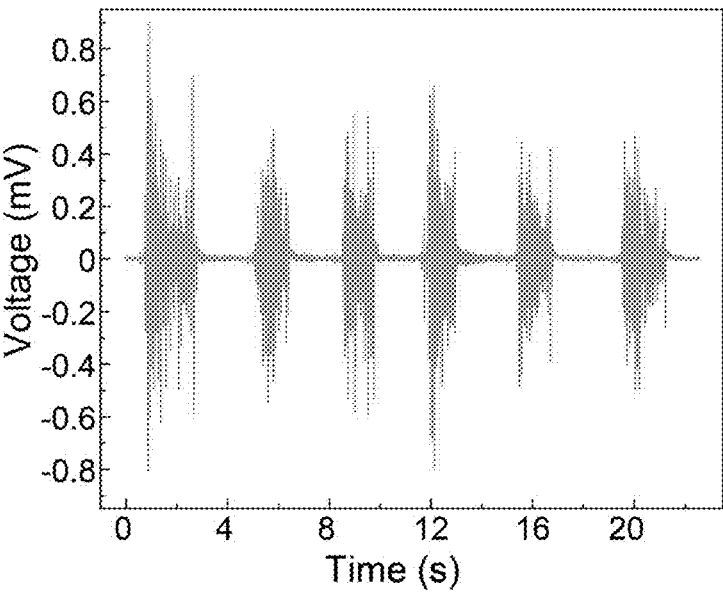
Figure 4F:
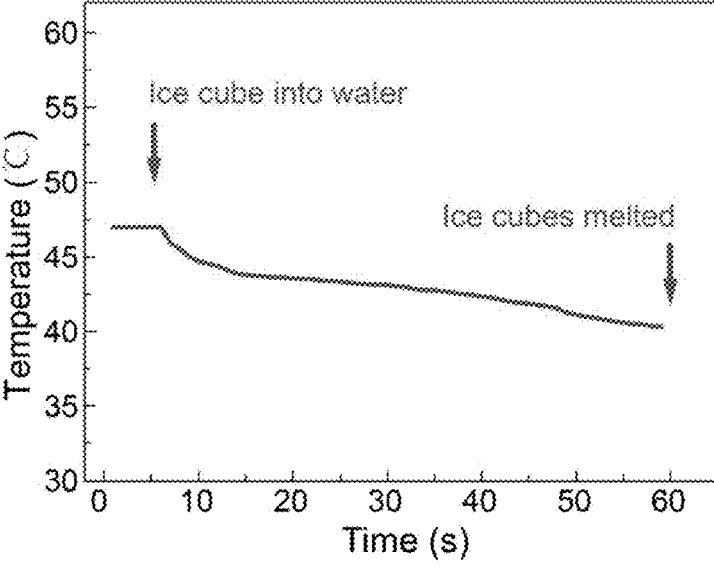
Figure 4G:
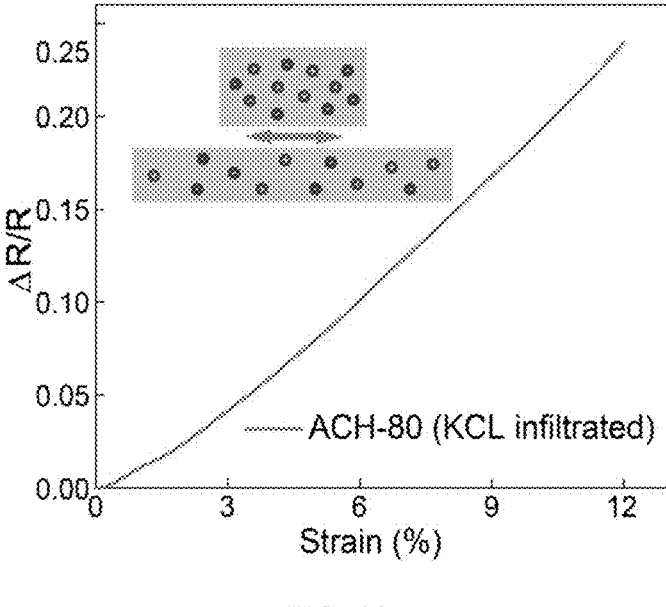
Figure 4H:
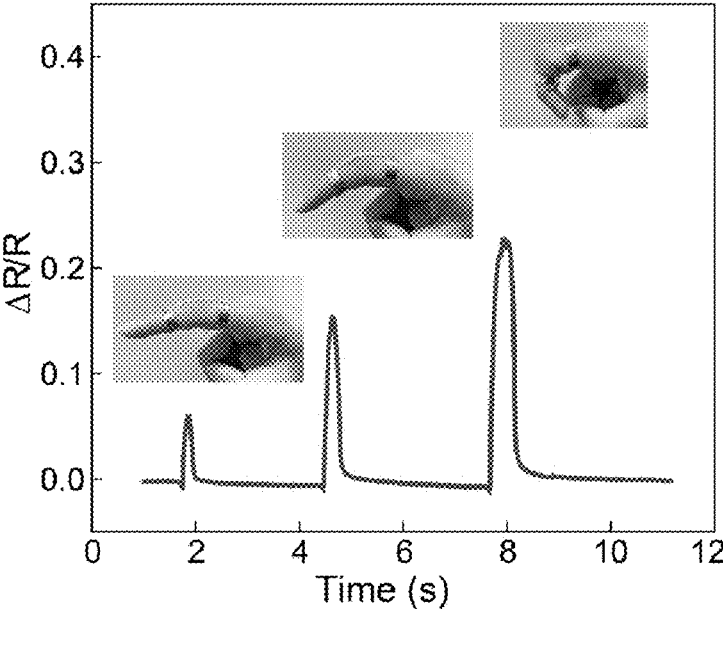
Figure 4I:
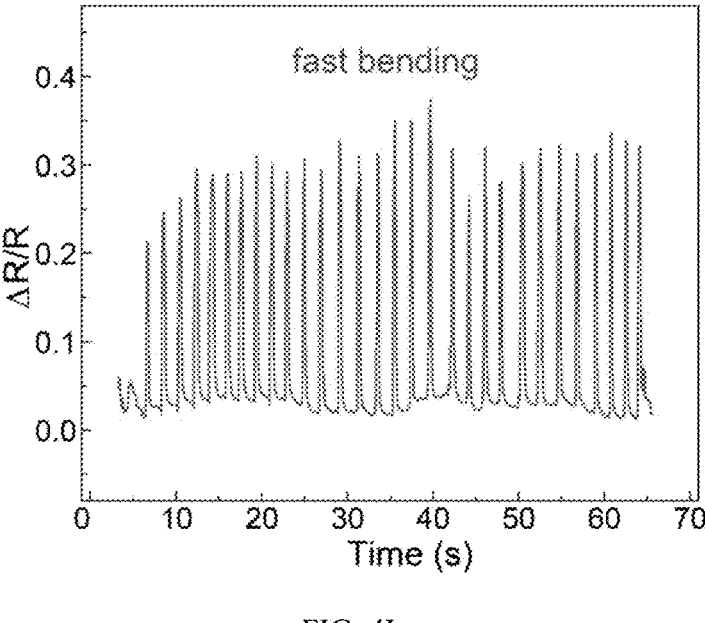
Figure 22:
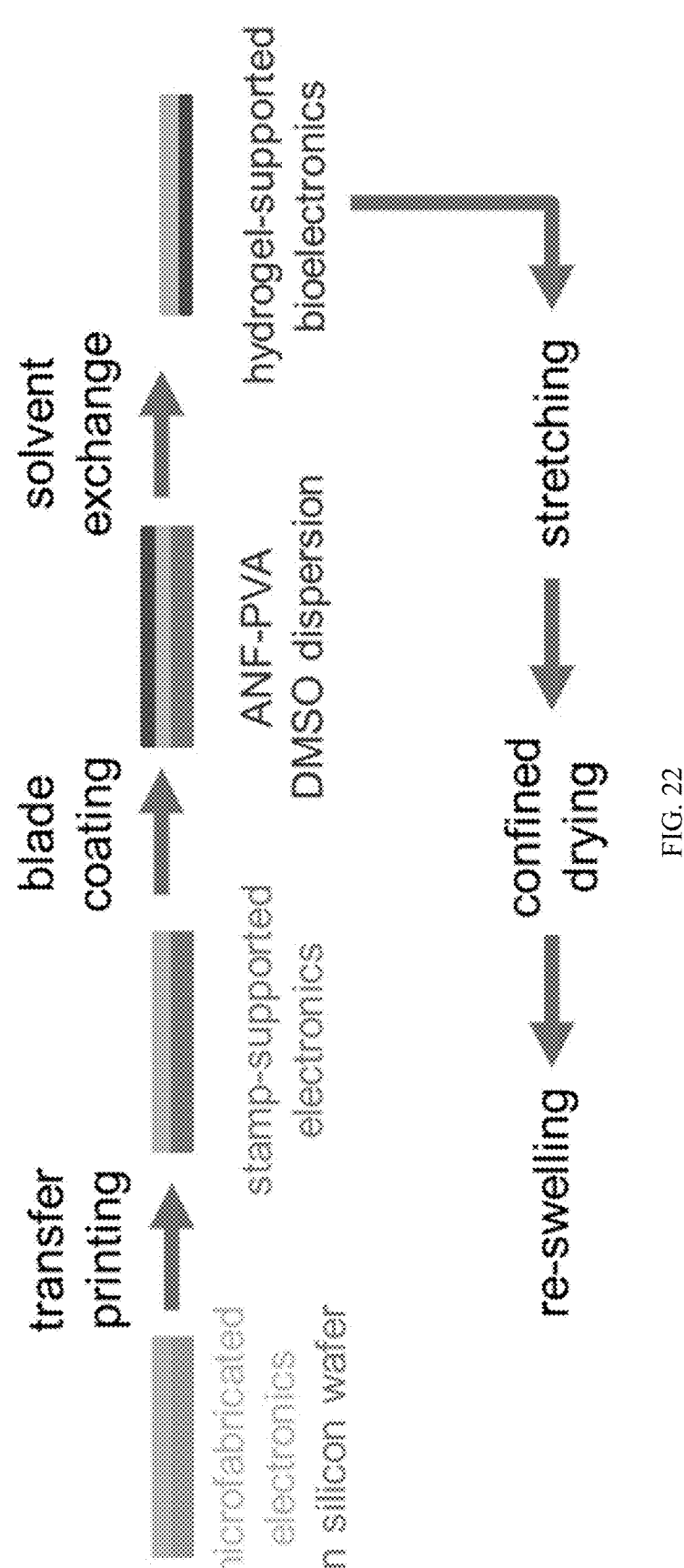
FIG. 22 illustrate fabrication processes for hybrid ACHs with integrated bioelectronics according to certain embodiments of the subject invention. The devices can be microfabricated on a planar wafer and transfer-printed onto ANF-PVA hydrogels via solution processing.
Figure 23:
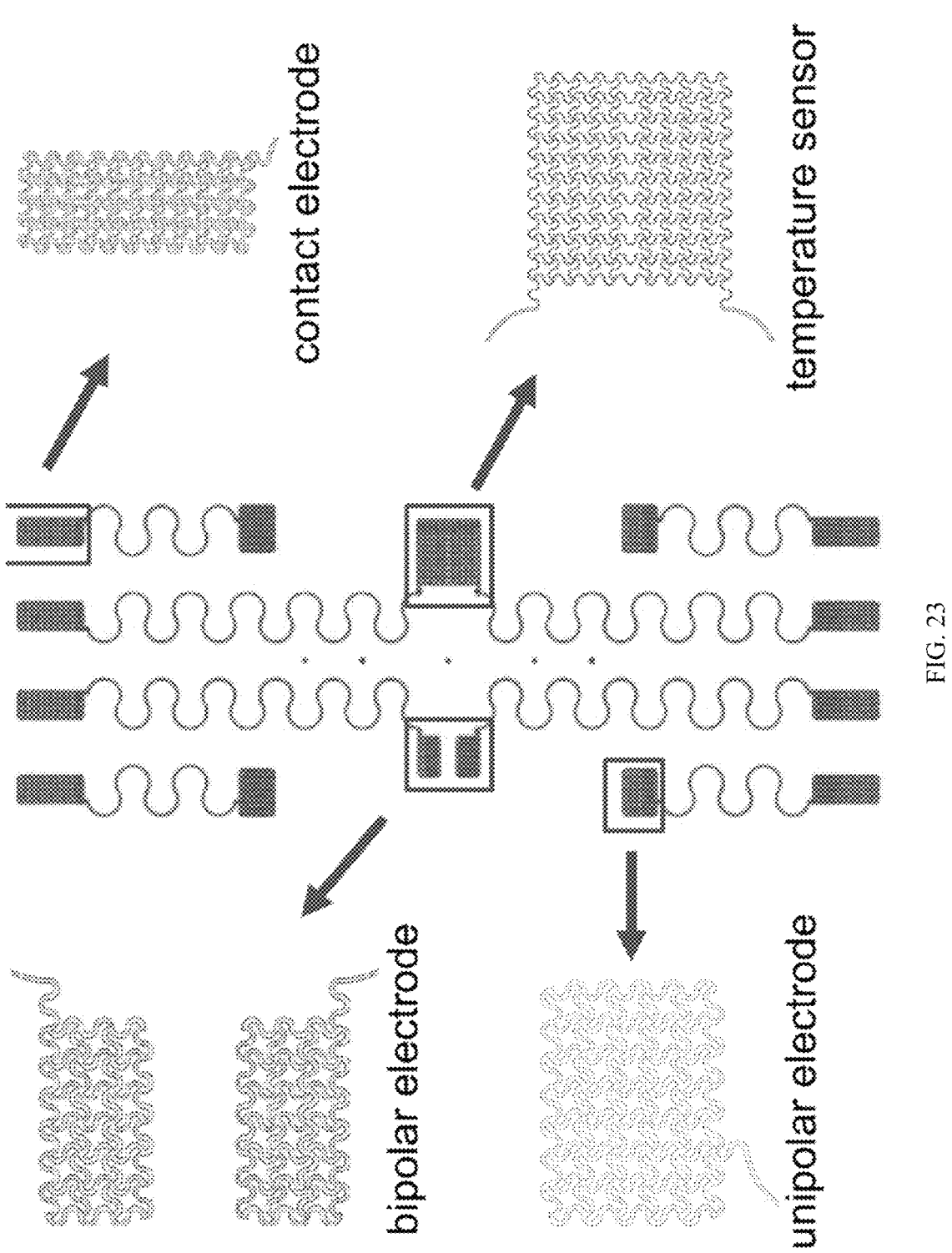
FIG. 23 illustrates the design of multifunctional sensors for the measurement of various physiological signals according to certain embodiments of the subject invention. The array includes bipolar electrodes, unipolar electrodes, temperature sensor and contact pads.
Figure 24A:
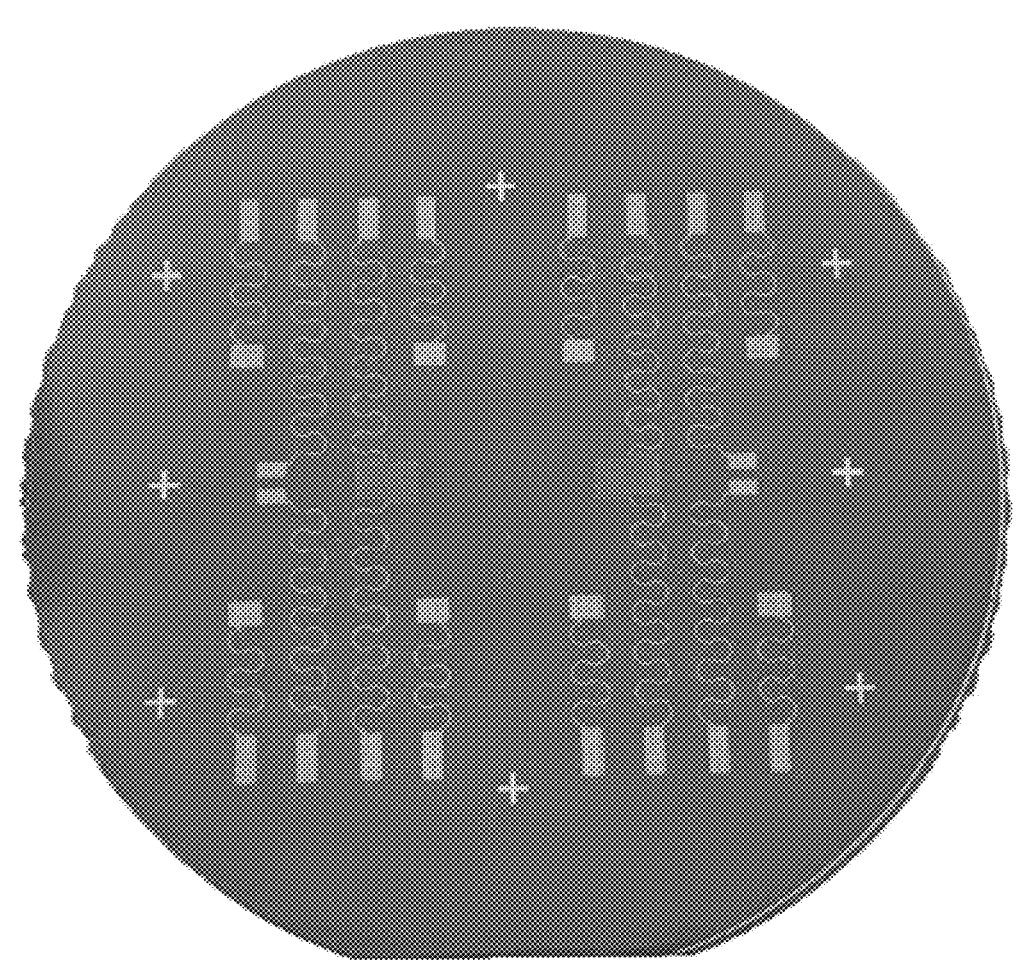
FIG. 24A-24B illustrates serpentine electronics for integration with ACHs according to certain embodiments of the subject invention.
Figure 24B:
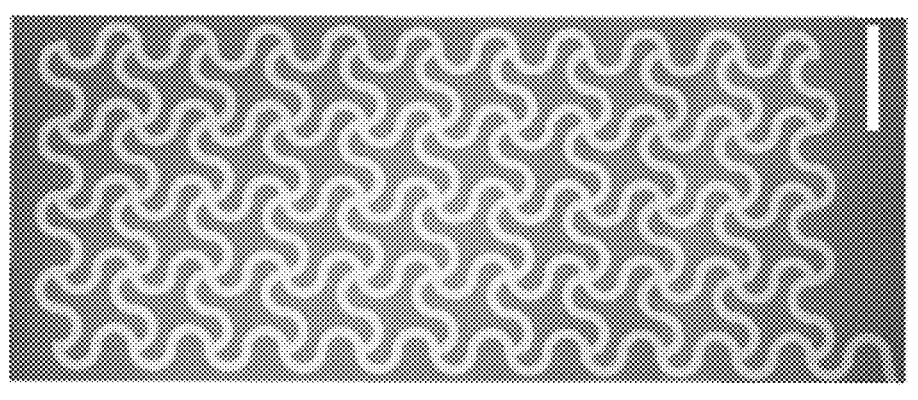
Figure 24B:
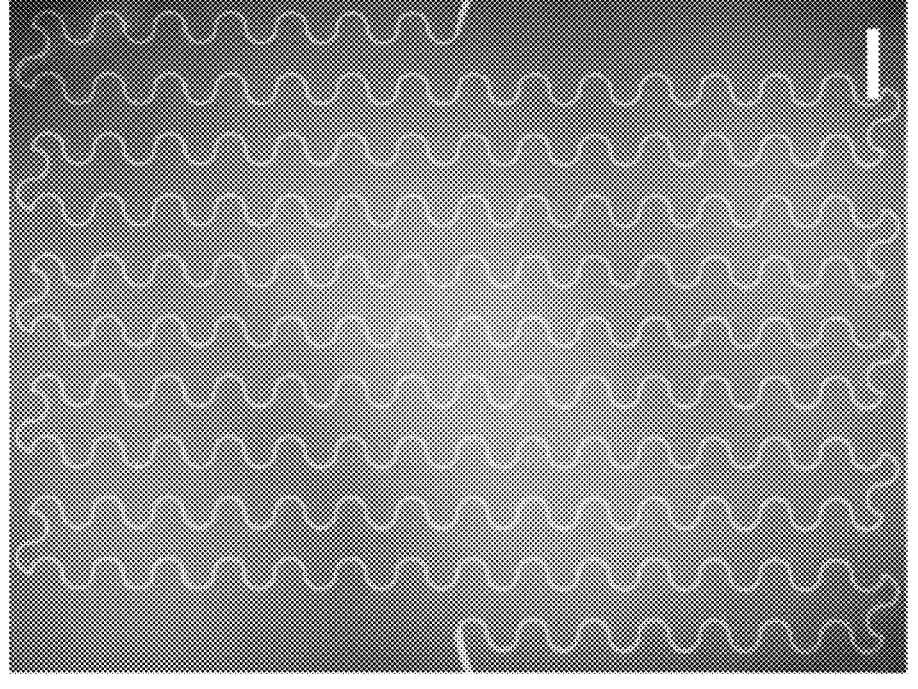
Figure 24B:
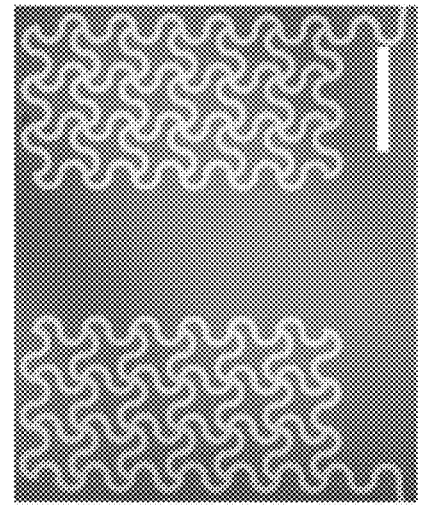
Figure 26A:
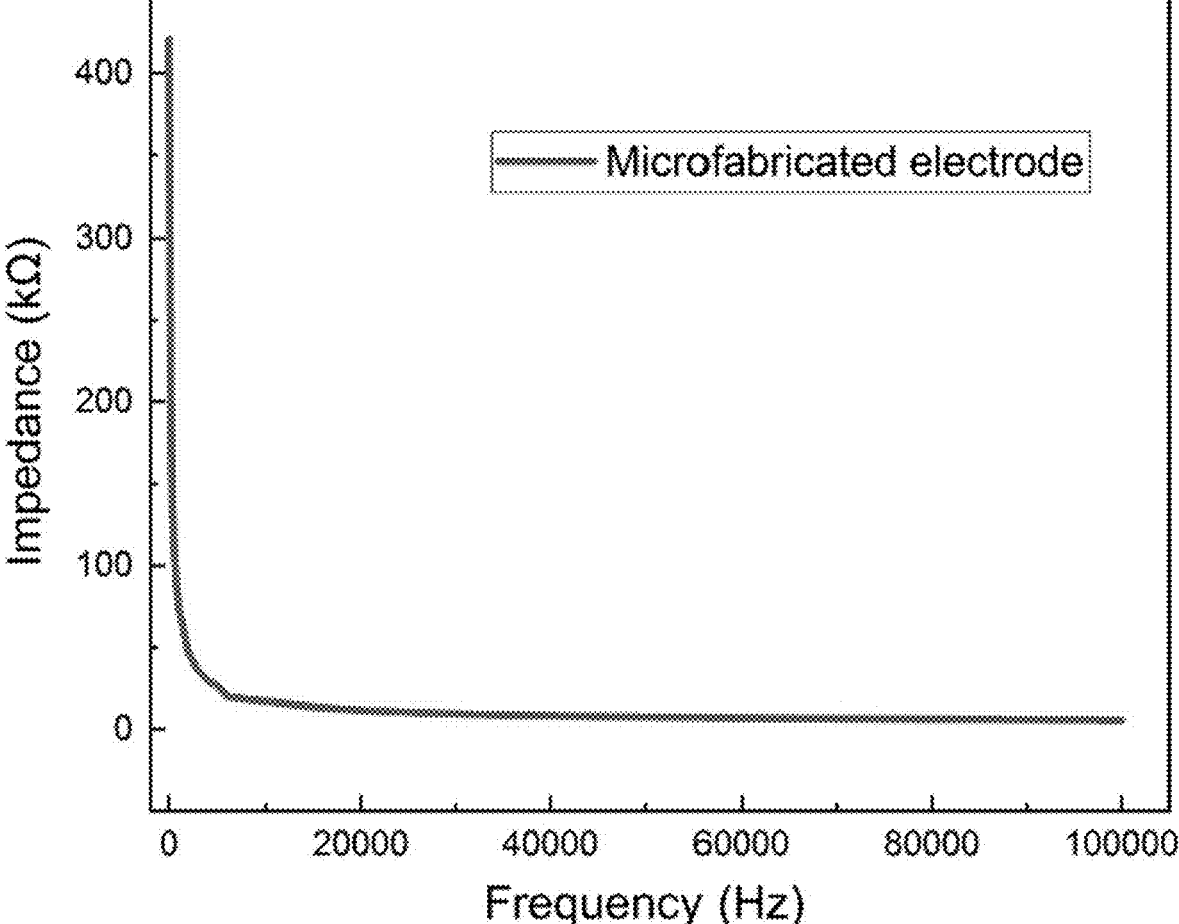
FIG. 26A-26B illustrate characteristics of the bioelectrodes and temperature sensors integrated on ACHs according to certain embodiments of the subject invention.
Figure 26B:
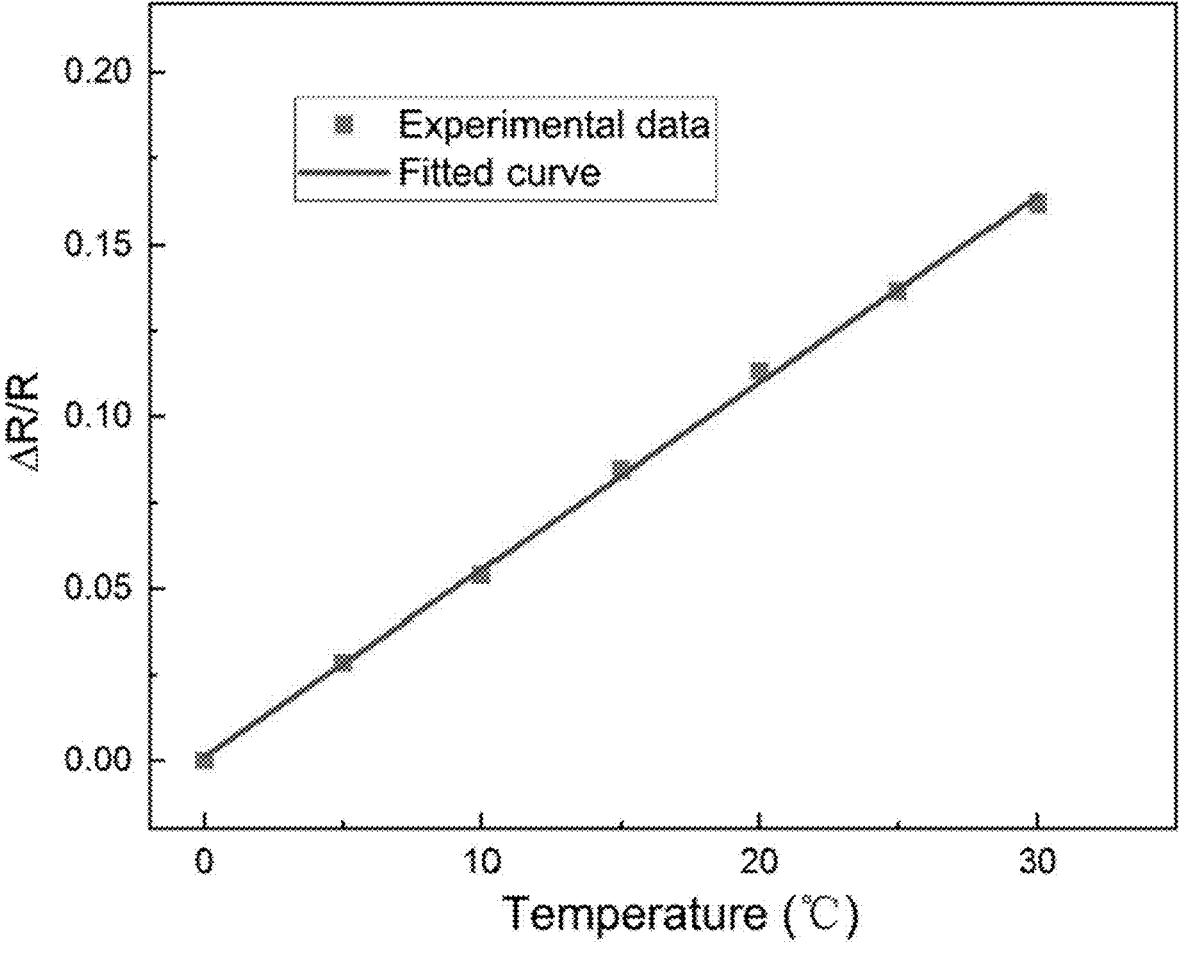

Embodiments provide multimodal physiological sensing with ACH via integrated soft bioelectronics. Specifically, hydroxyl groups on PVA chains in the liquid precursor of ACHs can interact with functionalized surfaces of microfabricated devices (FIG. 22). After solidification by solvent exchange, a stable bonding formed between the ANF-PVA hydrogel and transfer-printed electronic components (FIG. 4A). Serpentine design is provided in certain embodiments for the wafer-fabricated electronics, which imparts high stretchability to withstand the pre-stretching-drying processing for ACHs (FIGS. 23-25). As indicated by finite element analysis (FEA), the stress distributed in a representative serpentine device during 50% of stretching is significantly below the failure threshold of the constituent materials (e.g., polyimide and gold) (FIG. 4B). It is understood within the teachings of the subject invention that the stretchability of the electronic component can be further enhanced by modifying their geometrical designs[31], which can help to retain their mechanical integrity during higher elongation. To demonstrate sensory functions, an array of bioelectrodes on ACHs was used to characterize electrophysiological signals from the skin, leading to high-quality recordings of electrocardiogram (ECG) and electromyogram (EMG) (FIGS. 4D and 4E). Temperature sensors based on encapsulated thin-film resistors exhibited excellent responses even in aqueous media (FIG. 4F and FIGS. 26A-26B), indicating suitability for advantageous applications in an implanted configuration. The above noted functional components on ACHs are only representative, and not limiting, as embodiments may provide additional components and/or circuits as known in the art. Many other biosensors and actuators could be incorporated into various embodiments of this platform due to the versatility of microfabrication and transfer-printing techniques.[32] In one such exemplary embodiment, the inventors engineered a strain sensor based on ionic conductivity of ACHs. Specifically, the electrical resistance of an ACH sample infiltrated with potassium chloride (KCl) increases with imposed elongation, showing a typical gauge factor of ~2.5 (FIG. 4G). This ACH-based sensor is capable of characterizing motion of a joint under various amplitudes (FIG. 4H) and frequencies (FIG. 4I).

Embodiments of the subject invention provide tendon-mimetic hydrogels with outstanding mechanics and functionality originating from the anisotropic assembly of nano-fiber composites. The biophysical cues presented by ACHs can be further utilized for the control of differentiation, migration, and other activities of cells, which helps to expand the toolbox for advanced tissue engineering. In certain embodiments, the set of tendon-mimetic behaviors of ACHs are advantageously applied in applications as implantable tissue prosthetics. Physical integration between ACHs and natural tissues in vivo is contemplated for certain embodiments. Embodiments providing multifunctional bio-electronics integrated on ACHs can provide critically advantageous capabilities for in-situ monitoring of various physiological parameters. Incorporation of wireless modules[33] can enable fully implanted systems that allow two-way communications between external control hardware and the electronically active prosthesis.

Exemplified Embodiments

The invention may be better understood by reference to certain illustrative examples, including but not limited to the following:

Embodiment 1. A tendon-mimetic anisotropic composite hydrogel (ACH) that emulates the microstructural interplay between aligned collagen fibers and soft proteoglycans in native tissues to provide a useful implant for treatment of a patient, the ACH comprising an assembly of highly oriented networks comprising stiff aramid nanofibers (ANFs) and flexible polyvinyl alcohol (PVA) molecules attached thereto by intermolecular hydrogen bonding.

Embodiment 2. The ACH of Embodiment 1, wherein the ACH has a water content between about 60% and about 74%.

Embodiment 3. The ACH of Embodiment 2, wherein the ACH has a primary fiber orientation direction, and the ACH exhibits an elastic modulus greater than or equal to about 490.1 megapascals (MPa) and an ultimate strength greater than or equal to about 52.6 MPa; the elastic modulus and the ultimate strength each, respectively, measured in a direction parallel to the primary fiber orientation direction.

Embodiment 4. The ACH of Embodiment 3, wherein the ACH exhibits an elastic modulus greater than or equal to about 1114 MPa and an ultimate strength greater than or equal to about 72.1 MPa; the elastic modulus and the ultimate strength each, respectively, measured in a direction parallel to the primary fiber orientation direction.

Embodiment 5. The ACH of Embodiment 3, wherein the ACH exhibits a fracture energy greater than about 3 kilojoules per square meter (kJ/m²), measured in a direction parallel to the primary fiber orientation direction; and wherein the ACH exhibits a fracture energy greater than about 3 kJ/m², measured in a direction perpendicular to the primary fiber orientation direction.

Embodiment 6. The ACH of Embodiment 5, wherein the ACH exhibits a fracture energy greater than or equal to about 4 KJ/m², measured in a direction parallel to the primary fiber orientation direction; and wherein the ACH exhibits a fracture energy greater than about 6 kJ/m², measured in a direction perpendicular to the primary fiber orientation direction.

Embodiment 7. The ACH of Embodiment 3, wherein the ACH exhibits a stiffness anisotropy ratio (Ep/En) greater than about 10; wherein the stiffness anisotropy ratio (Ep/En) is calculated between a first respective tensile modulus (Ep) measured parallel to the primary fiber orientation direction, and a second respective tensile modulus (En) measured perpendicular to the primary fiber orientation direction.

Embodiment 8. The ACH of Embodiment 3, wherein the ACH is biofunctionalized, and the ACH exhibits:

an angular frequency distribution with a majority of cells oriented within +/−15 degrees with respect to the primary fiber orientation direction;

a surface topography measurement by atomic force microscope exhibiting a measured height variation equal to or less than about 500 nano meters (nm) over a measurement area of at least about 36 square micrometers ($\mu m^2$);

a statistically significant difference (P<0.05) in mean fluorescent intensity (MFI) for cells having an M1 phenotype when compared to a similarly biofunctionalized isotropic ANF-PVA hydrogel; and a statistically significant difference (P<0.05) in mean fluorescent intensity (MFI) for cells having an M2 phenotype when compared to a similarly biofunctionalized isotropic ANF-PVA hydrogel.

Embodiment 9. The ACH of Embodiment 3, wherein the ACH is fitted with one or more integrated multifunctional bioelectronic circuits configured and adapted to obtain one or more measurements selected from the group consisting of electrocardiogram (ECG), electromyogram (EMG), deformation, strain, temperature, resistance, or voltage under cyclic motion up to 50% elongation of the ACH.

Embodiment 10. A method for creating a tendon-mimetic anisotropic composite hydrogel (ACH) that emulates the microstructural interplay between aligned collagen fibers and soft proteoglycans in native tissues to provide a useful implant for treatment of a patient, the method comprising:

mixing an aramid nanofiber (ANF) in dimethyl sulfoxide (DMSO) and stirring for a time sufficient to produce an ANF dispersion in DMSO;

dissolving polyvinyl alcohol (PVA) in dimethyl sulfoxide (DMSO) and stirring for a time sufficient to produce a PVA dispersion in DMSO;

mixing together the ANF dispersion in DMSO and the PVA dispersion in DMSO to form a moldable composite dispersion;

casting the moldable composite dispersion into one or more molds and immersing in deionized water for a time sufficient to produce an isotropic ANF-PVA hydrogel;

stretching the isotropic ANF-PVA hydrogel to create a stretched hydrogel;

fixing the length of the stretched hydrogel to create a fixed length;

drying the stretched hydrogel at the fixed length to create a dried stretched hydrogel;

reswelling the dried stretched hydrogel to create the ACH.

Embodiment 11. The method of Embodiment 10, wherein the ANF comprises a first mass of para-aramid pulp, and the ANF dispersion in DMSO comprises a second mass of sodium hydroxide (KOH) mixed in the DMSO with the ANF.

Embodiment 12. The method of Embodiment 11, wherein the first mass of para-aramid pulp and the second mass of KOH are about equal in mass.

Embodiment 13. The method of Embodiment 12, wherein the ANF dispersion in DMSO comprises at least about 30 milliliters (mL) of DMSO for every gram (g) of para-aramid pulp.

Embodiment 14. The method of Embodiment 13, wherein the PVA dispersion in DMSO comprises about 15 wt. % PVA.

Embodiment 15. The method of Embodiment 14, wherein the moldable composite dispersion comprises about a 1:1 mass ratio of the ANF dispersion in DMSO and the PVA dispersion in DMSO.

Embodiment 16. The method of Embodiment 15, wherein the dried stretched hydrogel is released from the fixed length prior to reswelling.

Embodiment 17. The method of Embodiment 16, comprising chemical functionalization to present arginylglycylaspartic acid (RGD) motifs for binding with a cell membrane.

Embodiment 18. The method of Embodiment 17, wherein the chemical functionalization comprises benzophenone (BPh) functionalized amphiphilic block copolymers involving linear polyglycerol (LPG) adsorbed on the surface of the ACH in an aqueous environment.

Embodiment 19. The method of Embodiment 15, comprising bonding the isotropic ANF-PVA hydrogel with one or more serpentine electronics circuits to create an integrated soft bioelectronic enabled ACH.

Embodiment 20. A tendon-mimetic anisotropic composite hydrogel (ACH) that emulates the microstructural interplay between aligned collagen fibers and soft proteoglycans in native tissues to provide a useful implant for treatment of a patient, the ACH comprising:

an assembly of highly oriented networks comprising stiff aramid nanofibers (ANFs) and flexible polyvinyl alcohol (PVA) molecules attached thereto by intermolecular hydrogen bonding;

wherein the ACH has a water content between about 60% and about 74%;

wherein the ACH has a primary fiber orientation direction, and the ACH exhibits an elastic modulus greater than or equal to about 1114 megapascals (MPa) and an ultimate strength greater than or equal to about 72.1; the elastic modulus and the ultimate strength, each respectively, measured in a direction parallel to the primary fiber orientation direction;

wherein the ACH exhibits a fracture energy greater than about 4 kilojoules per square meter (kJ/m$^2$), measured in a direction parallel to the primary fiber orientation direction;

wherein the ACH exhibits a fracture energy greater than about 6 KJ/m$^2$, measured in a direction perpendicular to the primary fiber orientation direction;

wherein the ACH exhibits a stiffness anisotropy characterized by the ratio (Ep/En) greater than about 10, wherein the ratio (Ep/En) is calculated between a first respective initial tensile modulus measured parallel (Ep) and a second respective tensile modulus measured substantially perpendicular (En) to the primary fiber orientation direction;

wherein the ACH is biofunctionalized, and the ACH exhibits:

an angular frequency distribution with a majority of cells oriented within +/−15 degrees with respect to the primary fiber orientation direction;

a surface topography measurement by atomic force microscope exhibiting a measured height variation equal to or less than about 500 nano meters (nm) over a measurement area of at least about 36 square micrometers (µm$^2$);

a statistically significant difference (P<0.05) in mean fluorescent intensity (MFI) for cells having an M1 phenotype when compared to a similarly biofunctionalized isotropic ANF-PVA hydrogel; and a statistically significant difference (P<0.05) in mean fluorescent intensity (MFI) for cells having an M2 phenotype when compared to a similarly biofunctionalized isotropic ANF-PVA hydrogel; and wherein the ACH is fitted with one or more integrated multifunctional bioelectronic circuits configured and adapted to obtain one or more measurements selected from the group consisting of electrocardiogram (ECG), electromyogram (EMG), deformation, strain, temperature, resistance, or voltage under cyclic motion up to 50% elongation of the ACH.

Materials and Methods

Fabrication of ACHs.

3.0 g Kevlar para-aramid pulp and 3.0 g KOH were first mixed in 100 mL of dimethyl sulfoxide (DMSO) and then the mixture was magnetically stirred for 7 days at 95° C. to obtain 3 wt. % ANF dispersion. 15.0 g poly (vinyl alcohol) (PVA; 99%+, Mw: 146,000-186,000, Sigma-Aldrich) was dissolved in 100 mL of DMSO and magnetically stirred for 3 days to obtain 15 wt. % PVA solution. ANF dispersion in DMSO and PVA solution in DMSO were mixed with 1:1 mass ratio for the liquids, and then casted in molds and immersed in deionized water for over 24 h to obtain ANF-PVA hydrogels. Isotropic ANF-PVA hydrogels were stretched with various elongation levels and dried in atmosphere for 20 h with the length in the stretching direction fixed. After drying, the samples were released from the loading and reswelled in deionized water for 24 h. Water/solid contents of samples were determined by the weight differences between hydrogels and their fully dehydrated states after baking in a 100° C. vacuum oven for 24 h.

SEM and AFM Characterization.

Scanning electron microscope (SEM Hitachi S4800 FEG) was employed to observe the surfaces and cross-sections of the hydrogels. The samples for SEM examination were prepared by a solvent exchange in ethanol and critical point drying (CPD, Tousimis Autosamdri 931). The hydrogel samples were frozen in liquid nitrogen and mechanically fractured to expose the cross- and longitudinal-sections for examination. Atomic force microscopy (AFM; Bruker Nanowizard4 XP) was employed to observe surface topography of biofunctionalized hydrogels in an aqueous environment. Silicon nitride probes (SCANASYST-FLUID, BRUKER) were used for the characterization.

Mechanical Testing.

To carry out tensile tests, hydrogels were cut in a dumbbell shape and tested at room temperature by a mechanical tester (Zwick Roell) with a fixed strain rate of 100% per minute. Samples for tearing test were cut into a trouser shape and the two arms of hydrogels were then clamped on the mechanical tester and stretched with a fixed test velocity of 1.7 mm/s. The fracture energy I' was calculated by I'=2F/b, where F is the averaged steady state tearing force and b is the thickness of samples. For the measurement of the stress-relaxation properties of hydrogels, the samples were stretched to various strain levels with a fixed deformation rate 100% per minute, and the strain was retained for 60 s. The initial modulus was determined as the slope of the stress-strain curve under 2% of tensile strain.

Surface Functionalization.

RGD functionalized amphiphilic block copolymers (benzophenone functionalized linear polyglycerol, LPG-BPh) solution (1 mg/mL) was applied onto the surface of ANF-PVA hydrogels, and then rested for 30 min for adsorption. Then the coated hydrogel surface was illuminated with UV irradiation for 15 minutes, allowing grafting of LPG-BPh on PVA and crosslinking between LPG-BPh. The thickness of the coating is estimated as 3 nm 34.34 After rinsing with phosphate buffered saline (PBS), the substrate is ready for cell growth.

Fibroblasts Culture and Immunofluorescence Staining.

Fibroblasts (NIH-3T3 cells) were cultured in Dulbecco's modified Eagle's Medium (DMEM) with 10% fetal bovine and 1% penicillin/streptomycin (all from Thermo Fisher). The hydrogels were soaked in PBS (Thermo Fisher) for 24 h and then sterilized by UV overnight. NIH-3T3 cells were seeded on the hydrogels in 24-well plates with a density of $2 \times 10^4$ cells/well and cultured for 24 h. To evaluate the effect of ROCK, fibroblasts were cultured on hydrogels within the media containing the various concentrations of Y-27632 overnight.

The morphology of fibroblasts was observed by fluorescent staining. After cultured for 24 h, cells were fixed by 4% paraformaldehyde (Aladdin) for 15 minutes at room temperature and then permeabilized with 0.25% Triton X-100 (Aladdin, diluted with PBS) for 10 min and blocked by 1% bovine serum albumin (Thermo Fisher) for 1 hour. Subsequently, the cytoskeleton of fibroblasts was stained with Phalloidin-iFluor 488 Reagent (Abcam, 1:1000, diluted with PBS) at 4° C. overnight. The fibroblasts were observed with a laser scanning confocal microscope (Nikon Instruments Inc., Japan).

Macrophage Culture and Polarization.

Mouse macrophages (RAW 264.7) were purchased from American Type Culture Collection. Cells were seeded on the hydrogels in 24-well plates with the density of $2 \times 10^4$ cells/well and incubated for 24 h prior to stimulation. Then the incubation media were replaced by media containing IFN$\gamma$ (20 ng/ml)/LPS (100 ng/ml) or IL-4 (40 ng/ml)/IL-13 (200 ng/ml) for 24 h.

Macrophage Immunofluorescence Staining.

RAW 264.7 macrophages on various hydrogels were fixed and permeabilized with the same method described above for the fibroblasts. After that, cells were further stained with iNOS Monoclonal Antibody (CXNFT), Alexa Fluor™ 488, eBioscience™ (Thermo Fisher, 1:100, diluted with PBS) and Arginase 1 Monoclonal Antibody (AlexF5), Alexa Fluor™ 488, eBioscience™ (Thermo Fisher, 1:50, diluted with PBS). The cells were observed with a laser scanning confocal microscope (Nikon Instruments Inc., Japan).

Analysis of Cell Orientation and Mean Fluorescence Intensity.

Image J software was used to draw cell outline manually, which helps to determine the length of a cell's main axis (L) and orientation angle ($\theta$) (defined as the angle between the main axis of cell and the pre-stretching direction for ACHs). Furthermore, orientation index (S) was determined by the equation: $S = \cos(2\theta)$. The mean fluorescent intensity (MFI) of each cell was calculated from the total fluorescence intensity of a whole cell divided by the cell area. Statistics were based on measurements for at least 30 cells.

Statistical Analysis.

Data were presented as mean values±SD of at least five tests, unless otherwise indicated. An unpaired Student's t-test was used to evaluate the statistical significance of the variance and $P < 0.05$ was considered statistically significant.

Fabrication of Anisotropic Hydrogel Integrated with Electronics.

Poly (methyl methacrylate) (PMMA) (Sigma-Aldrich) was first spin-coated on a 4-inch silicon wafer, followed by spin coating and curing of a layer of polyimide (PI) (Sigma-Aldrich). Then, the top of the PI layer was deposited with chromium (Cr, 5 nm) and gold (Au, 50 nm) by sputtering (Denton Desktop Pro). Photolithography was done with photoresist AZ 5214 and mask aligner URE-2000/35L. Through wet etching, the 1st metal layer (temperature sensors) was fabricated. Using the same method, the 2nd metal layer (5 nm Cr and 200 nm Au) was deposited and patterned through photolithography and wet etching to obtain unipolar electrodes, bipolar electrodes, and interconnects. Another layer of PI was applied and patterned by reactive ion etching (RIE, Tailong Electronics). PMMA was completely dissolved in acetone overnight and the microfabricated devices were picked up with water-soluble PVA tapes leading to stamp-supported devices. To enable the robust adhesion with hydrogels, the devices were treated with RIE to create additional functional groups on the polymer surface. Then the well-mixed ANF-PVA in DMSO was blade-coated on the top of the stamp-supported devices. After coating, the whole device was submerged in DI water for releasing the tape and solidifying the ANF-PVA hydrogel. The hydrogel samples bonded with serpentine electronics were processed with stretching, confined drying and reswelling in DI water to obtain hybrid ACHs.

When ranges are used herein, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e., the value can be +/−5% of the stated value. For example, "about 1 meter" means from 0.95 meters to 1.05 meters.

The transitional term "comprising," "comprises," or "comprise" is inclusive or open-ended and does not exclude additional, unrecited elements or method steps. By contrast, the transitional phrases "consisting of" or "consists of" exclude any element, step, or ingredient not specified in the claim. The phrases "consisting essentially of" or "consists essentially of" indicate that the claim encompasses embodiments containing the specified materials or steps and those that do not materially affect the basic and novel characteristic(s) of the claim. Use of the term "comprising" contemplates other embodiments that "consist of" or "consist essentially of" the recited component(s).

All patents, patent applications, provisional applications, and publications referred to or cited herein are incorporated by reference in their entirety, including all figures and tables, to the extent they are not inconsistent with the explicit teachings of this specification.

The preceding examples illustrate procedures for practicing the invention. These examples should not be construed as limiting. All percentages are by weight and all solvent mixture proportions are by volume unless otherwise noted.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Guimarães, C. F., Gasperini, L., Marques, A. P. & Reis, R. L. The stiffness of living tissues and its implications for tissue engineering. *Nat. Rev. Mater.* 5, 351-370 (2020).
2. Li, H., Liu, H., Sun, M., Huang, Y. & Xu, L. 3D Interfacing between Soft Electronic Tools and Complex Biological Tissues. *Adv. Mater.* 33, 2004425 (2020).
3. Matson, A., Konow, N., Miller, S., Konow, P. P. & Roberts, T. J. Tendon material properties vary and are interdependent among turkey hindlimb muscles. *J. Exp. Biol.* 215, 3552-3558 (2012).
4. Jung, H.-J., Fisher, M. B. & Woo, S. L. Y. Role of biomechanics in the understanding of normal, injured, and healing ligaments and tendons. *BMC Sports Sci. Med. Rehabil.* 1, 9 (2009).
5. Wang, J. H.-C. Mechanobiology of tendon. *J. Biomech.* 39, 1563-1582 (2006).
6. Zhang, Y. et al. Molecular insights into the complex mechanics of plant epidermal cell walls. *Science.* 372, 706-711 (2021).
7. Choi, S., Choi, Y. & Kim, J. Anisotropic hybrid hydrogels with superior mechanical properties reminiscent of tendons or ligaments. *Adv. Funct. Mater.* 29, 1904342 (2019).
8. Lin, S., Liu, J., Liu, X. & Zhao, X. Muscle-like fatigue-resistant hydrogels by mechanical training. *Proc. Natl. Acad. Sci.* 116, 10244-10249 (2019).
9. Zou, J. et al. Highly Efficient and Environmentally Friendly Fabrication of Robust, Programmable, and Biocompatible Anisotropic, All-Cellulose, Wrinkle-Patterned Hydrogels for Cell Alignment. *Adv. Mater.* 31, 1904762 (2019).
10. Yang, W., Furukawa, H. & Gong, J. P. Highly extensible double-network gels with self-assembling anisotropic structure. *Adv. Mater.* 20, 4499-4503 (2008).
11. Sun, J.-Y. et al. Highly stretchable and tough hydrogels. *Nature* 489, 133-136 (2012).
12. Sun, T. L. et al. Physical hydrogels composed of polyampholytes demonstrate high toughness and viscoelasticity. *Nat. Mater.* 12, 932-937 (2013).
13. Hua, M. et al. Strong tough hydrogels via the synergy of freeze-casting and salting out. *Nature* 590, 594-599 (2021).
14. Guo, Y. Z. et al. Facile preparation of cellulose hydrogel with Achilles tendon-like super strength through aligning hierarchical fibrous structure. *Chem. Eng. J.* 428, 132040 (2022).
15. Kong, W. et al. Muscle-inspired highly anisotropic, strong, ion-conductive hydrogels. *Adv. Mater.* 30, 1801934 (2018).
16. No, Y. J. et al. High-strength fiber-reinforced composite hydrogel scaffolds as biosynthetic tendon graft material. *ACS Biomater. Sci. Eng.* 6, 1887-1898 (2020).
17. Huang, Y. et al. Superior fracture resistance of fiber reinforced polyampholyte hydrogels achieved by extraordinarily large energy-dissipative process zones. *J. Mater. Chem. A* 7, 13431-13440 (2019).
18. Xu, L., Zhao, X., Xu, C. & Kotov, N. A. Water-Rich Biomimetic Composites with Abiotic Self-Organizing Nanofiber Network. *Adv. Mater.* 30, 1703343 (2018).
19. Mredha, M. T. I. et al. Hydrogels: A Facile Method to Fabricate Anisotropic Hydrogels with Perfectly Aligned Hierarchical Fibrous Structures (Adv. Mater. 9/2018). *Adv. Mater.* 30, 1870060 (2018).
20. Hoffmeister, B. K., Handley, S. M., Wickline, S. A. & Miller, J. G. Ultrasonic determination of the anisotropy of Young's modulus of fixed tendon and fixed myocardium. *J. Acoust. Soc. Am.* 100, 3933-3940 (1996).
21. Lynch, H. A., Johannessen, W., Wu, J. P., Jawa, A. & Elliott, D. M. Effect of fiber orientation and strain rate on the nonlinear uniaxial tensile material properties of tendon. *J. Biomech. Eng.* 125, 726-731 (2003).
22. Chaudhuri, O., Cooper-White, J., Janmey, P. A., Mooney, D. J. & Shenoy, V. B. Effects of extracellular matrix viscoelasticity on cellular behaviour. *Nature* 584, 535-546 (2020).
23. Yu, L. et al. Ligand diffusion enables force-independent cell adhesion via activating a5ß1 integrin and initiating rac and RhoA signaling. *Adv. Mater.* 32, 2002566 (2020).
24. Saez, A., Ghibaudo, M., Buguin, A., Silberzan, P. & Ladoux, B. Rigidity-driven growth and migration of epithelial cells on microstructured anisotropic substrates. *Proc. Natl. Acad. Sci.* 104, 8281-8286 (2007).
25. Charest, J. L., García, A. J. & King, W. P. Myoblast alignment and differentiation on cell culture substrates with microscale topography and model chemistries. *Biomaterials* 28, 2202-2210 (2007).
26. Gong, Z. et al. Matching material and cellular timescales maximizes cell spreading on viscoelastic substrates. *Proc. Natl. Acad. Sci.* 115, E2686-E2695 (2018).
27. Seo, C. H., Furukawa, K., Montagne, K., Jeong, H. & Ushida, T. The effect of substrate microtopography on focal adhesion maturation and actin organization via the RhoA/ROCK pathway. *Biomaterials* 32, 9568-9575 (2011).
28. Zhu, Y. et al. Regulation of macrophage polarization through surface topography design to facilitate implant-to-bone osteointegration. *Sci. Adv.* 7, eabf6654 (2021).
29. Hu, J. et al. Mechanically active adhesive and immune regulative dressings for wound closure. *Matter* 4, 2985-3000 (2021).
30. Mcwhorter, F. Y., Wang, T., Nguyen, P., Chung, T. & Liu, W. F. Modulation of macrophage phenotype by cell shape. *Proc. Natl. Acad. Sci.* 110, 17253-17258 (2013).
31. Fan, J. A. et al. Fractal design concepts for stretchable electronics. *Nat. Commun.* 5, 3266 (2014).
32. Xu, L. et al. 3D multifunctional integumentary membranes for spatiotemporal cardiac measurements and stimulation across the entire epicardium. *Nat. Commun.* 5, 3329 (2014).
33. Koo, J. et al. Wireless bioresorbable electronic system enables sustained nonpharmacological neuroregenerative therapy. *Nat. Med.* 24, 1830-1836 (2018).
34. Yu, L. et al. High-antifouling polymer brush coatings on nonpolar surfaces via adsorption-cross-linking strategy. *ACS Appl. Mater. Interfaces* 9, 44281-44292 (2017).
la Vergari, C. et al. Axial speed of sound is related to tendon's nonlinear elasticity. *J. Biomech.* 45, 263-268 (2012).
2a Wang, J. H. Mechanobiology of tendon. J. Biomech. 39, 1563-1582, (2006).

3a Purslow, P. P., Wess, T. J. & Hukins, D. W. Collagen orientation and molecular spacing during creep and stress-relaxation in soft connective tissues. J. Exp. Biol. 201, 135-142, (1998).

4a Hua, M. et al. Strong tough hydrogels via the synergy of freeze-casting and salting out. Nature 590, 594-599, (2021).

5a Lin, S., Liu, J., Liu, X. & Zhao, X. Muscle-like fatigue-resistant hydrogels by mechanical training. Proc Natl Acad Sci USA 116, 10244-10249, (2019).

6a Zou, J. et al. Highly Efficient and Environmentally Friendly Fabrication of Robust, Programmable, and Bio-compatible Anisotropic, All-Cellulose, Wrinkle-Patterned Hydrogels for Cell Alignment. Adv. Mater. 31, e1904762, (2019).

7a Yang, W., Furukawa, H. & Gong, J. P. Highly Extensible Double-Network Gels with Self-Assembling Anisotropic Structure. Adv. Mater. 20, 4499-4503, (2008).

8a Kong, W. et al. Muscle-Inspired Highly Anisotropic, Strong, Ion-Conductive Hydrogels. Adv. Mater. 30, e1801934, (2018).

9a Mredha, M. T. I. et al. A Facile Method to Fabricate Anisotropic Hydrogels with Perfectly Aligned Hierarchical Fibrous Structures. Adv. Mater. 30, e1704937, (2018).

10a Quapp, K. M. & Weiss, J. A. Material Characterization of Human Medial Collateral Ligament. Journal of Bio-mechanical Engineering 120, 757-763, (1998).

11a Jung, H. J., Fisher, M. B. & Woo, S. L. Role of biomechanics in the understanding of normal, injured, and healing ligaments and tendons. Sports Med. Arthrosc. Rehabil. Ther. Technol. 1, 9, (2009).

12a Wren, T. A. L., Yerby, S. A., Beaupré, G. S. & Carter, D. R. Mechanical properties of the human achilles tendon. Clin. Biomech. 16, 245-251, (2001).

13a Johnson, G. A. et al. Tensile and viscoelastic properties of human patellar tendon. J. Orth. Res. 12, 796-803, (1994).

14a Matson, A., Konow, N., Miller, S., Konow, P. P. & Roberts, T. J. Tendon material properties vary and are interdependent among turkey hindlimb muscles. J. Exp. Biol. 215, 3552-3558, (2012).

We claim:

1. A tendon-mimetic anisotropic composite hydrogel (ACH) that emulates the microstructural interplay between aligned collagen fibers and soft proteoglycans in native tissues to provide a useful implant for treatment of a patient, the ACH comprising an assembly of stiff aramid nanofibers (ANFs) and flexible polyvinyl alcohol (PVA) molecules attached thereto by intermolecular hydrogen bonding.

2. The ACH of claim 1, wherein the ACH has a water content between about 60% and about 74% by weight.

3. The ACH of claim 2, wherein the ACH has a primary fiber orientation direction, and the ACH exhibits an elastic modulus greater than or equal to about 490.1 megapascals (MPa) and an ultimate strength greater than or equal to about 52.6 MPa; the elastic modulus and the ultimate strength each, respectively, measured in a direction parallel to the primary fiber orientation direction.

4. The ACH of claim 3, wherein the ACH exhibits an elastic modulus greater than or equal to about 1114 MPa and an ultimate strength greater than or equal to about 72.1 MPa; the elastic modulus and the ultimate strength each, respectively, measured in a direction parallel to the primary fiber orientation direction.

5. The ACH of claim 3, wherein the ACH exhibits a fracture energy greater than about 3 kilojoules per square meter (kJ/m$^2$), measured in a direction parallel to the primary fiber orientation direction; and wherein the ACH exhibits a fracture energy greater than about 3 KJ/m$^2$, measured in a direction perpendicular to the primary fiber orientation direction.

6. The ACH of claim 5, wherein the ACH exhibits a fracture energy greater than or equal to about 4 KJ/m$^2$, measured in a direction parallel to the primary fiber orientation direction; and wherein the ACH exhibits a fracture energy greater than about 6 KJ/m$^2$, measured in a direction perpendicular to the primary fiber orientation direction.

7. The ACH of claim 3, wherein the ACH exhibits a stiffness anisotropy ratio (Ep/En) greater than about 10; wherein the stiffness anisotropy ratio (Ep/En) is calculated between a first respective tensile modulus (Ep) measured parallel to the primary fiber orientation direction, and a second respective tensile modulus (En) measured perpendicular to the primary fiber orientation direction.

8. The ACH of claim 3, wherein the ACH is biofunctionalized, and the ACH exhibits:

an angular frequency distribution with a majority of cells oriented within +/−15 degrees with respect to the primary fiber orientation direction;

a surface topography measurement by atomic force microscope exhibiting a measured height variation equal to or less than about 500 nano meters (nm) over a measurement area of at least about 36 square micrometers (μm$^2$);

a statistically significant difference (P<0.05) in mean fluorescent intensity (MFI) for cells having an M1 phenotype when compared to a similarly biofunctionalized isotropic ANF-PVA hydrogel; and a statistically significant difference (P<0.05) in mean fluorescent intensity (MFI) for cells having an M2 phenotype when compared to a similarly biofunctionalized isotropic ANF-PVA hydrogel.

9. The ACH of claim 3, wherein the ACH is fitted with one or more integrated multifunctional bioelectronic circuits configured and adapted to obtain one or more measurements selected from the group consisting of electrocardiogram (ECG), electromyogram (EMG), deformation, strain, temperature, resistance, or voltage under cyclic motion up to 50% elongation of the ACH.

10. A method for creating a tendon-mimetic anisotropic composite hydrogel (ACH) that emulates the microstructural interplay between aligned collagen fibers and soft proteoglycans in native tissues to provide a useful implant for treatment of a patient, the method comprising:

mixing an aramid nanofiber (ANF) in dimethyl sulfoxide (DMSO) and stirring for a time sufficient to produce an ANF dispersion in DMSO;

dissolving polyvinyl alcohol (PVA) in dimethyl sulfoxide (DMSO) and stirring for a time sufficient to produce a PVA dispersion in DMSO;

mixing together the ANF dispersion in DMSO and the PVA dispersion in DMSO to form a moldable composite dispersion;

casting the moldable composite dispersion into one or more molds and immersing in deionized water for a time sufficient to produce an isotropic ANF-PVA hydrogel;

stretching the isotropic ANF-PVA hydrogel to create a stretched hydrogel;

fixing the length of the stretched hydrogel to create a fixed length;

drying the stretched hydrogel at the fixed length to create a dried stretched hydrogel; and reswelling the dried stretched hydrogel to create the ACH.

11. The method of claim 10, wherein the ANF comprises a first mass of para-aramid pulp, and the ANF dispersion in DMSO comprises a second mass of sodium hydroxide (KOH) mixed in the DMSO with the ANF.

12. The method of claim 11, wherein the first mass of para-aramid pulp and the second mass of KOH are about equal in mass.

13. The method of claim 12, wherein the ANF dispersion in DMSO comprises at least about 30 milliliters (mL) of DMSO for every gram (g) of para-aramid pulp.

14. The method of claim 13, wherein the PVA dispersion in DMSO comprises about 15 wt. % PVA.

15. The method of claim 14, wherein the moldable composite dispersion comprises about a 1:1 mass ratio of the ANF dispersion in DMSO and the PVA dispersion in DMSO.

16. The method of claim 15, wherein the dried stretched hydrogel is released from the fixed length prior to reswelling.

17. The method of claim 16, comprising chemical functionalization to present arginylglycylaspartic acid (RGD) motifs for binding with a cell membrane.

18. The method of claim 17, wherein the chemical functionalization comprises benzophenone (BPh) functionalized amphiphilic block copolymers involving linear polyglycerol (LPG) adsorbed on the surface of the ACH in an aqueous environment.

19. The method of claim 15, comprising bonding the isotropic ANF-PVA hydrogel with one or more serpentine electronics circuits to create an integrated soft bioelectronic enabled ACH.

20. A tendon-mimetic anisotropic composite hydrogel (ACH) that emulates the microstructural interplay between aligned collagen fibers and soft proteoglycans in native tissues to provide a useful implant for treatment of a patient, the ACH comprising:

an assembly of stiff aramid nanofibers (ANFs) and flexible polyvinyl alcohol (PVA) molecules attached thereto by intermolecular hydrogen bonding;

wherein the ACH has a water content between about 60% and about 74% by weight;

wherein the ACH has a primary fiber orientation direction, and the ACH exhibits an elastic modulus greater than or equal to about 1114 megapascals (MPa) and an ultimate strength greater than or equal to about 72.1; the elastic modulus and the ultimate strength, each respectively, measured in a direction parallel to the primary fiber orientation direction;

wherein the ACH exhibits a fracture energy greater than about 4 kilojoules per square meter ($kJ/m^2$), measured in a direction parallel to the primary fiber orientation direction;

wherein the ACH exhibits a fracture energy greater than about 6 $kJ/m^2$, measured in a direction perpendicular to the primary fiber orientation direction;

wherein the ACH exhibits a stiffness anisotropy characterized by the ratio (Ep/En) greater than about 10, wherein the ratio (Ep/En) is calculated between a first respective initial tensile modulus measured parallel (Ep) and a second respective tensile modulus measured perpendicular (En) to the primary fiber orientation direction;

wherein the ACH is biofunctionalized, and the ACH exhibits:

an angular frequency distribution with a majority of cells oriented within +/−15 degrees with respect to the primary fiber orientation direction;

a surface topography measurement by atomic force microscope exhibiting a measured height variation equal to or less than about 500 nano meters (nm) over a measurement area of at least about 36 square micrometers ($\mu m^2$);

a statistically significant difference (P<0.05) in mean fluorescent intensity (MFI) for cells having an M1 phenotype when compared to a similarly biofunctionalized isotropic ANF-PVA hydrogel; and a statistically significant difference (P<0.05) in mean fluorescent intensity (MFI) for cells having an M2 phenotype when compared to a similarly biofunctionalized isotropic ANF-PVA hydrogel; and wherein the ACH is fitted with one or more integrated multifunctional bioelectronic circuits configured and adapted to obtain one or more measurements selected from the group consisting of electrocardiogram (ECG), electromyogram (EMG), deformation, strain, temperature, resistance, or voltage under cyclic motion up to 50% elongation of the ACH.

\* \* \* \* \*